US012564575B2

(12) United States Patent
Lewin et al.

(10) Patent No.: US 12,564,575 B2
(45) Date of Patent: Mar. 3, 2026

(54) EARLY MANAGEMENT, MITIGATION AND PREVENTION OF SEPSIS AND SEPSIS-LIKE SYNDROMES, INCLUDING NEO-NATAL ARDS DUE TO INFECTION, INJURY OR IATROGENESIS

(71) Applicant: OPHIREX, INC, Corte Madera, CA (US)

(72) Inventors: Matthew R. Lewin, Corte Madera, CA (US); Rebecca Carter, Shalimar, FL (US)

(73) Assignee: OPHIREX, INC, Corte Madera, CA (US)

( * ) Notice: Subject to any disclaimer, the term of this patent is extended or adjusted under 35 U.S.C. 154(b) by 987 days.

(21) Appl. No.: 17/725,976

(22) Filed: Apr. 21, 2022

(65) Prior Publication Data

US 2022/0331291 A1 Oct. 20, 2022

Related U.S. Application Data

(63) Continuation-in-part of application No. 17/767,173, filed as application No. PCT/US2020/055709 on Oct. 15, 2020.

(60) Provisional application No. 63/017,966, filed on Apr. 30, 2020, provisional application No. 62/990,020, filed on Mar. 16, 2020, provisional application No. 62/915,209, filed on Oct. 15, 2019.

(51) Int. Cl.
| | |
|---|---|
| *A61K 31/404* | (2006.01) |
| *A61K 31/195* | (2006.01) |
| *A61K 31/541* | (2006.01) |
| *A61P 11/00* | (2006.01) |

(52) U.S. Cl.
CPC .......... *A61K 31/404* (2013.01); *A61K 31/195* (2013.01); *A61K 31/541* (2013.01); *A61P 11/00* (2018.01)

(58) Field of Classification Search
CPC ................ A61K 31/404; A61K 31/541; A61K 31/195
USPC ...................................................... 514/227.8
See application file for complete search history.

(56) References Cited

U.S. PATENT DOCUMENTS

2007/0231334 A1 10/2007 Alibek et al.

FOREIGN PATENT DOCUMENTS

| | | |
|---|---|---|
| WO | 2016022433 A1 | 2/2016 |
| WO | 2016069813 A1 | 5/2016 |
| WO | 2016081826 A2 | 5/2016 |

OTHER PUBLICATIONS

Nicholls, Stephen J., Varespladib and Cardiovascular Events in Patients With an Acute Coronary Syndrome The VISTA-16 Randomized Clinical Trial, JAMA Jan. 15, 2014 vol. 311, No. 3, pp. 253-262, Published online Nov. 18, 2013.
Abraham E, Naum C, Bandi V, Gervich D, Lowry S, Wunderink R, et al. Efficacy and safety of LY315920Na/S-5920, a selective inhibitor of 14-kDa group IIA secretory phospholipase A2. Crit Care Med. 2003.
Alejandro Piris Gimenez, Yong-Zheng Wu, Miguel Paya, Christophe Delclaux, Lhousseine Touqui, and Pierre L. Goossens. High Bactericidal Efficiency of Type IIA Phospholipase A2 against Bacillus anthracis and Inhibition of Its Secretion by the Lethal Toxin. J. Immunol 2004; 173:521-530.
Becker AB, Roth RA. An unusual active site identified in a family of zinc metalloendopeptidases. Proc Natl Acad Sci U S A. 1992;89(9):3835-3839. doi:10.1073/pnas.89.9.3835.
Bode W, Gomis-Ruth FX, Stockler W. Astacins, serralysins, snake venom and matrix metalloproteinases exhibit identical zinc-binding environments (HEXXHXXGXXH and Met-turn) and topologies and should be grouped into a common family, the 'metzincins'. FEBS Lett. Sep. 27, 1993;331(1-2):134-40. doi: 10.1016/0014-5793(93)80312-i. PMID: 8405391.
De Luca D, Piastra M, Tosi F, Pulitano S, Mancino A, Genovese O, et al. Pharmacological Therapies for Pediatric and Neonatal ALI/ARDS: An Evidence-Based Review. Curr Drug Targets. 2012.

(Continued)

*Primary Examiner* — Raymond J Henley, III
(74) *Attorney, Agent, or Firm* — Cosud Intellectual Property Solutions, P.C.; Henry D. Coleman

(57) ABSTRACT

The present invention relates to the early treatment, including pre-diagnosis treatment, of sepsis and acute inflammatory syndromes such as systemic inflammatory response syndrome (SIRS) by PLA2 and metalloprotease inhibitors to improve the performance of antibiotics and outcomes prior to and after confirmation of the diagnosis of sepsis and/or SIRS in a patient or subject. Additional embodiments include methods of treating sepsis, anthrax and severe acute respiratory syndrome coronavirus (SARS and SARS-CoV2) and related inflammatory syndromes and compositions, including pharmaceutical compositions and blood sample compositions. In further embodiments, the present invention is directed to embodiments which evidence that LY315920, LY333013 and related sPLA2 inhibitors are particularly effective COVID-19/cytokine release syndrome therapeutics-prophylactics. In embodiments, the PLA2 inhibitor is varespladib (LY315920), methyl varespladib (LY333013), AZD2716-(R)-3-(5'-benzyl-2'-carbamoyl-[1,1'-biphenyl]-3-yl)-2-methylpropanoic acid—as a racemic mixture or separately, as the "R" enantiomer), compound 4 (3-(5'-benzyl-2'-carbamoyl-[1,1'-biphenyl]-3-yl)-propanoic acid) and LY433771 ((9-[(phenyl)methyl]-5-carbamoylcarbazol-4-yl) oxyacetic acid), a pharmaceutically acceptable salt thereof or a mixture thereof. In embodiments, the metalloprotease inhibitor is Prinomastat, Batimastat, marimastat or vorinostat dosed alone or in combination with preferred sPLA2 inhibitors for the treatment of infection, inflammatory and wound conditions arising from various causes. Methods and compositions for achieving accelerated treatment of wounds and burns, anthrax metalloprotease toxin (lethal factor) driven complications, ARDS, neo-natal and pediatric acute respiratory distress syndrome (neo-natal/pediatric ARDS), including meconium aspiration syndrome and other disease states and conditions are also disclosed.

29 Claims, 16 Drawing Sheets

(56)                    References Cited

OTHER PUBLICATIONS

De Luca D, Vendittelli F, Trias J, Fraser H, Minucci A, Gentile L, et al. Surfactant and Varespladib Co-Administration in Stimulated Rat Alveolar Macrophages Culture. Curr Pharm Biotechnol. 2013.

De Luca D, Capoluongo E, Rigo V. Secretory phospholipase A2 pathway in various types of lung injury in neonates and infants: A multicentre translational study. BMC Pediatr. 2011.

Dennis EA, Cao J, Hsu YH, Magrioti V, Kokotos G. Phospholipase A2 enzymes: Physical structure, biological function, disease implication, chemical inhibition, and therapeutic intervention. Chemical Reviews. 2011.

Friebe S, van der Goot FG, Burgi J. The Ins and Outs of Anthrax Toxin. Toxins (Basel). Mar. 10, 2016;8(3):69. doi: 10.3390/toxins8030069. PMID: 26978402; PMCID: PMC4810214.

Furue S, Kuwabara K, Mikawa K, Nishina K, Shiga M, Maekawa N, et al. Crucial role of group IIA phospholipase A2 in oleic acid-induced acute lung injury in rabbits. Am J Respir Crit Care Med. 1999.

Giordanetto F, Pettersen D, Starke I, Nordberg P, Dahlstrom M, Knerr L, Selmi N, Rosengren B, Larsson LO, Sandmark J, Castaldo M, Dekker N, Karlsson U, Hurt-Camejo E. Discovery of AZD2716: A Novel Secreted Phospholipase A2 (sPLA2) Inhibitor for the Treatment of Coronary Artery Disease. ACS Med Chem Lett. Aug. 9, 2016;7(10):884-889.

Goldberg AB, Turk BE. Inhibitors of the Metalloproteinase Anthrax Lethal Factor. Curr Top Med Chem. 2016;16(21):2350-8.

Gomis-Ruth FX, Kress LF, Bode W. First structure of a snake venom metalloproteinase: a prototype for matrix metalloproteinases/collagenases. Embo J. 1993;12(11):4151-4157.

Hooper NM. Families of zinc metalloproteases. FEBS Lett. Oct. 3, 19941;354(1): 1-6. doi: 10.1016/0014-5793(94)01079-x. PMID: 7957888.

Jiang W, Bond JS. Families of metalloendopeptidases and their relationships. FEBS Lett. Nov. 9, 1992;312(2-3):110-4. doi: 10.1016/0014-5793(92)80916-5. PMID: 1426239.

Klimpel KR, Arora N, Leppla SH. Anthrax toxin lethal factor contains a zinc metalloprotease consensus sequence which is required for lethal toxin activity. Mol Microbiol. Sep. 1994;13(6):1093-100. doi: 10.1111/j.1365-2958.1994.tb00500.x. PMID: 7854123.

Liu, S, Moayeri,M. and Leppla,S.H. Anthrax lethal and edema toxins in anthrax pathogenesis. Trends Microbiol. 22 (6), 317-325 (2014).

Magrioti V, Kokotos G. Phospholipase A2 inhibitors for the treatment of inflammatory diseases: A patent review (2010-present). Expert Opinion on Therapeutic Patents. 2013.

Piris-Gimenez A, Paya M, Lambeau G, Chignard M, Mock M, Touqui L, Goossens PL. In vivo protective role of human group IIa phospholipase A2 against experimental anthrax. J Immunol. Nov. 15, 2005;175(10):6786-91. doi: 10.4049/jimmunol.175.10.6786. PMID: 16272335.

Rawlings ND, Barrett AJ. Evolutionary families of peptidases. Biochem J. Feb. 15, 1993;290 ( Pt 1)(Pt 1):205-18. doi: 10.1042/bj2900205. PMID: 8439290; PMCID: PMC1132403.

Raymond B, Leduc D, Ravaux L, et al. Edema toxin impairs anthracidal phospholipase A2 expression by alveolar macrophages. PLoS Pathog. 2007;3(12):e187. doi:10.1371/journal.ppat.0030187.

Santos AA, Browning JL, Scheltinga MR, Lynch EA, Brown EF, Lawton P, et al. Are events after endotoxemia related to circulating phospholipase A2? Ann Surg. 1994.

Shoop WL, Xiong Y, Wiltsie J, Woods A, Guo J, Pivnichny JV, Felcetto T, Michael BF, Bansal A, Cummings RT, Cunningham BR, Friedlander AM, Douglas CM, Patel SB, Wisniewski D, Scapin G, Salowe SP, Zaller DM, Chapman KT, Scolnick EM, Schmatz DM, Bartizal K, MacCoss M, Hermes JD. Anthrax lethal factor inhibition. Proc Natl Acad Sci U S A. May 31, 2005;102(22):7958-63.

Sims K. Kochi, Giampietro Schiavo, Michele Mock, Cesare Montecucco, Zinc content of the Bacillus anthracis lethal factor, FEMS Microbiology Letters, vol. 124, Issue 3, Dec. 1994, pp. 343-348.

Sohail HA, Gutierrez JM, Mebs D, Rowan EG, Sohail M, Warrell DA. Venoms, poisons and toxins: evolution and impact of amazing molecules. J Venom Res. 2020;10:1-6. Published Jan. 12, 2020.

Sweeney DA, Cui X, Solomon SB, Vitberg DA, Migone TS, Scher D, Danner RL, Natanson C, Subramanian GM, Eichacker PQ. Anthrax lethal and edema toxins produce different patterns of cardiovascular and renal dysfunction and synergistically decrease survival in canines. J Infect Dis. Dec. 15, 2010;202(12):1885-96. doi: 10.1086/657408. Epub Nov. 10, 2010. PMID: 21067373; PMCID: PMC3061475.

Abraham E, et al. Efficacy and safety of LY315920Na/S-5920, a selective inhibitor of 14-kDa group IIA secretory phospholipase A2, in patients with suspected sepsis and organ failure. Critical Care Medicine, 2003, 31(3):718-728.

Castro MM, et al. Matrix metalloproteinase inhibitor properties of tetracyclines: Therapeutic potential in cardiovascular diseases. Pharmacological Research, 2011;64:551-560.

Liang S.Y, et al. Empiric antimicrobial therapy in severe sepsis and septic shock: optimizing pathogen clearance. Curr Infect Dis Rep, 2015;17(7): Capter "Combination therapy" p. 493.

National Guidelines for Clinical Management and Treatment of COVID-19. Apr. 3, 2020, Version 2. Prepared and Reviewed by National committee for Management of COVID-19 Cases. United Arab Emirates Ministry of Health & Prevention [online]. (retrieved on 12.12.2020). Retrieved from https://www.dha.gov.ae/en/HealthRegulation/Documents/COVID%20National%20Guidelines%20FINAL%2018%20March.pdf.

Vijay R, et al. Critical role of phospholipase A2 group IID in age-related susceptibility to severe acute respiratory syndrome-CoV infection. J Exp Med, 2015;212(11):1851-1868.

Phillips JM, et al. Neurovirulent Murine Coronavirus JHM.SD Uses Cellular Zinc Metalloproteases for Virus Entry and Cell-Cell Fusion. Journal of Virology, 2017, V. 91 I. 8, e01564-16:1-16, p. 1-20.

Angert RM, et al. CC10 Reduces Inflammation in Meconium Aspiration Syndrome in Newborn Piglets. Pediatric Research, 2007;62(6):684-688.

De Luca D, et al. Varespladib Inhibits Secretory Phospholipase A2 in Bronchoalveolar Lavage of Different Types of Neonatal Lung Injury. The Journal of Clinical Pharmacology, 2012;52(5):729-737.

Shen LW, et al. TMPRSS2: A potential target for treatment of influenza virus and coronavirus infections. Mini-review, Biochimie, 2017;142:1-10 https://doi.org/10.1016/j.biochi.2017.07.016.

ISA/RU. PCT Search Report for PCT/US22/055709. Feb. 4, 2021.

FIGURE 1

Table 1

| Parameter | Score per field | | |
|---|---|---|---|
| | 0 | 1 | 2 |
| Neutrophils in the alveolar space | None | 1–5 | >5 |
| Neutrophils in the interstitial space | None | 1–5 | >5 |
| Proteinaceous debris filling the airspaces | None | 1 | >1 |
| Alveolar septal thickening | <2× | 2×–4× | >4× |

FIGURE 1B

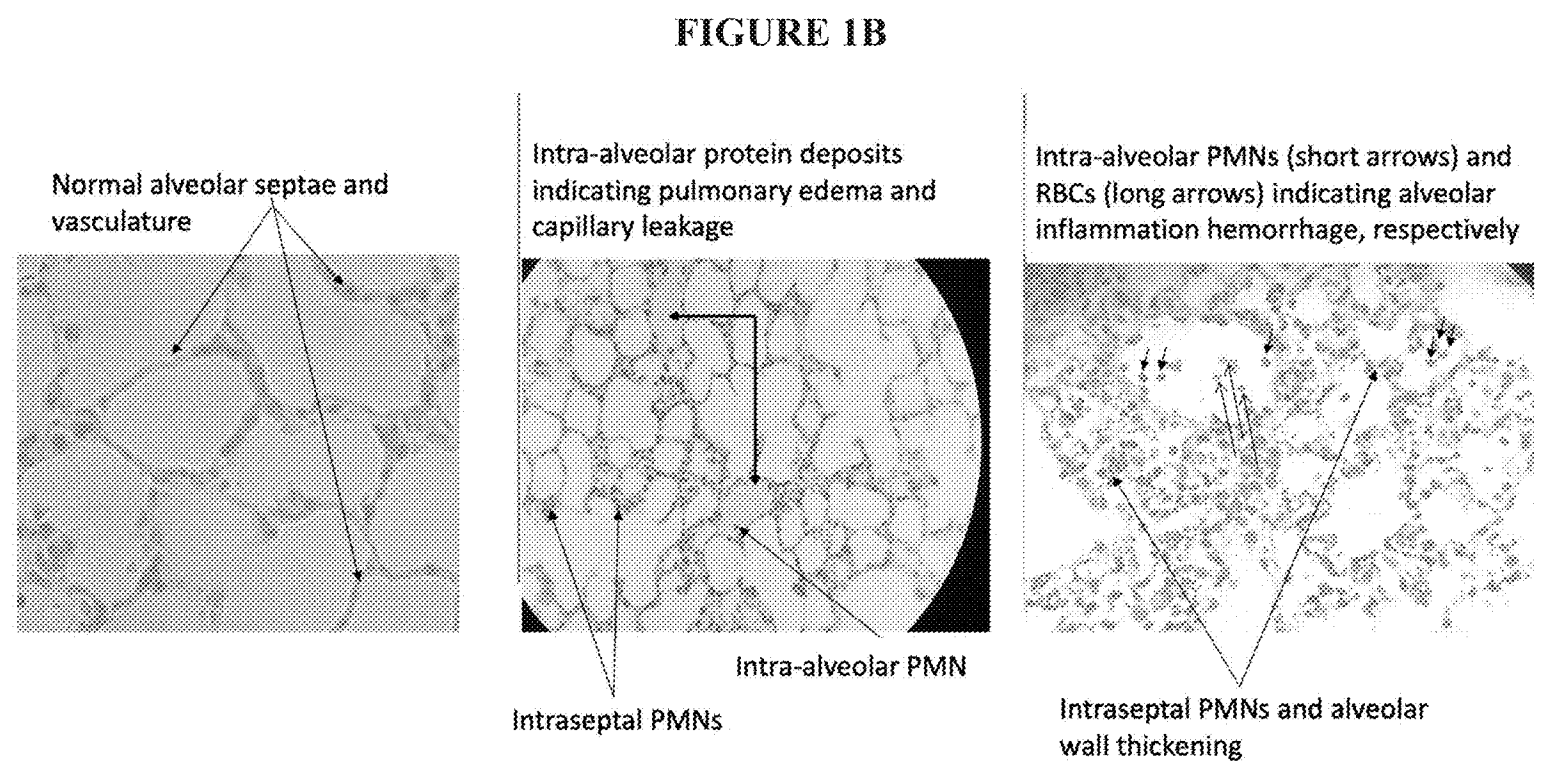

Normal alveolar septae and vasculature

Intra-alveolar protein deposits indicating pulmonary edema and capillary leakage Intra-alveolar PMN Intraseptal PMNs Intra-alveolar PMNs (short arrows) and RBCs (long arrows) indicating alveolar inflammation hemorrhage, respectively Intraseptal PMNs and alveolar wall thickening

FIGURE 2

Mice with ARDS have demonstrably louder pulmonary crackles

Mice treated with AZD2716

FIGURE 4

Table 2

| Snake species and geography | Prinomastat | Batimastat | Marimastat | Anthrax Lethal Factor Inhibitor |
|---|---|---|---|---|
| *Agkistrodon contortrix laticinctus* (Copperhead-USA) | 0.02 | 0.12 | 0.23 | indeterminate |
| *Agkistrodon piscivorus conanti* (Florida Cottonmouth-USA) | 0.01 | 0.04 | 0.16 | indeterminate |
| *Agkistrodon piscivorus* (E. Cottonmouth) | 0.002 | 0.005 | 0.025 | 8.8 |
| *Bitis arietans* (Puff Adder-Africa) | 0.002 | 0.005 | 0.009 | 38 |
| *Bothrops atrox* (Fer de Lance-Latin America) | 0.01 | 0.16 | 0.2 | 0.4 |
| *Crotalus adamanteus* (E. Diamondback-USA) | 0.008 | 0.045 | 0.06 | 1.1 |
| *Crotalus atrox* (W. Diamondback-USA) | 0.175 | 0.35 | 0.4 | 1.3 |
| *Crotalus helleri* (Pacific Coast Rattler-USA) | 0.006 | 0.02 | 0.02 | 0.09 |
| *Crotalus viridis* (Prairie Rattler-USA) | 0.003 | 0.007 | 0.01 | 0.6 |
| *Disphalidus typus* (Boomslang-Africa) | 0.002 | 0.005 | 0.008 | 0.3 |
| *Echis carinatus sochureki* (Saw Scale Viper-India) | 0.01 | 0.06 | 0.1 | 9.4 |
| *Echis pyramidum* (Saw Scale Viper-Africa) | 0.008 | 0.03 | 0.10 | 2.0 |
| *Gloydius b. brevicaudus* (Korean Mamushi-Asia) | 0.003 | 0.01 | 0.03 | 3.1 |
| *Sistrurus barbieri milliari* (Pygmy Rattler-USA) | 0.0002 | 0.001 | 0.002 | 0.01 |
| *Trimeresus elegans* (Elegant Pit Viper-Asia) | 0.024 | 0.09 | 0.2 | 8.9 |
| *Vipera ammodytes* (Adder-Europe/Middle East) | 0.014 | 0.05 | 0.2 | 4403 |
| *Vipera berus* (Adder-Europe/Eurasia) | 0.14 | 0.1 | 0.2 | 2.7 |

FIGURE 6

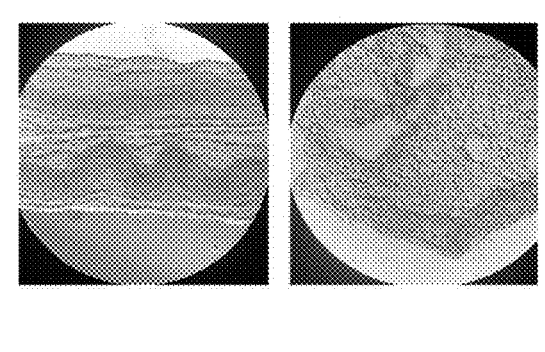

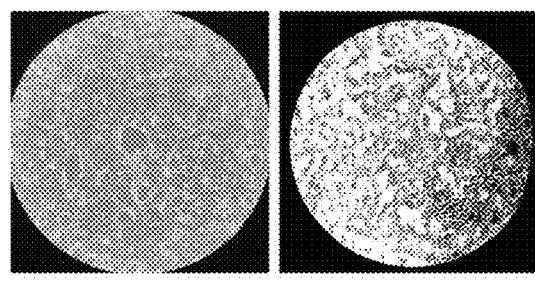

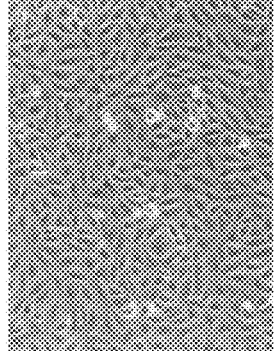

Normal, confluent epithelial cells in cell culture media

Epithelial cells in cell culture media exposed to whole rattlesnake (top) and copperhead (below) venoms show lacune formation, retraction and incipient detachment as a result of toxic MP and sPLA2 activities Epithelial cells in cell culture media exposed to whole rattlesnake (top) and copperhead (below) venoms detachment as a result of toxic MP and sPLA2 activities similar to that occurring in ARDS and acute kidney injury

FIGURE 11
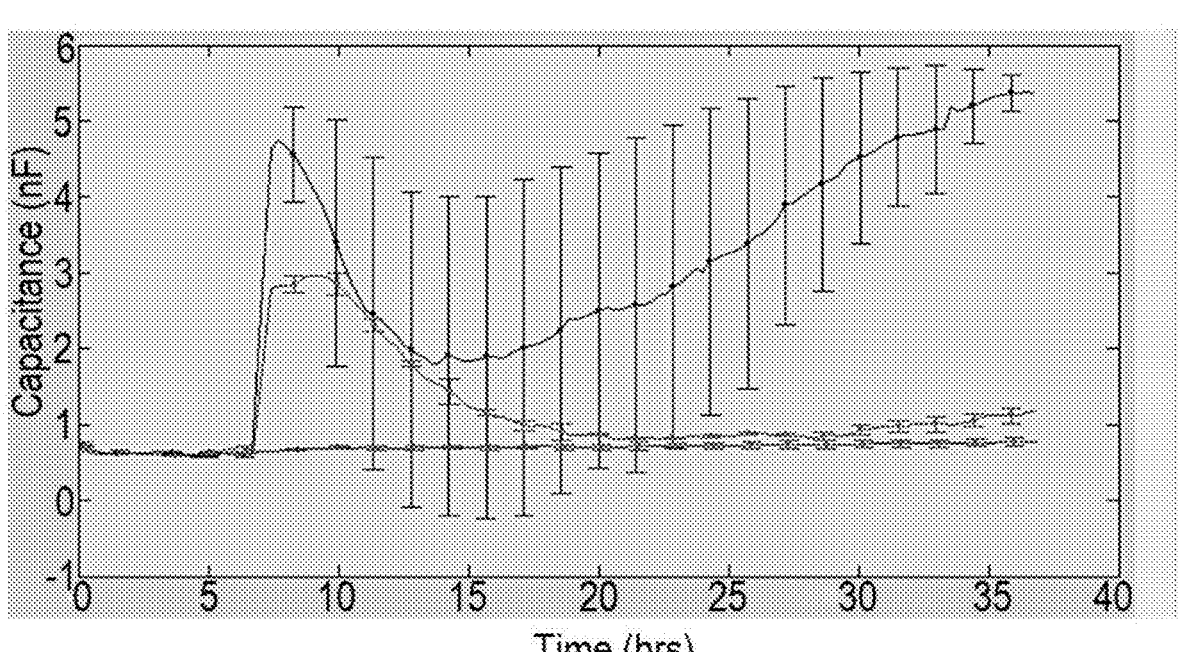
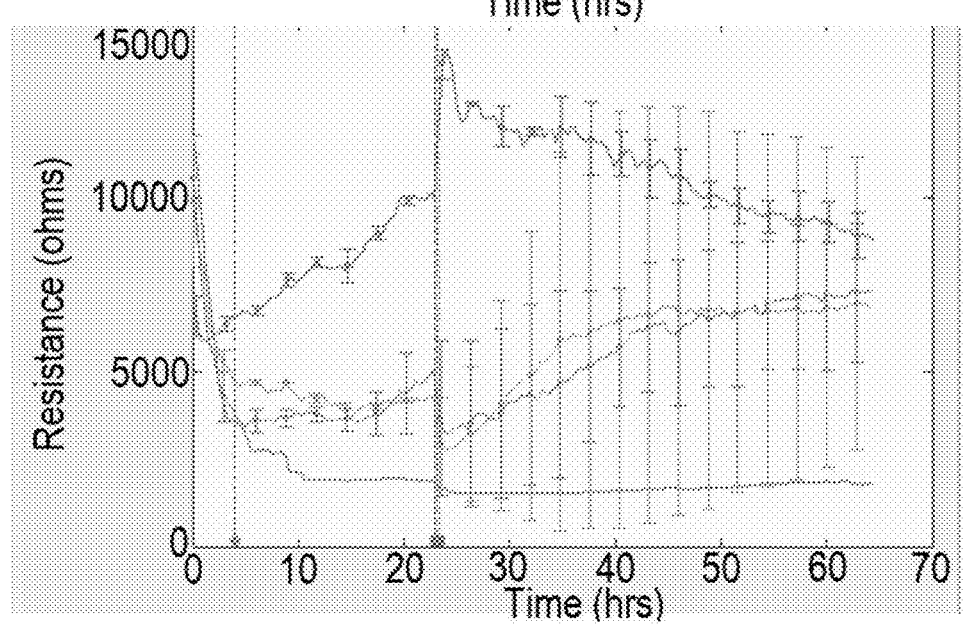

FIGURE 13

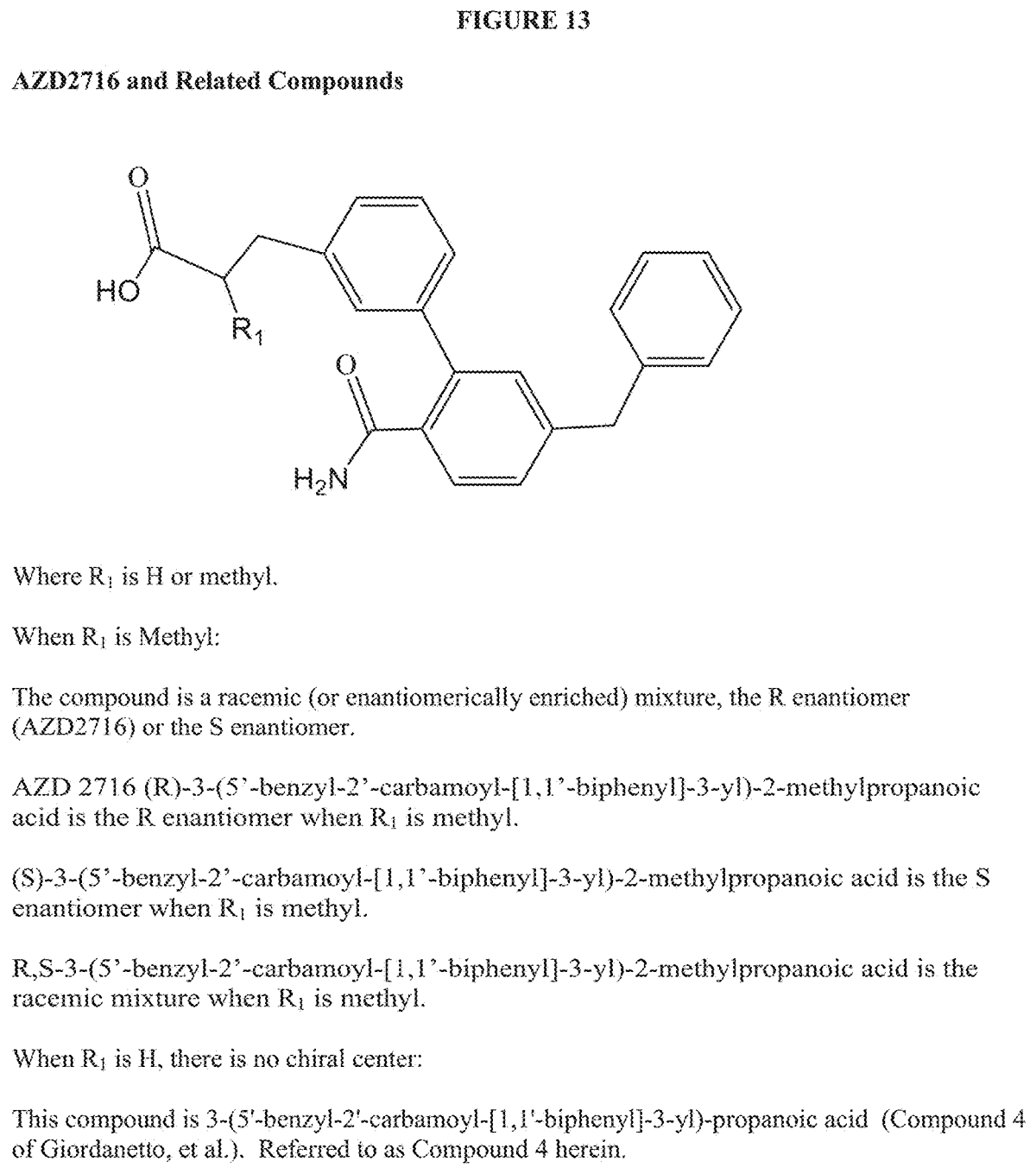

AZD2716 and Related Compounds

Where $R_1$ is H or methyl.

When $R_1$ is Methyl:

The compound is a racemic (or enantiomerically enriched) mixture, the R enantiomer (AZD2716) or the S enantiomer.

AZD 2716 (R)-3-(5'-benzyl-2'-carbamoyl-[1,1'-biphenyl]-3-yl)-2-methylpropanoic acid is the R enantiomer when $R_1$ is methyl.

(S)-3-(5'-benzyl-2'-carbamoyl-[1,1'-biphenyl]-3-yl)-2-methylpropanoic acid is the S enantiomer when $R_1$ is methyl.

R,S-3-(5'-benzyl-2'-carbamoyl-[1,1'-biphenyl]-3-yl)-2-methylpropanoic acid is the racemic mixture when $R_1$ is methyl.

When $R_1$ is H, there is no chiral center:

This compound is 3-(5'-benzyl-2'-carbamoyl-[1,1'-biphenyl]-3-yl)-propanoic acid (Compound 4 of Giordanetto, et al.). Referred to as Compound 4 herein.

EARLY MANAGEMENT, MITIGATION AND PREVENTION OF SEPSIS AND SEPSIS-LIKE SYNDROMES, INCLUDING NEO-NATAL ARDS DUE TO INFECTION, INJURY OR IATROGENESIS

RELATED APPLICATIONS

This application is a continuation-in-part application of U.S. patent application Ser. No. 17/767,173, filed Apr. 7, 2022, which is a national phase filing claiming the benefit of priority of PCT/US20/55709, filed 15 Oct. 2020, which claims the benefit of priority of U.S. provisional application Ser. No. 62/915,209, filed Oct. 15, 2019; 62/990,020, filed Mar. 16, 2020; and 63/017,966, filed Apr. 30, 2020, the entire contents of each of the aforementioned applications being incorporated by reference herein.

FIELD OF THE INVENTION

The present invention relates to the early treatment, including pre-diagnosis treatment, of sepsis and acute inflammatory syndromes such as systemic inflammatory response syndrome (SIRS) by PLA2 and metalloprotease inhibitors to improve the performance of antibiotics and outcomes prior to and after confirmation of the diagnosis of sepsis and/or SIRS and tumor spread in a patient or subject. Additional embodiments include methods and compositions for treating wounds and lesions caused by toxins, trauma, or slow wound healing due to basement membrane or other damage as well as oncogenic processes involved with solid and hematologic cancer spread. Further embodiments are directed to compositions, including pharmaceutical compositions and blood sample compositions. In further embodiments, the present invention is directed to embodiments which evidence that LY315920, LY333013 and related sPLA2 inhibitors are particularly effective COVID-19/cytokine release syndrome therapeutics-prophylactics (e.g. mRNA and other vaccines) and those conditions leading to preterm labor in pregnancy. In embodiments, the PLA2 inhibitor is varespladib (LY315920), methyl varespladib (LY3330I 3), AZD2716-(R)-3-(5'-benzyl-2'-carbamoyl-[1, 1'-biphenyl]-3-yl)-2-methylpropanoic acid—as a racemic mixture (i.e., R,S-3-(5'-benzyl-2'-carbamoyl-[1,1'-biphenyl]-3-yl)-2-methylpropanoic acid), compound 4 (3-(5'-benzyl-2'-carbamoyl-[1,1'-biphenyl]-3-yl)-propanoic acid) as set forth herein below or LY433771 ((9-[(phenyl)methyl]-5-carbamoylcarbazol-4-yl) oxyacetic acid), a pharmaceutically acceptable salt thereof or a mixture thereof. In embodiments, the metalloprotease inhibitor is prinomastat, batimastat, marimastat or vorinostat dosed alone or in combination (prinomastat is often the metalloprotease of choice) with preferred sPLA2 inhibitors for the treatment of infection, inflammatory and wound conditions, including those wounds caused by bacterially, virally, venom-induced, burns and traumatically arising from various causes at macro- and micro-scopic scales. Methods of accelerated treatment of wounds, acute kidney injury (AKI), anthrax lethal factor toxin associated complications, ARDS, neo-natal and pediatric acute respiratory distress syndrome (neo-natal/pediatric ARDS), including meconium aspiration syndrome are also disclosed with special attention to AZD2716-(R)-3-(5'-benzyl-2'-carbamoyl-[1,1'-biphenyl]-3-yl)-2-methylpropanoic acid—as a racemic mixture or a stereoisomer thereof, often the "R" enantiomer of the racemic mixture alone or in combination with a metalloprotease inhibitor (e.g. prinomastat) or as a composition for accelerating wound healing such as that arising from injury or toxins affecting connective tissues associated with epithelia.

BACKGROUND AND OVERVIEW OF THE INVENTION

Preservation and/or accelerated healing of the basement layer membrane, epithelium, and endothelium is foundational for health in nearly every organ and tissue system of the body. These layers form the basic structure in nearly all tissues and organs. Destruction of these layers or loss of function leads to pathogenesis of immune function, pulmonary system, gastrointestinal system, renal system, integumentary system, and circulatory system. Altogether, these experiments indicate that preservation of this critical structure through both the epithelial and endothelial layers results in significant improvement in cellular, systemic, and whole organism function that are unexpectedly and uniquely protected and treated by compositions and kits related to combinations of sPLA2 and metalloprotease inhibitors individually and in combinations.

In pre-hospital emergency medical care as well as in early goal directed therapy (EGDT) for sepsis, there has been a recent push to administer antibiotics earlier and earlier to a patient or subject with severe burns and/or traumatic injury in order to ameliorate and/or prevent sepsis and acute inflammatory syndromes. The principal problems with this approach is that is of debatable benefit and it is difficult to de-escalate, but while paramedics and first responders may be skilled at identifying the signs and/or symptoms associated with sepsis and SIRS, their proximity to advanced diagnostic and care facilities limits accuracy and puts correct laboratory sampling (e.g. blood cultures) and correct antibiotic selection at risk. An approach to mitigating the physiological disorder associated with sepsis/SIRS, would be beneficial for initial stabilization, treatment and ultimate prognosis for these patients, particularly if such an approach could be administered very early in the disease progression. Further, such an approach would have particularly useful benefit in remote and low-resource settings as well as theatres of war and in the treatment of military personnel who are often severely burned and/or injured resulting in high risk of infection, sepsis and SIRS.

Injured military personnel are most often at risk of sepsis and/or SIRS pursuant to Prolonged Field Care (PFC) which is the area of concern for the military dealing with holding a patient, often an injured patient, in a pre-hospital environment waiting for evacuation to a medical facility appropriate to further treatment of the injured patient. The military benefit of an effective pre-diagnostic option is substantial.

Military medical systems are arranged in five (5) echelons or roles of care in the treatment of injured patients:

Role 1—is directed to front line, typically self-aid/buddy care and TCCC (Tactical Combat Casualty Care). Small unit medics also operate at this level;

Role 2—is directed to small aid station, advanced trauma management and emergency medical treatment including continuation of resuscitation started in Role 1; patient stabilization;

Role 3—is directed to Military Treatment Facilities (MTF's) within the theater of operation (for example, Kandahar hospital in Afghanistan); staffed and equipped to provide care to all categories of patients, to include resuscitation, initial wound surgery, specialty surgery (general, orthopedic, urogenital, thoracic, ENT, neurosurgical) and post-operative treatment Role 4—Regional US or robust overseas hospital with many specialists (for example Landstuhl hospital in Germany)

Role 5—Large US based DoD or VA Hospital

Perhaps unsurprisingly, outcomes from trauma in military/combat settings are heavily dependent on transport time to higher levels of care. Currently, for addressing the treatment of conventional troops, the military has become very efficient at transport back to Role 3 from Role 1, above, reducing times significantly. This has had the very positive result of improving outcomes and reducing morbidity/mortality. But even in this best case scenario, sepsis leading to acute respiratory distress syndrome (ARDS) and other sequalae is a high risk from trauma. Prolonged treatment with specific antibiotics is the norm.

However, United States Special Operations Command (USSOCOM) and other units of medics operate at the Role 1 echelon of care and operate in areas that are not well supported with transport and evacuation times taking up to 72 hours (or much longer) from time to call to pick up. This prolongs the amount of time that the medic needs to support a battlefield trauma, substantially increasing the risk to the injured patient.

One of the major issues that may occur is infection leading to sepsis, particularly given the type of injuries that may be sustained. The military has searched for ways to treat for infection, but keep coming back to the need for diagnosis prior to treatment, or general antibiotic therapy that the medic has on hand along with wound cleansing and debridement. There are few or no diagnostics that can be supported by USSOCOM medics in the field and they carry only broad spectrum antibiotics, most often ineffective against several infections which cause sepsis.

The present invention is directed to the addition of PLA2/MP inhibitors to a therapeutic regimen that would support antibiotic administration to prevent or mitigate the effects toxins from infection and allow a higher level care and/or the front line medic to support the patient.

The inventors have, by surprise, enabled a key invention related to the treatment of inflammatory conditions for particular use in preventing and ameliorating inflammation associated with infection and attenuating the likelihood of sepsis in patients. There has been a big push in pre-hospital care to give antibiotics earlier and earlier to the point of ambulance personnel doing so in the field. This has raised many important treatment timing issues not just in the pre-hospital setting, but in the receiving facilities, as well. The present invention can be used to provide a pre-diagnostic treatment for ameliorating and/or reducing the likelihood of catastrophic treatment failure in a patient at risk for sepsis which meets a long-unmet need.

The present invention relates to the following concepts, among others as described herein. Early use of sPLA2 inhibitors such as varespladib (LY315920), methyl-varespladib (LY333013), (AZD2716—as a racemic mixture or R and S isomers thereof or Compound 4 (i.e., AZD compound 4 from the same series as described herein) and carbazols such as LY433771, among others prevents and mitigates the rise of sPLA2, stabilizing the patient sufficiently to improve and simplify pre-diagnosis care of the patients, promote wound healing, stabilize the patients and preserve the integrity of blood cultures, reduce blood culture contamination prior to antibiotics and improve the performance of antibiotics.

While much has been written on the need for early recognition and treatment of sepsis and related syndromes (e.g. SIRS), the focus has been on early treatment with antimicrobial agents, especially as it pertains to interventions available to pre-hospital and receiving emergency department personnel. Unresolved is the matter of EGDT is not only what antibiotic is best used initially by personnel in the advance of a diagnosis and consequences related to:

1. Misuse/overuse and timing of fluids and antibiotics; and

2. Disruption/adequacy of blood cultures/samples drawn in the pre-hospital setting.

The current invention addresses the limitations of pre-hospital and pre-diagnosis fluids and antibiotics by safely mitigating the effects of suspected or confirmed sepsis syndromes in the pre-hospital or early hospital setting and 1) eliminating the need to prematurely choose from a panel of available antibiotics while, additionally, mitigating the consequences of an incorrect or suboptimal antibiotic choice 2) preserving the integrity of the blood for culture and testing at the receiving facility 3) preservation of vital signs allowing greater flexibility in critical areas such as fluid management.

Unmet Needs of the Present Invention

1. Early antibiotics are a key to outcome in infection, acute inflammation and their sequelae and:

a. antibiotic choice is difficult in low resource environments and optimal pre-diagnosis antibiotic or anti-viral choice may be difficult or impossible even in receiving clinic or hospital facilities b. inappropriate/suboptimal antibiotic or antiviral choice may result in bad outcomes, overuse or corruption of blood cultures c. small molecule anti-toxin therapy to assist in treatment of antibiotic resistant organisms to aid antibiotic treatment and preserve limited antibiotic availability d. if pre-hospital personnel and preadmission patients had a single drug, drug mixture or drugs for co-administration to improve physiological parameters prior to rise in or to halt the progression of the inflammatory response to infection or biological agent then the protocols for treatment could be simplified and made safer without complicating disease or treatment e. prophylactic use, early use and pre-antibiotic of sPLA2 and metalloprotease inhibitor agents could improve the performance of antibiotics, mitigate and reduce the incidence of inappropriate antibiotic use while stabilizing the patient and also have utility as biodefense agents for civilians and personnel with occupation risk of exposure such as in warfare and have, by themselves, therapeutic efficacy (e.g. varespladib/methyl-varespladib/AZD2716 (as racemate or enantiomer)/compound 4 (3-(5'-benzyl-2'-carbamoyl-[1,1'-biphenyl]-3-yl)-propanoic acid) and related compounds for sPLA2 inhibition and/or for example, prinomastat, batimastat, marimastat, vorinostat for metalloprotease inhibition)

f. Such agents could be stockpiled for biodefense, be stocked in ambulances at low cost and in hospitals as part of the early response to suspected infections and SIRS such as those induced in the community by:

i. Pneumonia, hemolytic uremic syndrome, enterotoxigenic E. coli, urinary tract infection, wound infection, infection derived toxins such as anthrax lethal factor, botulism and other types of bacteremia such as those induced by marine infections (e.g. *Vibrio* and *mycobacterium*) that spread rapidly and are often given inappropriate antibiotics such as cephalosporins.

ii. Viral infections prior to diagnosis such as ebola g. Increase the safety and utility of connective tissue weakening antibiotics such as quinoloines (e.g. ciprofloxacin, levofloxacin)

h. Improve the performance of antibiotics, improve fluid management and other elements of EGDT prior to the time sPLA2 is thought to peak in the progression of inflammatory conditions related to infection or systemic inflammatory response syndromes.

i. Improve wound management and healing from burns, trauma, toxin, venom, and acceptance and healing of skin grafts.

j. Reduce complications associated with infusion of CAR-T therapies and other cell-based immunotherapies based on modified immune system cells.

k. Be combined with other PLA2 inhibitors (e.g. cPLA2, iPLA2, Lp-PLA2) and metalloprotease inhibitors to reduce unwanted inflammatory and tissue degrading responses in a tailored or prophylactic fashion.

l. Be combined with antibiotics already possessing desirable properties such as intrinsic sPLA2 or metalloprotease inhibition (e.g. doxycycline, Prinomastat, marimastat batimastat) enabling a narrower list of optimal antibiotic choices in the pre-hospital and early hospital setting for patients at risk of inflammatory syndromes due to infection, trauma or as a result of inflammation-inducing treatments for conditions such as blood cancers (e.g. CAR-T therapies).

m. Metalloprotease inhibitors may, unexpectedly have general application in ARDS and wound healing by themselves as single agents-especially surprising in ARDS and in combination with sPLA2 inhibitors.

For treatment of ARDS, pulmonary surfactant, produced by Type 2 epithelial cells (T2C), is a key lung protectant and mechanical lubricant containing several classes of lipids, including phospholipids, triglycerides, cholesterol, and fatty acids key to its function. It serves a cardinal part in lungs' innate and adaptive immune response and plays a critical role in pulmonary function by the reduction of surface tension. Host defense properties of pulmonary surfactant include direct interaction of surfactant components with pathogens (viruses, bacteria) or their products (e.g. endotoxin, viral glycoproteins); stimulation of phagocytosis by surfactant components (as an opsonin or active ligand); influence of the chemotaxis of immune-competent cells; and regulation of cytokine release and reactive oxygen production by macrophages. The hydrophilic surfactant apoproteins SP-A and SP-D have distinct functions in the innate immune response to microbial challenge. In addition, the surfactant lipids suppress a variety of immune cell functions, including activation, proliferation, and immune response of lymphocytes, granulocytes, and alveolar macrophages and can even promote bacterial lysis. Upon failure of this first line of defense by pulmonary surfactant, the innate immune system which relies on a series of germ-line encoded pattern recognition receptors (PRR) that are expressed on epithelial and innate immune cells, is activated. Toll-like receptors (TLR) constitutes one of four major classes of PRR, and these PRR are sensors for pathogen-derived, evolutionarily conserved molecular structures. Most TLRs are expressed at the cell surface where they interact with bacterial components and viral proteins. (47) In lung tissues, sPLA2 is a mediator of the normal inflammatory response through release of lipid mediators and pulmonary mechanical function through its direct role in pulmonary surfactant turnover. Pulmonary sPLA2 is a critical mediator of lung function through its metabolism of surfactant and plays a key role in the homeostasis and recycling of surfactant proteins that reside in these thin, but extraordinarily important fluid planes. Critically, elevated sPLA2 levels in pulmonary alveoli, results in surfactant catabolism and even greater release of factors, including TNF-α, TNF-ß and IL-6. These cycles of inflammation and surfactant destruction act synergistically to the point at which the innate immune response to insult becomes lethally maladaptive.

Coronavirus disease 2019 (COVID-19) is an infectious disease caused by severe acute respiratory syndrome coronavirus 2 (SARS-CoV-2). Coronaviruses are primarily spread between people in close proximity to each other by coughing, sneezing, and talking. COVID-19 can affect the upper (sinuses, nose, and throat) and lower (trachea and lungs) respiratory tract. The lungs are the organ most affected by COVID-19 because the virus accesses host cells via the receptor angiotensin-converting enzyme 2 (ACE2), which is abundant in pulmonary alveolar epithelial type II cells (T2C) and is expressed heavily in alveolar capillary endothelial cells. Currently and urgently of interest, pandemic SARS-CoV-2 infections are resulting in an unusually high spike in incidence and mortality from acute respiratory distress syndrome (ARDS). ARDS is a terrifying, life-threatening and difficult to treat clinical complex of lung failure from direct or indirect physiological or physical insult. Patients with severe COVID-19 frequently have signs and symptoms of systemic inflammation, which may be mediated by Toll-like receptors and driven by dysregulated feedback loops involving sPLA2, interleukin 6 (IL-6) and tumour necrosis factor alpha (TNF-α). Systemic overexpression of sPLA2 may occur with infection that can result in degradation of surfactant and cytokine overexpression, leading to the onset of ARDS. ARDS is associated with physical, physiological and infectious insults such as those caused by blunt trauma, barotrauma and, infections, including SARS-CoV-2 infections. The most common clinical disorders associated with the development of ARDS are bacterial and viral pneumonia. When the lung is injured by infection, trauma, or inflammatory conditions, inflammatory pathways are activated. During the course of SARS-CoV-2 infection in the lower respiratory tract, damage to surfactant-producing alveolar epithelial T2C may exacerbate the overall severity of the resultant COVID-19. The inflammatory response and the innate immune barrier created by pulmonary surfactant, along with its role in innate and adaptive immune response can aid in pathogen clearance, however, excess inflammation can contribute to alveolar damage, loss of protective surfactant, increased endothelial and epithelial permeability, which results in pulmonary edema and reduced pulmonary compliance. At a molecular level, sPLA2 plays a key role in the homeostasis of surfactants and protein levels in the lung. During events that have increased pathophysiological effects, such as acute respiratory viral infection, elevated sPLA2 result in excess inflammation and enzymatic degradation of surfactant phospholipids and associated proteins at a higher rate than it is formed. This contributes to loss of protective surfactant layer followed by alveolar damage, increased endothelial and epithelial permeability, accumulation of debris, reduction of innate and adaptive pulmonary immune function, and widespread loss of functioning lung tissue, loss of lung tissue elasticity, and when severe, ARDS. Elevated sPLA2 levels or dysregulated phospholipase activity may result in the development of MOF by directly injuring the lung, either by the cytotoxic effect of elevated sPLA2 on alveolar cells or by the ability of sPLA2 to degrade surfactant. sPLA2 may also induce organ injury by producing a variety of pro-inflammatory molecules (eg, prostacyclin, thromboxane A2, leukotrienes. The resulting pulmonary edema and reduced pulmonary compliance further damages alveoli and surfactant producing cells required to protect these air sacs. Once edematous fluid accumulates in the interstitial and air spaces of the lungs, clinical outcomes include hypoxemia, impaired gas exchange, acid-base imbalances, reduced carbon dioxide excretion, and ultimately, respiratory failure. Further cycles of inflammation and lung tissue loss result, such that there is a cascade of dysfunctional immune responses characteristic of ARDS. In addition to the disruption of the lung microvascular and surfactant barriers, increased tissue permeability can also lead to a new cycle of excessive inflammation such that there is a cascade of upregulated and dysfunctional immune responses. ARDS is further associated with coagulation abnormalities due to elevated cytokines and tissue factor expression. The role that sPLA2 plays in this syndrome is likely multifactorial as it can cause inflammation as well as damage surfactant, the substance that coats the alveolar epithelium, and prevents alveolar collapse by reducing surface tension.

Surfactant dysfunction in neonates and children may play a role as pulmonary surfactant typically recycled in a highly complex and regulated mechanism becomes dysregulated. Surfactant turnover is choreographed by Type II cells, macrophages and the alveolar lining. Alveolar secreted apoprotein-rich, active surfactant aggregates are converted into protein-poor, inactive forms by the cyclical changes in the alveolar surface and are ready for clearance by Type 11 cells and alveolar macrophages. SPs are re-secreted with surfactant by lamellar bodies, whereas endocytosed phospholipids are recycled and re-secreted by Type II cells. This process is slower in newborns (especially those born prematurely) than in adults or those with lung injury. Morbidity and mortality in preterm and term neonates is due to defective surfactant metabolism secondary to accelerated breakdown of the surfactant complex by oxidation, proteolytic degradation, and inhibition.

Respiratory Distress Syndrome (RDS) in preterm neonates is present shortly after birth with apnoea, cyanosis, grunting, inspiratory stridor, nasal flaring, poor feeding, and tachypnoea. It is one of the most common causes of morbidity and it occurs worldwide with a slight male predominance Compared to a mature lung, RDS is characterised by low volume of surfactant containing a lower percent of di-saturated phosphatidylcholine species, phosphatidylglycerol, and surfactant proteins. Histopathological findings in lungs of RDS show alveolar atelectasis, alveolar and interstitial edema and diffuse hyaline membranes in distorted small airways. The incidence, severity and mortality associated with RDS are significantly reduced by prenatal corticosteroids and postnatal surfactant replacement therapy, and surfactant therapy has become the standard of care in management of preterm infants with RDS.

Meconium Aspiration Syndrome (MAS) is an important cause of perinatal respiratory distress with increased morbidity and mortality, and it affects an estimated 25,000 neonates in the United States each year. Fetal distress is indicated by meconium staining of the amniotic fluid or foetus. Physiologically, fetal respiration is associated with movement of fluid from the airways out into the amniotic fluid. However, fetal distress initiates aspiration of amniotic fluid and meconium into larger airways leading to gasping in utero. Meconium has been found to destroy the fibrillary structure of surfactant and decreases its surface adsorption rate. An inflammatory response characterized by the presence of elevated cell count and pro-inflammatory cytokines IL-1β, IL-6, and IL-8 has been found to be associated with MAS as early as in the first 6 hours hours of life. MAS induced acute lung injury is characterized by airway obstruction, pneumonitis, pulmonary hypertension, ventilation/perfusion mismatch, acidosis and hypoxemia. In vitro studies have demonstrated a meconium PLA2 mediated dose-dependent inhibition of surfactant activity through the competitive displacement of surfactant from the alveolar film. PLA2 is also known to damage the alveolar capillary membrane and induce intrapulmonary sequestration of neutrophils by free fatty acids and lyso-PC released by hydrolysis of DPPC. Bolus or diluted exogenous surfactant replacement has been shown to reverse hypoxemia, reduce pneumothoraces, decrease duration of oxygen therapy and mechanical ventilation, reduce duration of hospital stay, and decrease requirement for extracorporeal membrane oxygenation (ECMO). However, comparison studies, utilising various treatment regimens: standard, bronchoalveolar lavage (BAL) with diluted surfactant, or diluted surfactant BAL plus a single early dexamethasone, did not demonstrate superiority of one form of therapy over another, and may be related to the heterogeneous nature of this form of lung injury. Another randomized trial, infants receiving surfactant lavage has significant improvements in oxygenation, decreases in mean airway pressure, and arterial-alveolar oxygen tension gradients compared to bolus group. However, the study showed no significant differences in duration of nitric oxide, assisted ventilation, or hospitalization.

ARDS is defined as a severe form of acute lung injury (ALI) and a syndrome of acute pulmonary inflammation, characterised by sudden onset, impaired gas exchange, decreased static compliance, and by a non-hydrostatic pulmonary edema. The pediatric ARDS incidence is higher in high income countries. Children are particularly vulnerable in the first year of life, and infection is the most common cause of ARDS. The group principally at risk are premature neonates with chronic lung disease who develop viral pneumonia, older children with immune deficiency syndromes, and those with childhood malignancies. The hallmark of acute event is the injury to Type I alveolar cells and endothelium with increased permeability of the alveolar-capillary barrier leading to an influx of protein-rich edema-fluid into the alveoli, and decreased fluid clearance from the alveolar space. Host bacterial and chemotactic factors attract neutrophils into the airways which further damage the alveolar epithelial cells through expression of enzymes and cytokines. Injury to Type II epithelial cell leads to a decrease in surfactant production, with resultant alveolar collapse. Four clinical criteria must be met to establish a clinical diagnosis of ARDS: (i) acute disease onset, (ii) bilateral pulmonary infiltrates on chest radiograph, (iii) pulmonary capillary wedge pressure <18 mmHg or absence of clinical evidence of left atrial hypertension, and (iv), ratio between arterial oxygen partial pressure (PaO2) and the fraction of inspired oxygen (FiO2)<200. (62) In contrast, patients that meet the first three criteria, but exhibit a PaO2/FiO2 ratio between 200 and 300, are defined as having ALI. The mortality from ARDS in the pediatric age group, despite the introduction of novel treatments, still remains high. Efforts to treat with an SP-C surfactant were ineffective, and the use of calfactant (Infasurf®) in younger children with ALI was effective in reducing ventilator days and increasing survival.

The role of surfactant damage/loss in ARDS patients is recognized and surfactant replacement seems to improve clinical outcomes in pediatric primary, direct ARDS, as supported by some clinical trials. The incidence and mortality of neonatal ARDS are very similar to the pediatric one, according to preliminary data from the neonatal ARDS network.

*Bacillus anthracis*, the etiological agent of anthrax, has been developed as a bioweapon by countries and terrorists largely because of a combination of the spore's durability and the lethal toxemia of the vegetative stage. This Gram-positive bacterium forms spores resistant to adverse environmental conditions and can survive for decades in pastures. If ingested or inhaled, even in small numbers, the spores germinate to establish explosive vegetative growth and a resulting toxemia that is usually fatal to the host. The primary virulence factor is a secreted zinc-dependent metalloprotease toxin known as lethal factor (LF), which is lethal to the host through disruption of signaling pathways, cell destruction, and circulatory shock. Zinc metalloproteases are classified into five distinct family groups based on the unique signature within the amino acid sequences around HEXXH motif: thermolysin, astacin, serratia, matrixin, and reprolysin metalloproteases that include snake venom, anthrax and *E. coli* related enzymes. The latter four families have an extended zinc binding site, HEXXHXXGXXH, where the third histidine acts as the third zinc ligand instead of the more distant glutamic acid in thermolysin. Of note, the key zinc binding motif has the following: The zinc-binding motif, HEXXH (where H=his, E=glu, and x=any amino acid), found in many zinc metalloproteases, including anthrax lethal factor (LF) and rattlesnake venoms.

H E X X H—General motif for zinc binding metalloproteases

H E F G H—Conserved zinc binding site in anthrax lethal factor

H E M G H— In zinc binding rattlesnake venom metalloproteases

Thus, we used rattlesnake venom as a our model for anthrax LF. The only existing therapeutic intervention for naturally acquired or weaponized anthrax is antibiotic treatment that must be given early after infection and at a time when victims may experience only mild flu-like symptoms. Delay of treatment, even by hours, substantially reduces survival of infected patients. To date, physicians have antibiotic options to eliminate an anthrax infection, but they have no therapeutic options to combat the LF-mediated toxemia and tissue destruction during an ongoing infection or the residual toxemia that persists even after the bacteria have been eliminated by antibiotics and previous attempts to investigate hydroxamate MP inhibitors have not yielded satisfactory results despite favorable results in cell culture. *Bacillus anthracis*, the causative agent of anthrax, manifests its pathogenesis through the action of two secreted toxins. *B. anthracis* produces three proteins that make up anthrax lethal toxin (LT) and edema toxin (ET). The bipartite LT and ET, a combination of three proteins: protein protective antigen (PA), lethal factor (LF), and edema factor (EF), are important virulence factors for this bacterium. PA is a receptor-binding component common to both toxins that translocates LF (a protease) or EF (an adenylate cyclase) into cells. Immunization against PA is sufficient for protection from infection. Group IIA secreted phospholipase A2 (sPLA2-IIA) is produced in particular by macrophages and possesses potent antibacterial activity especially against Gram-positive bacteria. The investigators previously showed, in vitro, that sPLA2-IIA kills both germinated *B.*

*anthracis* spores and encapsulated bacilli. Studies have demonstrated that sPLA2-IIA might play a major role in host defense against anthrax. Conversely, this bacterium is able to disarm the host immune system, at least in part, through the inhibition of sPLA2-IIA expression by alveolar macrophages. Thus, the literature teaches away from the use of sPLA2 alone and in combination with MP inhibitors has not been contemplated in combination for the purpose of treating anthrax toxin effects. While these long peptide hydroxamates are highly potent LF inhibitors in vitro, their activity in inhibiting macrophage killing by LeTx is relatively weak, requiring μM concentrations. There is evidence to suggest that what efficacy is observed in cultured cells may be at least partly attributable to weak inhibition of furin by the polyArg sequence. Investigation has found that the hydroxamate group is susceptible to hydrolysis by prolonged incubation with LF, converting it to a weaker LF inhibitor, potentially explaining the low efficacy in cells. Thus it is surprising that the inventors found that the metalloprotease inhibitor, prinomastat, was effective in treating, by itself or in combination with AZD2716, mice given doses of LPS/Oleic Acid (LPS/OA) sufficient to induce severe, acute lung injury and ARDS with the type of histological findings and endo/epithelial type findings common in directly induced ARDS such as with aspiration syndromes and chemical irritants as well as diseases such as anthrax all which have complex interplays between metalloprotease and sPLA2 normal and dysregulated processes.

It is envisaged that, depending on how and when administered, either an LF inhibitor (LFI) could block the proteolytic protection provided by LF in the macrophage and allow that cell to eliminate spores early in infection (which could be used prophylactically if intentional release of anthrax were suspected) or, more probably, an LFI would be used to block late stage effects of LF during an active infection and increase the probability of host survival. This latter aspect would unquestionably be used in adjunct therapy with an antibiotic.

Importantly, the potential of sPLA2 inhibitors such as varespladib (LY315920), methyl-varespladib (LY333013), AZD2716-(R)-3-(5'-benzyl-2'-carbamoyl-[1,1'-biphenyl]-3-yl)-2-methylpropanoic acid—as a racemic mixture or enantiomer thereof, preferably the "R" enantiomer of the racemic mixture), compound 4 (3-(5'-benzyl-2'-carbamoyl-[1,1'-biphenyl]-3-yl)-propanoic acid) and LY433771 ((9-[(phenyl) methyl]-5-carbamoylcarbazol-4-yl}oxyacetic acid) as therapeutic agents are now supported by the present invention. Metalloproteases are also supported for use in the present invention. Metalloprotease inhibitors of importance include prinomastat, BB-94 (marimastat), BB-2516 (batimastat), vorinostat, cefixime, doxycycline, but these agents have not been recognized or realized in the treatment of these life threatening diseases, conditions or the timing of their use alone or in combinations that could prevent, mitigate and reverse conditions whose treatment could unexpectedly benefit from these compounds alone or in combination. Examples include ARDS type disease states and/or conditions ranging from neonatal to adult and for prevention and/or amelioration of lung and kidney damage from anthrax as well as for the accelerated healing of wounds and non-healing ulcers and residual toxidromes (e.g. from snakes) driven by maladaptive host responses or residual toxins.

BRIEF SUMMARY OF THE INVENTION

The present invention is directed to the use of an effective amount of at least one PLA2 inhibitor and/or at least one metalloprotease inhibitor alone or preferably in combination with at least one antibiotic to reduce the likelihood of an injured patient or subject at risk of a life threatening inflammatory syndrome becoming infected such that the infection will produce one or more of sepsis, septic shock, an acute inflammatory syndrome such as systemic inflammatory response syndrome (SIRS) and/or acute respiratory distress syndrome (ARDS). These compositions and methods are also useful in the treatment of disease states and conditions which are associated with or have secondary effects of inflammatory syndrome such as anthrax (*Bacillus anthracis*) and coronavirus (especially including Severe Acute Respiratory Syndrome coronavirus (e.g. SARS or SARS-CoV2). In embodiments, the PLA2 inhibitor is varespladib (LY315920), methyl-varespladib (LY333013), AZD2716-(R)-3-(5'-benzyl-2'-carbamoyl-[1,1'-biphenyl]-3-yl)-2-methylpropanoic acid—as a racemic mixture or a stereoisomer thereof, preferably the "R" enantiomer of the racemic mixture), compound 4 (3-(5'-benzyl-2'-carbamoyl-[1,1'-biphenyl]-3-yl)-propanoic acid) or LY433771 ((9-[(phenyl)methyl]-5-carbamoylcarbazol-4-yl}oxyacetic acid), a pharmaceutically acceptable salt thereof or a mixture thereof. In embodiments, the metalloprotease inhibitor is prinomastat, BB-94 (marimastat), BB-2516 (batimastat), vorinostat, cefixime and doxycycline, a pharmaceutically acceptable salt thereof or a mixture thereof, among others.

In an embodiment, the present invention is directed to a method of reducing the likelihood that an injured patient or subject at risk of a life-threatening inflammatory syndrome (especially including from an infection) will produce one or more of sepsis, septic shock, an acute inflammatory syndrome (whether iatrogenic or not) or acute respiratory distress syndrome, comprising administering to said patient or subject an effective amount of at least one PLA2 inhibitor and/or at least one metalloprotease inhibitor alone or in combination with at least one antibiotic. The present invention is particularly useful for treating severe injuries, and infections which can result in inflammatory syndrome, including anthrax and SARS/SARS-CoV2 infections.

In an embodiment, the present invention is directed to administering to a patient or subject who has been severely injured or burned and places that patient or subject at risk for one or more of sepsis, septic shock, slow or poor wound healing, including skin grafts, acute inflammatory syndrome, including inflammatory response syndrome (SIRS) and/or acute respiratory distress syndrome (ARDS), an effective amount of an antibiotic to treat infection in combination with an effective amount of at least one PLA2 inhibitor and/a metalloprotease inhibitor. In embodiments, the method comprises administering at least two antibiotics and at least one PLA2 inhibitor and/or at least one metalloprotease inhibitor. Pursuant to the present invention, it has been discovered that the co-administration of effective amounts of at least one antibiotic and at least one PLA2 inhibitor and/or at least metalloprotease inhibitor will provide an unexpected inhibition, amelioration or avoidance of sepsis, septic shock, acute inflammatory syndrome, including inflammatory response syndrome (SIRS) and/or acute respiratory distress syndrome (ARDS) in the patient or subject at risk. In embodiments, the PLA2 inhibitor is varespladib (LY315920), methyl varespladib (LY333013), AZD2716-(R)-3-(5'-benzyl-2'-carbamoyl-[1,1'-biphenyl]-3-yl)-2-methylpropanoic acid—(as a racemic mixture or a stereoisomer thereof, preferably the "R" enantiomer of the racemic mixture), compound 4 (3-(5'-benzyl-2'-carbamoyl-[1,1'-biphenyl]-3-yl)-propanoic acid) or LY433771 ((9-[(phenyl)methyl]-5-carbamoylcarbazol-4-yl)oxyacetic acid), a pharmaceutically acceptable salt thereof or a mixture thereof. In embodiments, the metalloprotease inhibitor is prinomastat, BB-94 (marimastat), BB-2516 (batimastat), vorinostat, cefixime and doxycycline, a pharmaceutically acceptable salt thereof or a mixture thereof, among others.

In an embodiment, the present invention is directed to treating a patient or subject with suspected sepsis, including early sepsis or other inflammatory syndrome or comprising administering to said patient or subject in need, an effective amount of at least one antibiotic and an effective amount of at least one PLA2 inhibitor and/a metalloprotease inhibitor. In embodiments, the method comprises administering at least two antibiotics and at least one PLA2 inhibitor and/or at least one metalloprotease inhibitor. Pursuant to the present invention, it has been discovered that the co-administration of effective amounts of at least one antibiotic and at least one PLA2 inhibitor and/or at least metalloprotease inhibitor will safely provide an unexpected prevention, inhibition, amelioration or avoidance of sepsis, septic shock, acute inflammatory syndrome, including inflammatory response syndrome (SIRS) and/or acute respiratory distress syndrome (ARDS) in the patient or subject at risk. In embodiments, the PLA2 inhibitor is varespladib (LY315920), methyl varespladib (LY333013), AZD2716-(R)-3-(5'-benzyl-2'-carbamoyl-[1,1'-biphenyl]-3-yl)-2-methylpropanoic acid—(as a racemic mixture or as a stereoisomer thereof, preferably as the "R" enantiomer of the racemic mixture), compound 4 (3-(5'-benzyl-2'-carbamoyl-[1,1'-biphenyl]-3-yl)-propanoic acid) or LY433771 ((9-[(phenyl)methyl]-5-carbamoylcarbazol-4-yl}oxyacetic acid), a pharmaceutically acceptable salt thereof or a mixture thereof. In embodiments, the metalloprotease inhibitor is prinomastat, BB-94 (marimastat), BB-2516 (batimastat), vorinostat, cefixime and doxycycline, a pharmaceutically acceptable salt thereof or a mixture thereof, among others.

In an embodiment, the present invention is directed to treating a patient with an anthrax or severe acute respiratory syndrome coronavirus (SARS and SARS-CoV2) infection comprising administering to said patient or subject in need, an effective amount of at least one PLA2 inhibitor and/a metalloprotease inhibitor, optionally in combination with at least one antibiotic or other therapeutic agent to reduce the likelihood of and/or ameliorate or inhibit the impact of any one or more of sepsis, septic shock, acute inflammatory syndrome, including inflammatory response syndrome (SIRS) and/or acute respiratory distress syndrome (ARDS) in the patient or subject in need.

In embodiments, the present invention is also directed to a method for preserving a blood sample(s) taken from a patient or subject who has injuries or burns which place the patient or subject at risk for one or more of sepsis, septic shock, acute inflammatory syndrome, including inflammatory response syndrome (SIRS) and/or acute respiratory distress syndrome (ARDS), the method comprising combining in said blood sample with an effective amount of at least one PLA2 inhibitor and/or at least one metalloprotease each alone, together or in combination with an effective amount of at least one antibiotic. In embodiments, the PLA2 inhibitor is varespladib (LY315920), methyl varespladib (LY333013), AZD2716-(R)-3-(5'-benzyl-2'-carbamoyl-[1,1'-biphenyl]-3-yl)-2-methylpropanoic acid—(as a racemic mixture or a stereoisomer thereof, preferably the "R" enantiomer of the racemic mixture), compound 4 (3-(5'-benzyl-2'-carbamoyl-[1,1'-biphenyl]-3-yl)-propanoic acid) or LY433771 ((9-[(phenyl)methyl]-5-carbamoylcarbazol-4-yl}oxyacetic acid), a pharmaceutically acceptable salt or mixture thereof. In embodiments, the metalloprotease inhibitor is prinomastat, BB-94 (marimastat), BB-2516 (batimastat), vorinostat, cefixime and doxycycline, a pharmaceutically acceptable salt or mixture thereof, among others.

In embodiments, the present invention is directed to a pharmaceutical composition for ameliorating, inhibiting or reducing the likelihood of one or more of sepsis, septic shock, acute inflammatory syndrome, including inflammatory response syndrome (SIRS), hemolytic uremic syndrome (HUS), and/or acute respiratory distress syndrome (ARDS) in a patient or subject in need, the composition comprising an effective amount of at least one antibiotic in combination with at least one PLA2 inhibitor and/or at least one metalloprotease inhibitor. In embodiments, the PLA2 inhibitor is varespladib (LY315920), methyl varespladib (LY333013), AZD2716-(R)-3-(5'-benzyl-2'-carbamoyl-[1,1'-biphenyl]-3-yl)-2-methylpropanoic acid—(as a racemic mixture or a stereoisomer thereof, preferably the "R" enantiomer of the racemic mixture), compound 4 (3-(5'-benzyl-2'-carbamoyl-[1,1'-biphenyl]-3-yl)-propanoic acid) or LY433771 ((9-[(phenyl)methyl]-5-carbamoylcarbazol-4-yl)oxyacetic acid), a pharmaceutically acceptable salt, a stereoisomer thereof or a mixture thereof. In embodiments, the metalloprotease inhibitor is prinomastat, BB-94 (marimastat), BB-2516 (batimastat), vorinostat, cefixime and doxycycline, a pharmaceutically acceptable salt or mixture thereof, among others. In cases associated with anthrax, the antibiotic is ciprofloxacin, levofloxacin, moxifloxacin, penicillin g, doxycycline, chloramphenicol, ofloxacin and mixtures thereof.

In embodiments, the present invention is also directed to a composition comprising a blood sample(s) taken from a patient or subject who has injuries or burns which place the patient or subject at risk for one or more of sepsis, septic shock, acute inflammatory syndrome, including inflammatory response syndrome (SIRS) and/or acute respiratory distress syndrome (ARDS) in combination with an effective amount of at least one PLA2 inhibitor and/or at least one metalloprotease each alone, together or in combination with an effective amount of at least one antibiotic. In embodiments, the PLA2 inhibitor is varespladib (LY315920), methyl varespladib (LY333013), AZD2716-(R)-3-(5'-benzyl-2'-carbamoyl-[1,1'-biphenyl]-3-yl)-2-methylpropanoic acid—(as a racemic mixture, or a stereoisomer thereof, preferably as the "R" enantiomer of the racemic mixture), compound 4 (3-(5'-benzyl-2'-carbamoyl-[1,1'-biphenyl]-3-yl)-propanoic acid) or LY433771 ((9-[(phenyl)methyl]-5-carbamoylcarbazol-4-yl}oxyacetic acid), a pharmaceutically acceptable salt, stereoisomer or mixture thereof. In embodiments, the metalloprotease inhibitor is prinomastat, BB-94 (marimastat), BB-2516 (batimastat), vorinostat, cefixime and doxycycline, a pharmaceutically acceptable salt or mixture thereof, among others.

The present invention meets a long-felt need in the art, inasmuch as the methods and compositions may be used to treat patients or subjects with severe burns or injuries (without further diagnosis) in order to substantially ameliorate, inhibit or reduce the likelihood of one or more of sepsis, septic shock, acute inflammatory syndrome, including inflammatory response syndrome (SIRS) and/or acute respiratory distress syndrome (ARDS) in a patient or subject in need.

In additional embodiments, the present invention also relates to the treatment of neonatal ARDS, including meconium aspiration syndrome (MAS) which is a life-threatening type of neonatal ARDS with high rates of mortality and no approved treatments. meconium aspiration syndrome (MAS) is known to damage surfactant. It is known that surfactant function is damaged and correlates with lung aeration and as consequence of these changes, surfactant nanostructure is also damaged. Neonatal ARDS has some shared traits with other forms of adult and pediatric ARDS and support the development of new surfactant protection and anti-inflammatory strategies such as combinations of surfactant (porcine and synthetic) or pretreatment of the patient with IV sPLA2 inhibitors such as LY315920, AZD2716 (as a racemic mixture or stereoisomer thereof, preferably the "R" enantiomer of the racemic mixture), compound 4 (3-(5'-benzyl-2'-carbamoyl-[1,1'-biphenyl]-3-yl)-propanoic acid) or mixtures thereof. Alternatively, in preferred embodiments, these drugs could be given intratracheally or via orogastric tube (LY333013, AZD2716'(as a racemic mixture or stereoisomer thereof, preferably the "R" enantiomer of the racemic mixture), compound 4 (3-(5'-benzyl-2'-carbamoyl-[1,1'-biphenyl]-3-yl)-propanoic acid) see "Compound 7" and "Compound 4" in Giordanetto et al., Med. Chem. Lett. 2016, 7, 884-889, which is incorporated by reference herein. Off target effects may be minimized by chiral separation of LY315920 or LY333013. The unique features of this strategy include the combination of reduced cytokine production and preservation of surfactant. No other drug strategy can simultaneously produce these key clinical effects in MAS or neonatal ARDS.

In addition to neonatal and pediatric application of this strategy, including dosage, forms, carriers (eg surfactant carrying sPLA2 inhibitors), all routes of delivery, timing and weight based dosing can be applied to adult patients with ARDS from any cause and in combination with antiviral, antibiotic and anticoagulants such as heparin, low-molecular weight heparin or steroids. Unlike biological response modifiers based on antibodies, synthetic small molecule inhibitors have superior tissue penetration and prevent neutrophil stiffening.

In preferred embodiments, LY315920, AZD2716, as a stereoisomer/enantiomer or racemic mixture and/or compound 4 (3-(5'-benzyl-2'-carbamoyl-[1,1'-biphenyl]-3-yl)-propanoic acid) are combined. Alternatively, in preferred embodiments, these drugs could be given intratracheally or via orogastric tube (LY333013, AZD2716 (as a racemic mixture or stereoisomer thereof, preferably the "R" enantiomer of the racemic mixture) and Compound 4 3-(5'-benzyl-2'-carbamoyl-[1,1'-biphenyl]-3-yl)-propanoic acid) see "Compound 4", "Compound 7" and "(R)-7" in Giordanetto et al, Med. Chem. Lett. 2016, 7, 884-889, provide this superior tissue penetration and shorter half-life such that risk of reactivation of tuberculosis or hepatitis is lower risk than with long half-life antibody therapies putting patients and large populations at risk for pulmonary and systemic diseases of medium term and chronic immune suppression.

In preferred embodiments, LY315920, AZD2716 (as a racemic mixture or enantiomer thereof) are combined. Alternatively, in preferred embodiments, these drugs could be given intratracheally or via orogastric tube (LY333013, AZD2716, as a racemic mixture or enantiomer thereof, preferably as the "R" enantiomer of the racemic mixture and/or 3-(5'-benzyl-2'-carbamoyl-[1,1'-biphenyl]-3-yl)-propanoic acid—also presented as "Compound 7", "Compound (R)-7" and "Compound 4" in Giordanetto et al) and have the unique feature of being a treatment for several diseases at once that affect poor populations, far forward military and expedition operations with purely military, scientific or combinations of military, scientific and civilian service in low and middle income countries.

The present invention advances the state of the art with respect to at least six concerns:

1) Timing-especially use prior to dysregulated or exogenous sPLA2 and MP activity in patients or subject for beneficial effect 2) Enhancing antibiotic effect 3) Improving flexibility of antibiotic choice/performance and fluid management 4) Prevention of CAR-T (and other cell-based therapy) inflammatory events 5) Prevention of cellular injury by endogenous and exogenous toxins such as anthrax lethal factor 6) Improvement in wound healing Inclusive and/or additional aspects and embodiments of the present invention include the following:

The use of sPLA2 inhibitors for reduction of morbidity and amplification of immune response to venom and inflammatory conditions.

In oncology and neurological and for example, parasitological disease applications, the present invention is directed to the use of LY315920, LY333013, LY433771, AZD2716 as the racemic mixture or R, S enantiomers of AZD2716 and compound 4 (3-(5'-benzyl-2'-carbamoyl-[1,1'-biphenyl]-3-yl)-propanoic acid) or their pharmaceutically acceptable salts for treatment and prevention of inflammatory syndromes and processes resulting in or from oncological, neurological or parasitic disease, including: solid or hematological oncologic processes caused or spread by direct extension, metastatis or vesicle release and transfer of genetic material causing solid or hematological tumor spread by direct extension, metastatis or vesicle release. Optionally, the treatment may include the co-administration of a metalloprotease inhibitor, often prinomastat, BB-94 (marimastat), BB-2516 (batimastat), vorinostat, cefixime or doxycycline, more often prinomastat, BB-94 (marimastat), BB-2516 (batimastat) or vorinostat.

In embodiments, the present invention is directed to enhancing the effectiveness and/or ameliorating side effects from the administration of vaccines. In particular, one or more of LY315920, LY333013, LY433771, AZD2716 as the racemic mixture or R, S enantiomers of AZD2716 and 3-(5'-benzyl-2'-carbamoyl-[1,1'-biphenyl]-3-yl)-propanoic acid (compound 4) or their pharmaceutically acceptable salts for treatment and prevention of cytokine release syndrome and other cytokine release syndromes and sPLA2 elevations resulting from immunotherapies including vaccine reactions from mRNA, antigen and deactivated viral vaccine formats and their carriers/adjuvants. Optionally, the method may include the co-administration of a metalloprotease inhibitor, often prinomastat, BB-94 (marimastat), BB-2516 (batimastat), vorinostat, cefixime or doxycycline, more often prinomastat, BB-94 (marimastat), BB-2516 (batimastat) or vorinostat.

In CAR-T and immunomodulating therapeutics, use of LY315920, LY333013, LY433771, AZD2716 as the racemic mixture or R, S enantiomers of AZD2716 and 3-(5'-benzyl-2'-carbamoyl-[1,1'-biphenyl]-3-yl)-propanoic acid (compound 4) or their pharmaceutically acceptable salts for treatment and prevention of CAR-T induced cytokine release syndrome and other cytokine release syndromes resulting from immunotherapies especially but not exclusively for oncological, neurological or parasitic disease. Optionally, the treatment may include the co-administration of a metalloprotease inhibitor, often prinomastat, BB-94 (marimastat), BB-2516 (batimastat), vorinostat, cefixime or doxycycline, more often prinomastat, BB-94 (marimastat), BB-2516 (batimastat) or vorinostat.

In veterinary applications, LY315920, LY333013, LY433771, AZD2716 and the racemic mixture or R, S enantiomers of AZD2716 or 3-(5'-benzyl-2'-carbamoyl-[1, 1'-biphenyl]-3-yl)-propanoic acid (compound 4) or their pharmaceutically acceptable salts alone or in combination with a metalloprotease inhibitor for treatment of endotoxin-induced laminitis in equines. Optionally, the treatment may include the co-administration of a metalloprotease inhibitor, often prinomastat, BB-94 (marimastat), BB-2516 (batimastat), vorinostat, cefixime or doxycycline, more often prinomastat, BB-94 (marimastat), BB-2516 (batimastat) or vorinostat.

In antivenom animal inoculation amplification (i.e. to tolerate higher doses of venom for antibody production in antivenom producing animals) LY315920, LY333013, LY433771, AZD2716 as the racemic mixture or R, S enantiomers of AZD2716 or 3-(5'-benzyl-2'-carbamoyl-[1,1'-biphenyl]-3-yl)-propanoic acid (compound 4) or their pharmaceutically acceptable salts alone or in combination with a metalloprotease inhibitor for amplification of antivenom manufacture. The method is to give sublethal doses of venom (but many times greater dose than used in standard venom-immunization for antivenom production) while treating with toxin specific inhibitors. By increasing the dose of venom inoculated into the animal, it will produce a much greater immune response to the venom, generating a higher concentration of antibodies and much more quickly than presently available through conventional methods of antivenom manufacture. Optionally, the method may include the co-administration of a metalloprotease inhibitor, often prinomastat, BB-94 (marimastat), BB-2516 (batimastat), vorinostat, cefixime or doxycycline, more often prinomastat, BB-94 (marimastat), BB-2516 (batimastat) or vorinostat.

For the treatment of neuropathic pain LY315920, LY333013, LY433771, AZD2716 as the racemic mixture or R, S enantiomers of AZD2716 or 3-(5'-benzyl-2'-carbamoyl-[1,1'-biphenyl]-3-yl)-propanoic acid (compound 4) or their pharmaceutically acceptable salts alone or in combination with a metalloprotease inhibitor, especially including for perioperative pain reduction related to axotomy. Optionally, the treatment may include the co-administration of a metalloprotease inhibitor, often prinomastat, BB-94 (marimastat), BB-2516 (batimastat), vorinostat, cefixime or doxycycline, more often prinomastat, BB-94 (marimastat), BB-2516 (batimastat) or vorinostat.

The inventors have, by surprise, enabled a key invention related to the treatment of inflammatory conditions and other conditions as described herein including for use in preventing and ameliorating inflammation associated with infection and attenuating the likelihood of sepsis in patients and as otherwise described herein.

The present invention is described in further detail in the sections which are presented herein below.

BRIEF DESCRIPTION OF THE FIGURES

FIG. 1, Table 1 Shows ARDS features and scoring system modeled to compare mouse lung injury based on American Thoracic Society (ATS) workshop report (Aeffner et al. *Tox Path*, 43:1074-1092, 2015). Exemplary slides showing features of the ATS criteria from Table 1 are presented as FIGS. 1 and 2.

FIG. 1B Shows the features of normal alveoli and alveolar pathology as summarized in Table 1 in a mouse with ARDS induced by a combination of LPS/OA FIG. 2 Shows that intranasal AZD2716 protects and reduces alveolar damage from intranasally applied LPS/OA at 24 and 48 hours. Intranasal AZD2716 protects and reduces alveolar damage from intranasally applied LPS/OA at A) 24 (N=3 mice/group) and B) 48 hours (N=2 mice/group); minimum 25 High Power Fields (HPF) per analysis. * denotes p<0.05. Based on the ATS workshop scoring system (Table 1), Intranasal AZD2716 protected Black-6 mice from combined LPS/OA-induced lung injury and ARDS. Treated animals were bright, alert and responsive compared to lethargic, tachypneic controls at 24 and 48 hours. Audio recordings of the mice at 24 hours clearly demonstrates the reduction in lung surface tension and increased lung compliance indicating preservation of lung surfactant (see below, FIG. 3).

FIG. 4, Table 2 Shows that prinomastat was superior in potency to anthrax lethal factor inhibitor. $IC_{50}$s reported as micromolar (μM) concentrations and selected as test article for subsequent studies despite good to excellent performance of marimastat and batimastat in same assays as measured by potency. Prinomastat was more potent than other hydroxamate metalloprotease inhibitors, including anthrax lethal factor inhibitor. Several venoms can cause ARDS and kidney damage with similarity in cellular changes seen in pulmonary and systemic anthrax. Zinc metalloproteases are classified into five distinct family groups based on the unique signature within the amino acid sequences around HEXXH motif: thermolysin, astacin, Serratia, matrixin, and reprolysin metalloproteases. The latter four families have an extended zinc binding site, HEXXHXXGXXH, where the third histidine acts as the third zinc ligand instead of the more distant glutamic acid in thermolysin. Further, we emphasize:

Figure 8:
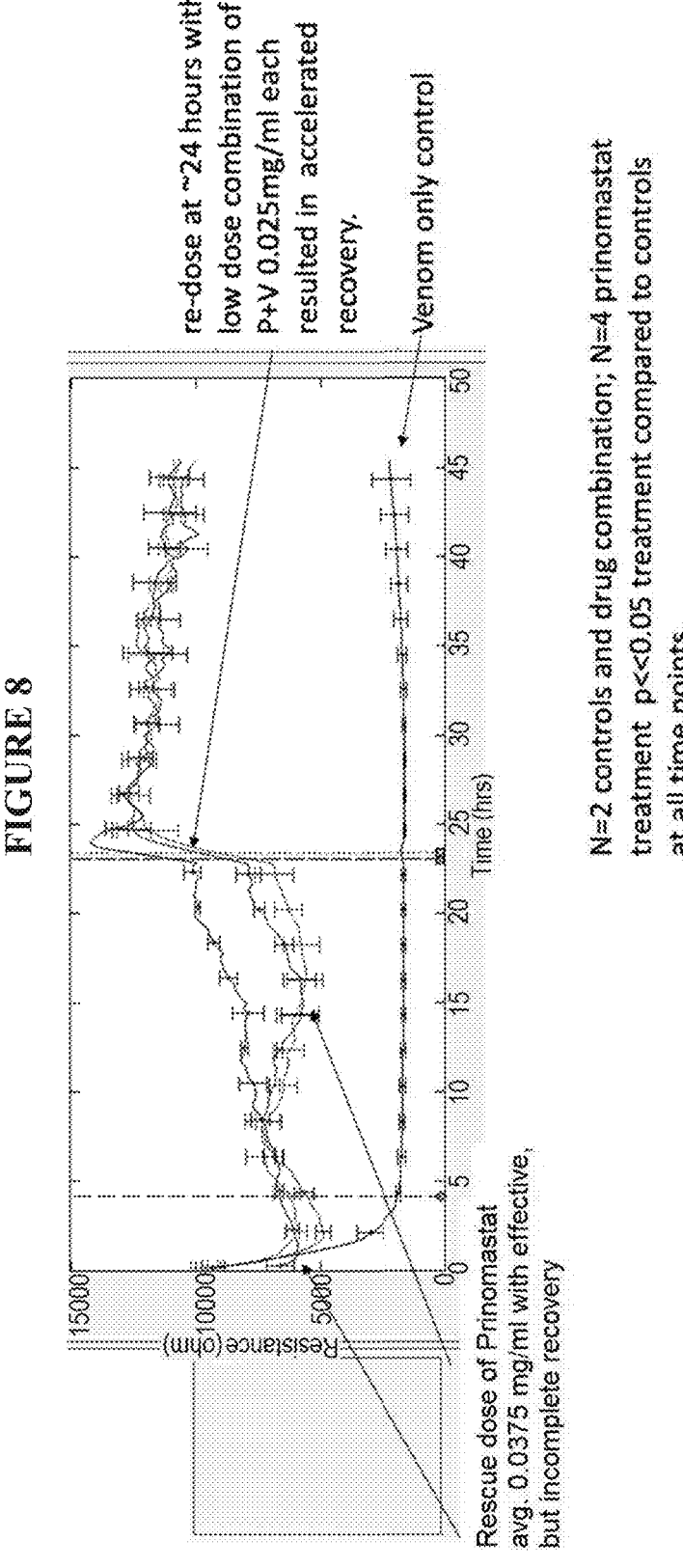

H E X X H—General motif for zinc binding metalloproteases
H E F G H—Conserved zinc binding site in anthrax lethal factor
H E M G H— In zinc binding rattlesnake venom metalloproteases Prinomastat was chosen for mouse lung-injury and ARDS study as well as in subsequent ECIS studies for this reason and to be combined with an sPLA2 inhibitor. There is no known explanation for why Prinomastat is more potent than these other inhibitors for these embodiments and it has not been contemplated as a therapeutic to combat toxin damage as seen caused by anthrax lethal factor, a toxic metalloprotease. Prinomastat has not been previously reported to be more potent than anthrax lethal factor inhibitor, but demonstrably more potent as seen in Table 2. Sistrurus venom was used as surrogate for anthrax lethal factor inhibitor because of the lethal factor inhibitor's high potency against Sistrurus venom metalloprotease activity (Table 2) which is similar to that of native anthrax lethal factor, which has also been termed "zincin" class metalloproteases (FIGS. 6, 8).

Figure 5:
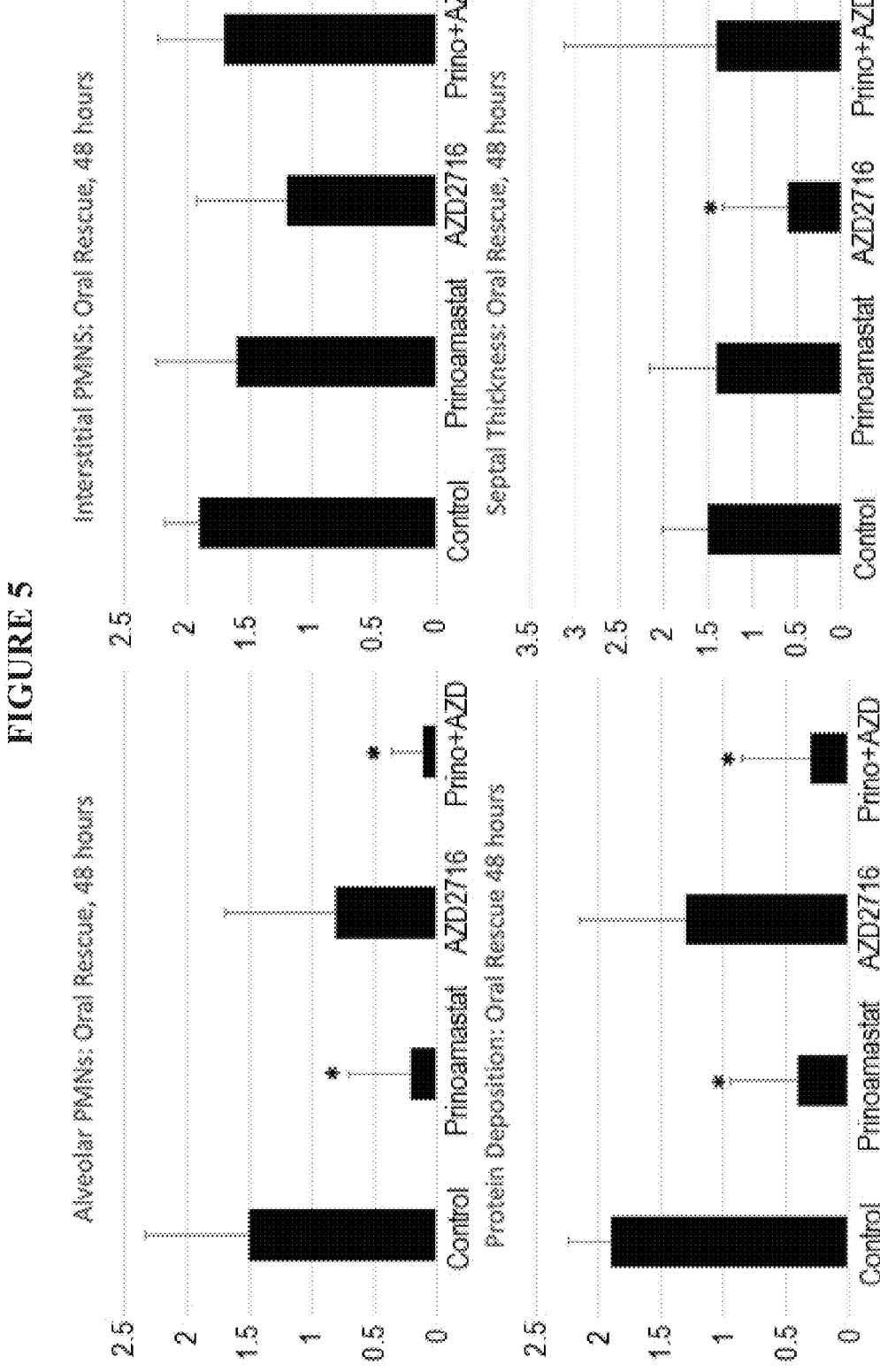

FIG. 5 Shows that both oral prinomastat and oral AZD2716 rescue and reduce damage from LPS/OA induced ARDS in mice at 48 hours. Unexpectedly, prinomastat treated mice were clinically the most bright, alert and responsive which has significant implications for the treatment of both ARDS and diseases such as anthrax. These results show the capacity of both AZD2716 and Prinomastat to improve clinical and histopathological findings when rescuing mice from LPS/OA induced ARDS. Prinomastat treated mice were, surprisingly, clinically better than AZD2716 treated mice (Prinomastat >AZD2716=Prinomastat+AZD2716 Controls) and indicates particular potential in the treatment of anthrax and other syncytia forming viral and bacterial pathogens and their elaborated toxins (e.g. anthrax lethal factor, a metalloprotease). The combination of the two drugs significantly improved the outcomes in two key components of ARDS (intra-alveolar infiltrates and protein depositions related to pulmonary edema) demonstrating the potential for these drugs alone and in combination to treat deadly conditions such as SARS-CoV-2 associated ARDS and SIRS as well as ARDS caused by anthrax bacterium, for example, that depend on both metalloproteases and sPLA2 to invade lung tissues and cause widespread inflammation (SIRS). Significant prevention of pulmonary capillary leak, inflammation, hemorrhage implies preservation of both endo- and epithelial-cell layers.

FIG. 6 Shows that venom toxins produce cellular injury and detachment quantifiable by ECIS (FIGS. 7-12) that are comparable to that found in epithelial surfaces throughout the body including kidney, lung and skin.

Figure 7:
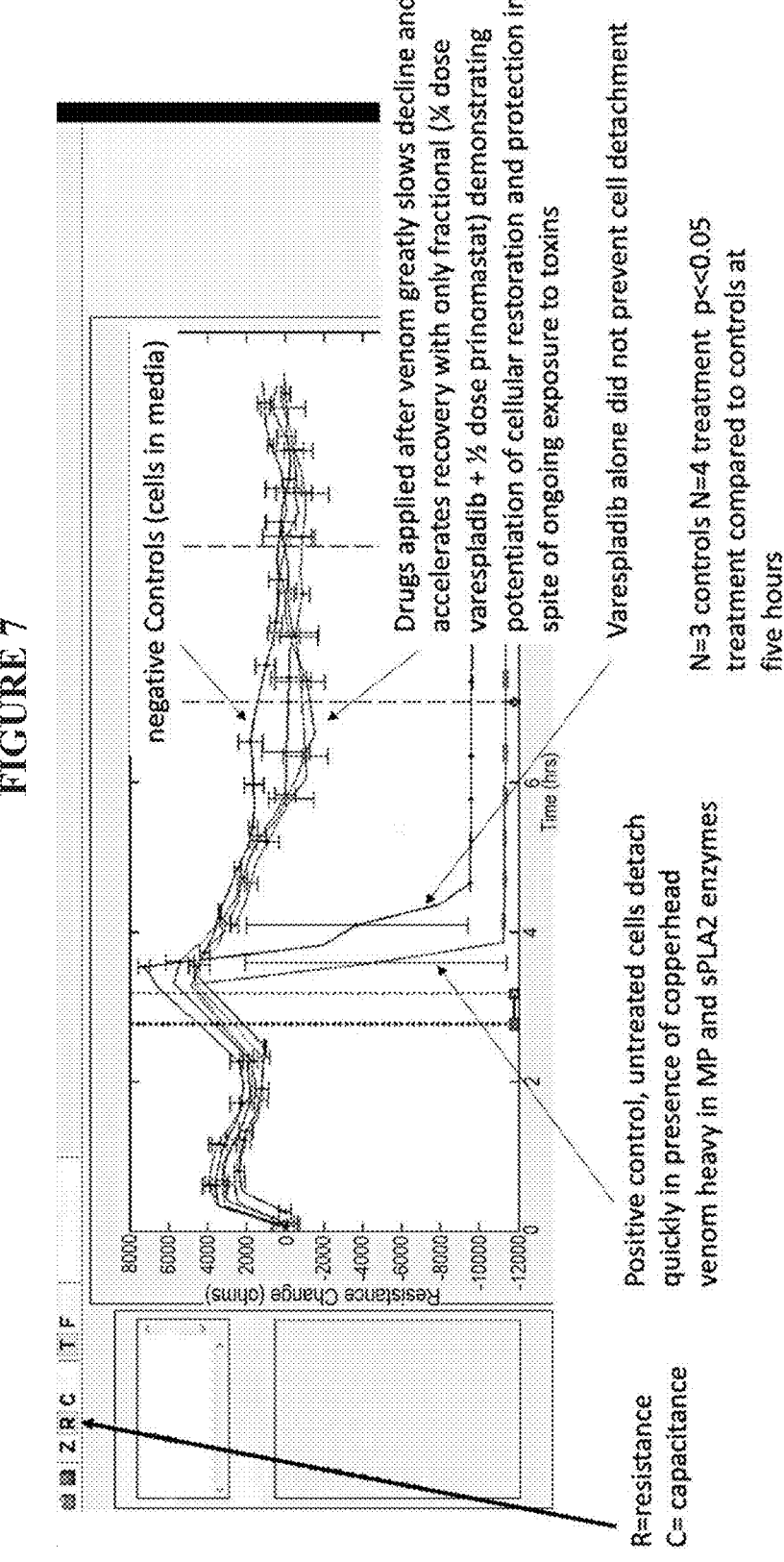

FIG. 7 Shows that rescue of epithelial cell from a balanced metalloprotease/sPLA2 containing venom (Toxin: Whole A. contortrix laticinctus venom)

FIG. 8 Shows the rescue of epithelial cell from a balanced metalloprotease/serine protease, but low sPLA2 content venom (Toxin: Whole Sistrurus venom). Sistrurus venom is used as surrogate for anthrax lethal factor and prinomastat as comparator hydroxamate inhibitor.

Figure 9:
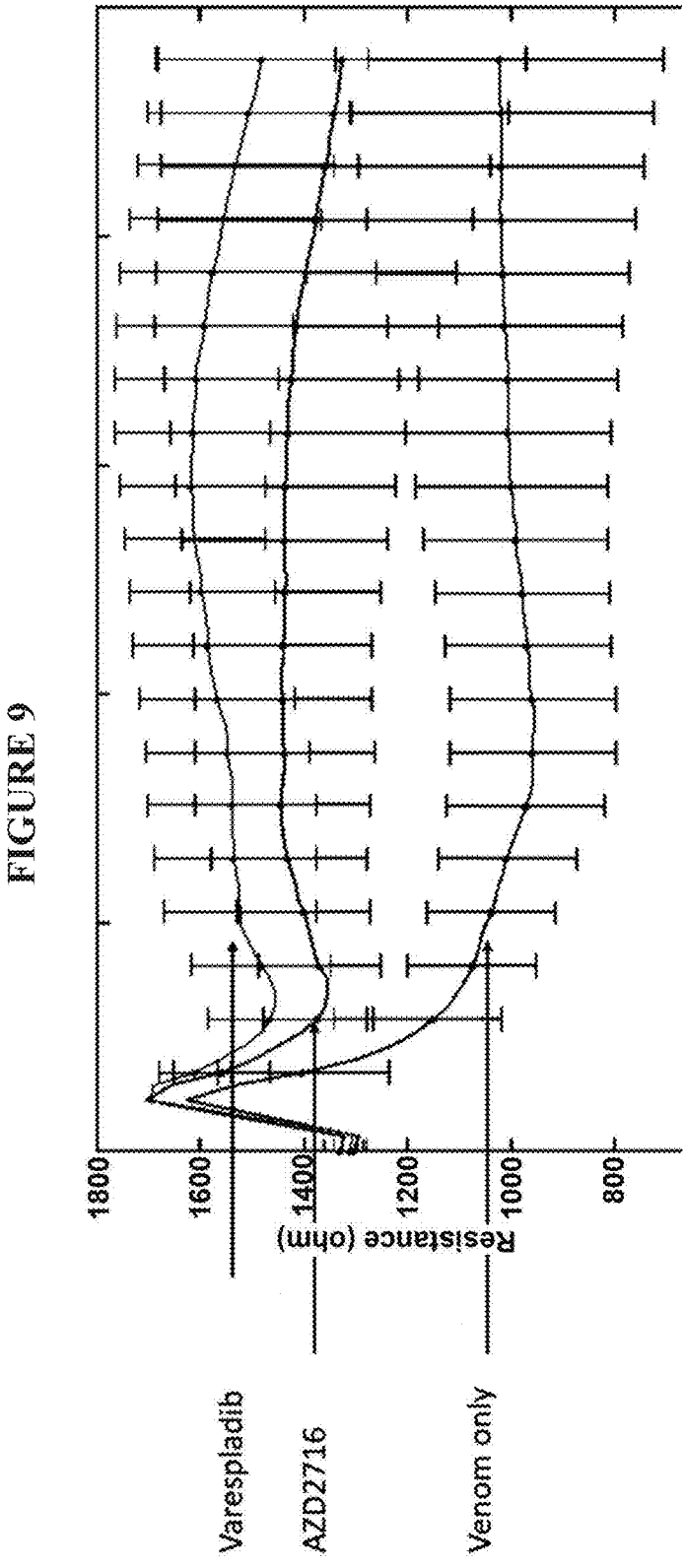

FIG. 9 Shows that AZD2716, like varespladib preserves cellular function and cell-cell junction integrity in the presence of high sPLA2 content venom toxins as measured by resistance (Toxin: C. scutulatus whole venom)

Figure 10:
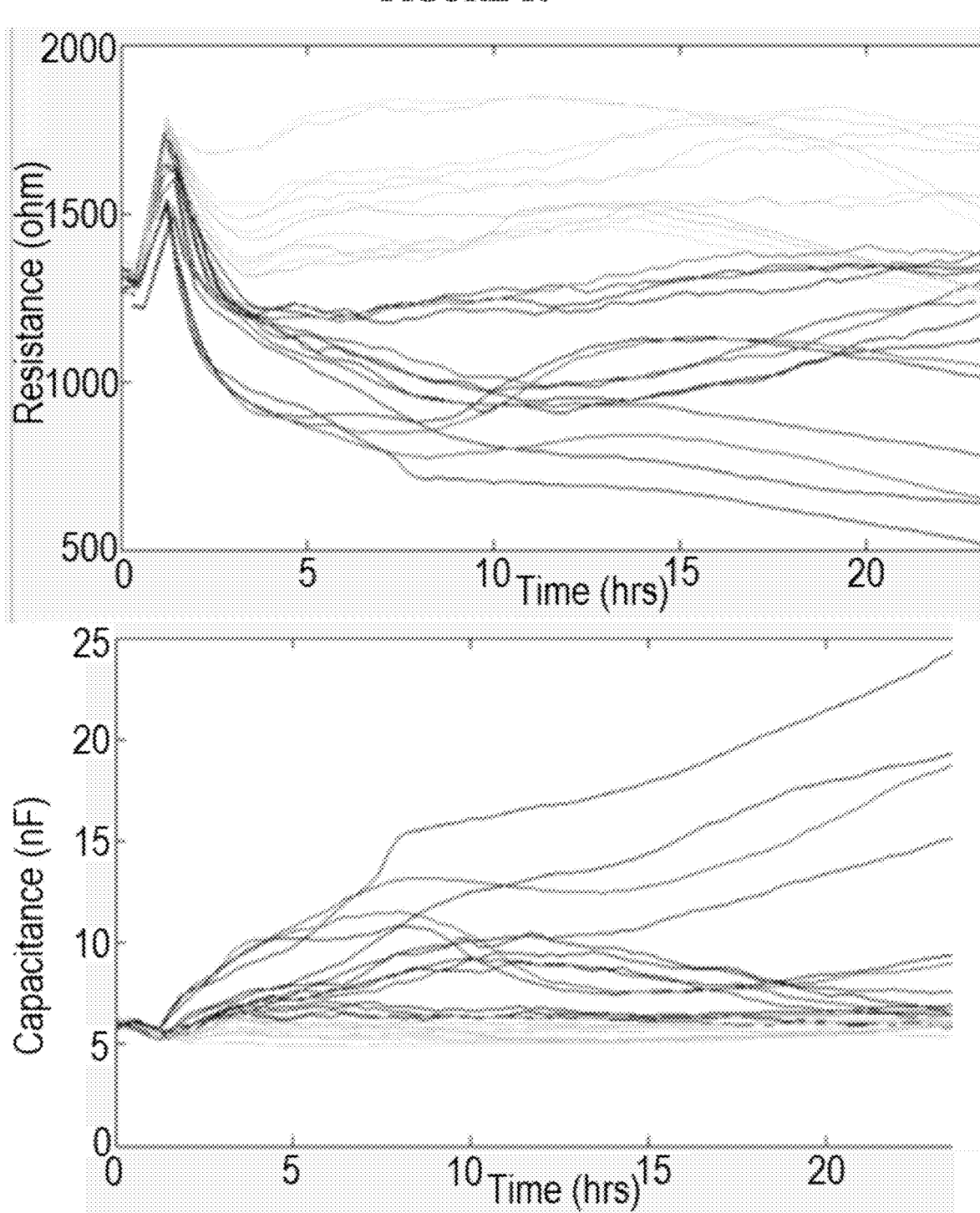
Figure 10:
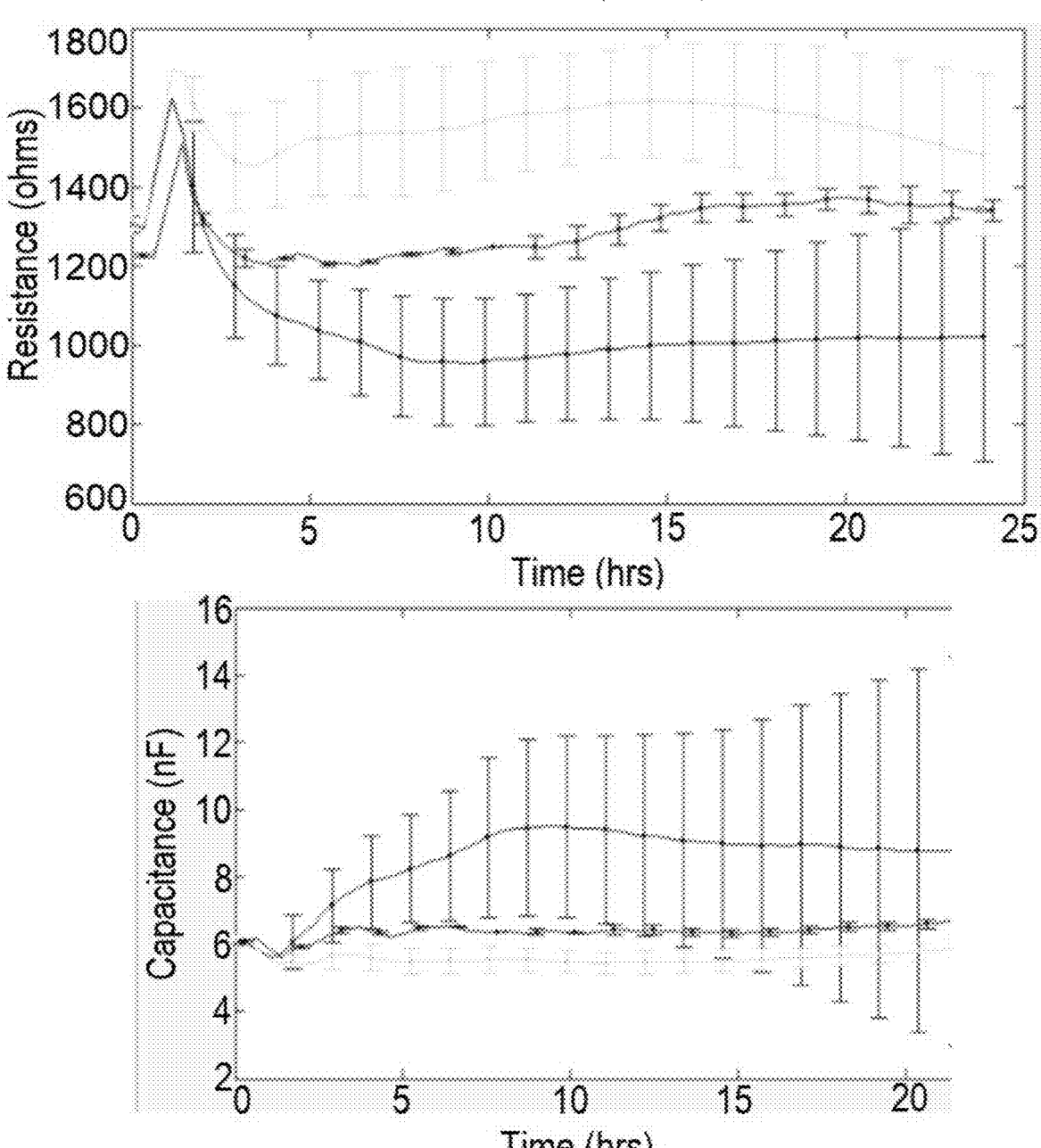

FIG. 10 Shows that varespladib, like AZD2716 in previous FIG. 9 recovers and stabilizes epithelial cells across venom genera and geography (Toxins: C. scutulatus and Daboia russelli-Pakistan). Varespladib, like AZD2716 in previous FIG. 9 recovers and stabilizes epithelial cells across venom genera and geography. As a result varespladib is shown to preserve and restore kidney function or comparable structures in other organ systems such as lung, skin, or gastrointestinal tract from insults such as viral infection, organisms like anthrax as well as venom. Top Row: Raw data shown as function of resistance and then capacitance (left to right). Bottom Row: Cumulative data showing varespladib recovers and stabilizes inter-cellular attachments (resistance) and cell viability (capacitance) left to right. C. scutulatus venom (North America), 4 doses, N=2 each; D. russelli (Pakistan variant) 2 dose concentrations, N=2 each) Varespladib: 0.05 mg/ml and 0.01 mg/mL no significant difference in response between the two doses the response was thus combined. Negative controls: N=2 kidney epithelial (vero) cells in media only.

FIG. 11 Shows that low dose prinomastat+varespladib prevents damage and accelerates wound healing in presence of rattlesnake venom containing similar enzymes responsible for chronic wounds and non-healing ulcers. Low dose prinomastat+varespladib prevents damage and accelerates wound healing in presence of rattlesnake venom containing similar enzymes responsible for chronic wounds and non-healing ulcers. Wounds produced by electrical current across all wells. +Control cells (top line): Instability of healing demonstrated by large standard deviations and increasing capacitance indicative of cell death and detachment from the basement membrane. Cells treated with lower doses of varespladib and prinomastat than normally used with either one alone produced unexpected wound healing comparable to uninjured control cells (middle and bottom, respectively). B. In presence of rapidly toxic doses of *Echis ocellatus* venom, both prinomastat and a combination of low dose prinomastat plus varespladib increase cellular junction tightness even in the ongoing presence of venom that will be useful for acute toxicity and wound healing from *Echis* species and in general healing of cellular injury. In both studies, drugs were applied following exposure to venom. Similar changes to epithelial cells are seen in ARDS and renal and pulmonary effects of infections such as those caused by anthrax via metalloprotease and/or sPLA2 mediated pathways.

Figure 12:
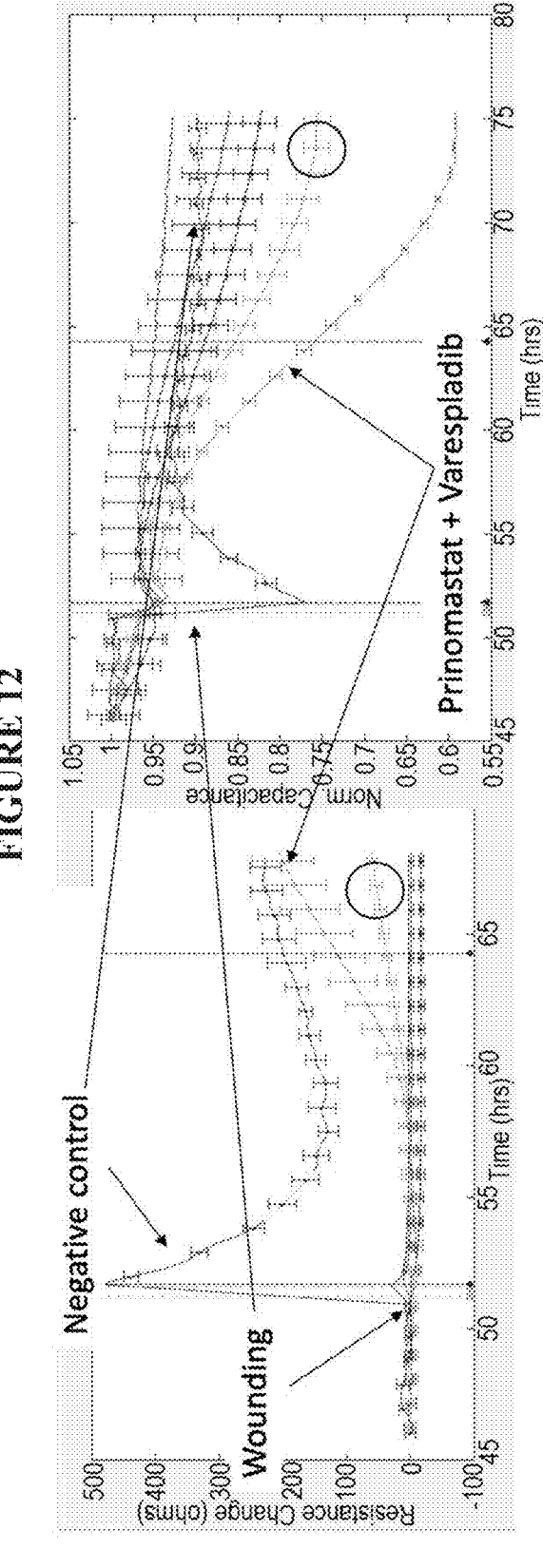

FIG. 12 Shows that low dose varespladib+prinomastat accelerate rates of wound healing even in presence of toxins (Toxin: *Sistrus miliarius barbouri*, whole venom acquired from the National Natural Toxins Research Group) even with addition of electrical wounding following exposure to venom. Cells treated with lower doses of varespladib and prinomastat than normally used with either one alone produced unexpected synergistic wound healing rates. In presence of rapidly toxic doses of *S. miliarius* venom, both prinomastat and a combination of low dose prinomastat plus varespladib increase cellular junction tightness even in the ongoing presence of venom that is a surrogate system for acute toxicity and wound healing. Similar changes to epithelial cells are seen in ARDS and renal and pulmonary effects of infections such as those caused by anthrax via metalloprotease and/or sPLA2 mediated pathways. Rates of wound healing were unexpectedly fast as demonstrated by the combination of varespladib and Prinomastat that produced A) accelerated return of cell-cell junctional tightness (resistance) as well as B) return of cellular viability. O=Prinomastat. This has broad, unexpected significance for a multitude of wound healing therapeutics.

FIG. 13 Shows the chemical structure of AZD2716, which can exist as a racemic mixture (or as an enantiomerically enriched mixture), the R enantiomer or the S enantiomer, when $R_1$ is a methyl group. This is compound 7, (S)-7 or (R)-7 of Giordanetto, cited herein which is incorporated by reference. This figure also shows the compound 3-(5'-benzyl-2'-carbamoyl-[1,1'-biphenyl]-3-yl)-propanoic acid (compound 4 of Giordanetto, cited herein), when $R_1$ is H. This compound is referred to as Compound 4 herein.

DETAILED DESCRIPTION OF THE INVENTION

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom a treatment, including prophylactic treatment (prophylaxis) is provided. For treatment of those infections, conditions or disease states which are specific for a specific animal such as a human patient, the term patient refers to that specific animal. In most instances, the patient or subject is a human patient of either or both genders.

The term "compound" is used herein to describe any specific compound or bioactive agent disclosed herein, including any and all stereoisomers (including diastereomers), individual optical isomers (enantiomers, including with respect to compound AZD2716) or racemic and enantiomerically enriched mixtures (in context, the term racemic incorporates enantiomerically enriched mixtures), pharmaceutically acceptable salts and prodrug forms. The term compound herein refers to stable compounds. Within its use in context, the term compound may refer to a single compound or a mixture of compounds as otherwise described herein.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "pharmaceutically acceptable" as used herein means that the compound, composition, including a salt form, is suitable for administration to a subject to achieve the treatments described herein, without unduly deleterious side effects in light of the severity of the disease and necessity of the treatment.

The terms "treat", "treating", and "treatment", etc., as used herein within context, also refers to any action providing a benefit to a patient at risk for any of the disease states or conditions (which can be treated pursuant to the present invention (e.g., ameliorate, inhibit, reduce the severity, cure, etc.). Treatment, as used herein, principally encompasses therapeutic treatment, but may also encompass both prophylactic and therapeutic treatment, depending on the context of the treatment. The term "prophylactic" when used in context, means to reduce the likelihood of an occurrence or in some cases, reduce the severity of an occurrence within the context of the treatment of a disease state or condition otherwise described herein.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Compounds according to the present invention may be administered with one or more additional bioactive agents to address specific disease conditions in a treated patient or subject.

The term "prevention" is used within context to mean "reducing the likelihood" of a condition or disease state from occurring as a consequence of administration or concurrent administration of one or more compounds or compositions according to the present invention, alone or in combination with another agent. Thus, the term prevention is used within the context of a qualitative measure and it is understood that the use of a compound according to the present invention to reduce the likelihood of an occurrence of a condition or disease state as otherwise described herein will not be absolute, but will reflect the ability of the compound to reduce the likelihood of the occurrence within a population of patients or subjects in need of such prevention.

The term "sepsis" is used to describe a clinical syndrome that complicates infection. It is characterized by signs of inflammation (vasodilation, leukocyte accumulation, increased microvascular permeability) occurring in tissues that are remote from the infection. Systemic inflammatory response syndrome (SIRS) is also a clinical syndrome that complicates a noninfectious insult (e.g., acute pancreatitis, pulmonary contusion). Theories about the onset and progression of sepsis and SIRS are focused on dysregulation of the inflammatory response, including the possibility that a massive and uncontrolled release of proinflammatory mediators initiates a chain of events that lead to widespread tissue injury. This response can lead to multiple organ dysfunction syndrome (MODS), which is the cause of the high mortality associated with these syndromes.

Sepsis is typically associated with a bacterial infection and is characterized by a whole-body inflammatory state (SIRS) and the presence of a known or suspected infection. The body may develop this inflammatory response by the immune system to bacteria presence in the blood, urine, lungs, skin, or other tissues. Sepsis is also referred to as "blood poisoning" or septicemia. Severe sepsis is the systemic inflammatory response, plus infection, plus the presence of at least one organ dysfunction. Septicemia (also sometimes referred to as bacteremia) refers to the presence of pathogenic organisms in the bloodstream, leading to sepsis.

Sepsis is a life-threatening condition in which the body is fighting a severe infection that has spread via the bloodstream. If a patient becomes "septic," he or she will likely have low blood pressure leading to poor circulation and lack of blood perfusion of vital tissues and organs, resulting in shock. This condition of shock is often referred to as septic shock when an infection is the cause of shock to distinguish it from shock due to blood loss or from other causes. Sepsis and septic shock can develop either as a result of the body's own defense system or from toxic substances made by the infecting agent. Survival rates for sepsis depend on the patient's underlying medical conditions, how quickly the diagnosis is made, the organism that causes the infection, and the patient's age.

In the United States, sepsis is the second-leading cause of death in non-coronary ICU patients, and the tenth-most-common cause of death overall according to data from the Centers for Disease Control and Prevention (the first being heart disease). Sepsis is common and also more dangerous in elderly, immunocompromised, and critically ill patients. It occurs in 1-2% of all hospitalizations and accounts for as much as 25% of intensive-care unit (ICU) bed utilization. It is a major cause of death in intensive-care units worldwide, with mortality rates that range from 20% for sepsis to 40% for severe sepsis to >60% for septic shock.

Septic shock is a medical emergency caused by decreased tissue perfusion and oxygen delivery as a result of severe infection and sepsis, though the microbe may be systemic or localized to a particular site. It can cause multiple organ dysfunction syndrome (formerly known as multiple organ failure) and death. Its most common victims are children, immunocompromised individuals, and the elderly, as their immune systems cannot deal with the infection as effectively as those of healthy adults. Frequently, patients suffering from septic shock are cared for in intensive care units. The mortality rate from septic shock is approximately 25/6-50% (See United States Patent Application Document No. 20140162978). Many details of optimal EGDT remain unresolved and controversial. The current invention resolves or mitigates several key elements of EGDT timing and protocol flexibility making a novel and critical advance to patient care for this long-unmet need of complex and critically ill and injured patients.

Adequate management of septic patients is often complicated by delay in administering therapy after sepsis has been recognized. Every hour delay in the administration of appropriate antibiotic therapy there is associated with a significant rise in mortality.

"Sepsis" as used herein and within context includes all of the aforementioned septic states, conditions and clinical symptoms, e.g. "sepsis" includes but is not limited to systemic inflammatory response syndrome (SIRS), septicemia and septic shock.

The term "early sepsis" is used to describe the initial stages of sepsis before a full septic state occurs. It is important to recognize the signs of early sepsis and immediately seek treatment if treatment has not yet been initiated because the infection can spread rapidly—often in a matter of hours. Sepsis occurs when an infection in the body enters the bloodstream and spreads throughout the body; this can lead to septic shock, a potentially fatal condition. Some of the earliest signs of sepsis include a high fever, a feeling of fatigue, an increased heart rate, rapid breathing or breathing difficulty. Experts generally look for at least two symptoms to suspect and diagnose sepsis. A diagnosed infection is also one of these symptoms.

If the original source of the infection is on the surface of the body, one of the best indicators of early sepsis is the presence of red streaks coming off the area and moving up the infected limb. Not all infections are superficial however, which is why the other signs of early sepsis are also important to recognize.

Infections will often present with a fever that steadily increases, but may not be evident without core temperature measurements. As the fever increases, muscle pain and weakness may become present, and some people may experience pain in the joints as well. This fever may also cause chills, and some people notice that they become dizzy and shaky, with a corresponding drop in blood pressure.

Accompanied by the chills and fever, the signs of early sepsis also often include a rapid heartbeat and quick breathing. People may find that they cannot slow the breathing or the heart rate down no matter how much they try to relax and take deep breaths. These symptoms will also worsen as the infection progresses through the body. The signs of early sepsis typically only last for a short time; if they are not addressed with emergency treatment with antibiotics, other, more serious symptoms will quickly become apparent.

Some individuals will develop a rash on the skin in addition to the red streaks. This rash can show up anywhere on the body. In addition, urine output will generally decrease significantly, which is a symptom that the organs are slowing function, which is extremely dangerous. Mental state may change as well; some people become confused and agitated. Rather than wait and see if these early symptoms of sepsis get better, it is important to receive emergency treatment as soon as possible, in this case at least one antibiotic in combination with at least one PLA2 inhibitor and/or metalloprotease inhibitor. This is another reason to be certain to care for any injuries or infections in the body, to clean cuts and scrapes well, and to take an entire course of antibiotics when prescribed, to be sure all infections are killed before they can spread.

The term "likelihood of sepsis" is used to describe a patient or subject who has extensive burns and/or a severe injury including an injury associated with an infection which likely will result in sepsis and includes any patient or subject with a several burn and/or injury which will likely result in an infection.

The term "severe burns" or "extensive burns" is used to describe a patient or subject who will likely have an infection or will result in an infection which can cause sepsis or an acute inflammatory syndromes such as systemic inflammatory response syndrome (SIRS) or related inflammatory syndrome. The severity of a burn, along with the type of burn, is important to assess before planning a burn treatment regimen and providing treatment pursuant to the present invention. Burn severity often indicates the recovery time needed and whether or not the burn patient will experience permanent effects, such as scarring or an interference or change in physiological function. More importantly, the severity of a burn may indicate that the patient or subject will become infected, thus substantially increasing the likelihood of sepsis or an acute inflammatory syndromes such as systemic inflammatory response syndrome (SIRS). Severe burns are typically classified by measuring the total body surface area (TBSA) of the burn injury. This system measures the percentage of burned skin in comparison to the rest of the victim's body. A burn injury of the same size will result in a higher TBSA for a child than for an adult, due to the child's smaller body size. The American Burn Association has set forth guidelines for measuring TBSA and diagnosing severe burns.

Burn injuries are typically placed into three major categories. In adults, burns with a TBSA of 10 percent or less are classified as minor burns. In children, minor burns measure five percent TBSA or less. Moderate burns may cover roughly ten-to-twenty percent of adults. In children, moderate burns cover roughly five-to-10 percent. Minor and moderate burns often do not produce infection consistent with eventual sepsis and/or acute inflammatory syndrome, but the patient or subject must be monitored carefully and treated pursuant to the present invention when there is evidence for risk of infection. Major, or severe burns, measure more than 20 percent TBSA in adults and more than 10 percent in children. Major or severe burns in a patient or subject are a *Prima facie* indication that the patient or subject should be treated pursuant to the present invention.

Severe burns may be caused by a number of sources, including, but not limited to thermal, e.g. hot liquids or gases, open flames and hot surfaces; chemical, e.g. strong acids or bases, such as sulfuric acid and bleach; electrical: high voltage exposure, electric arcs, and lighting; radiation: ultraviolet light, microwaves, ionizing radiation such as from x-rays or nuclear fallout. Severe burns may be accidental or intentional (especially with children and/or elders).

The term "traumatic injury" or "wound" is used to describe any injury of a severe or sufficient nature that has an identifiable risk of becoming infected or fail to heal for other reasons. Traumatic injury may refer to physical injuries of sudden onset and severity which require immediate medical attention. Initially small insults (e.g. a scratch or abrasion) as well as immediate and severe insults (e.g. motor vehicle collision or blast injury) may cause systemic shock called "shock trauma" and may require resuscitation and interventions to save life and limb. Traumatic injuries are the result of a wide variety of blunt, penetrating and burn mechanisms. They include motor vehicle collisions, sports injuries, falls, natural disasters and a multitude of other physical injuries which can occur at home, on the street, or while at work. Microscopic injuries may lead to serious injury or illness if not treated (e.g. tetanus)

With respect to major trauma, many accidents resulting in traumatic injury can be treated appropriately in hospital emergency departments. More severe and multiple traumatic injuries may be triaged by emergency responders as a Trauma Alert. A Level One Trauma Alert is a determination based on a rapid physical assessment of the victim's immediate medical needs. Based on trauma alert criteria, first responders deliver the patient to the most appropriate hospital.

Trauma guidelines in the U.S. were first established in 1976, and an efficient sophisticated trauma network now serves us all wherever we live, work or travel. Hospitals are accredited and designated as Level I, II, III or IV Trauma Centers based on the care they are able to provide, as well as the volumes they serve, urban and rural. The trauma system is designed to accommodate mass casualties and disaster situations. Level I Centers provide the highest level of care with optimal resources and capabilities, staff and specialties around-the-clock, and are continuously monitored to assure that they meet or exceed national standards. Trauma centers work closely with their respective EMS systems so that care begins pre-hospital.

Typically, critically injured patients deemed a Trauma Alert are delivered to a resuscitation area which may look more like an operating room than a traditional emergency department. In this environment, a highly-skilled professional trauma team is ready to provide immediate life-saving procedures in state-of-the-art trauma bays. Research shows that getting to the right place at the right time, commonly known as the "Golden Hour" or within the first 60 minutes after the occurrence of a major multi-system trauma, is critical. Adult and pediatric trauma surgeons, trauma staff and resources are ready and dedicated 24/7 to provide this unique level of response so that critically injured patients will have the best possible chance of survival and the least residual disability from their injuries.

Following care in the trauma resuscitation area at a Level One facility, patients may proceed to surgery, an intensive care unit or the trauma nursing floor, with all the resources and services of the hospital available in a true multidisciplinary fashion. Patients brought to Level II-IV centers may remain at that hospital or be transferred to a higher level of care as appropriate.

Some common types of traumatic injuries include, but are not limited to traumatic brain injury, spinal cord injury, spinal fractures, amputations, facial trauma, acoustic trauma, concussions, crush injuries, broken bone injury, broken jaw, skull fracture, cuts, puncture wounds, lacerations, collapsed lung, burns, myocardial contusions, electrical injuries, hypovolemic shock, subarachnoid hemorrhage and subdural hematoma, among others.

The Injury Severity Score (ISS) is an established medical score to assess trauma severity. It correlates with mortality, morbidity and hospitalization time after trauma. It is used to define the term major trauma. The ISS classifies each injury in every body region according to its relative severity on a six point ordinal scale, e.g. minor, moderate, serious, severe, critical, Maximal in six body regions, e.g. head/neck, face, thorax, abdomen/pelvis, external.

The term "systemic inflammatory response syndrome" or "SIRS" is used to describe an inflammatory syndrome which is caused by systemic response of the body due to severe inflammation or infection. This is characterized with high fever and rapid heartbeat and abnormal level of white blood cells in blood. The symptoms of SIRS vary widely depending on the triggering factor for the response and the victim's underlying predispositions. Some of the common signs include high fever, chills and localized pain based on inflammation. Some of the criteria for diagnosing SIRS including the following:

Very high or very low level of white blood cells in blood. It may go up to 12,000 per liter or below 4,000 also.

High fever and chills. The temperature may shoot up to 100.4 F or can go below 96 F also.

Rapid heartbeat and

Fast respiratory rate.

SIRS can be caused by severe infection, ischemia or after effects of surgery. Infection can occur due to bacteria, virus and other microorganisms (fungi or parasites). It can be anything ranging from sepsis, cellulitis to diabetic foot infection. SIRS can develop due to non-infectious conditions like dehydration, burns, cirrhosis, autoimmune disorders, immune therapies, acute ischemia, and myocardial infarction and due to hemorrhagic shock. In rare cases, SIRS can cause potential complications like hemolytic uremic syndrome (HUS), anemia, renal failure, respiratory failure, gastritis and abnormal levels of electrolytes.

The method of treatment for SIRS is based on symptoms and health condition of the patient. Some patients may show signs of sepsis due to severe rate of infection without having any sign of SIRS. In case of myocardial infarction or respiratory failure emergency treatment may be given on ICU, if available.

Blood pressure of the patient may be restored to normal by injecting vasopressor or similar drugs intravenously. If SIRS has developed due to surgical conditions like cholecystitis or ruptured appendix suitable surgical measures are initiated. Antibiotics are given if the root cause of infection is bacteria. Similarly antiviral medications are injected through vein if the doctor confirms the cause is viral infection. In the present invention, these agents are combined with PLA2 and/or metalloprotease inhibitors in treating SIRS. Blood glucose level is monitored carefully and if required, insulin therapy is given to stabilize the level of blood glucose.

In the present invention, the administration of at least one antibiotic in combination with at least one PLA2 inhibitor and/or at least one metalloprotease inhibitor is used to reduce the likelihood that a patient suffering a severe injury or burn will contract an infection which will develop into sepsis, septic shock, acute inflammatory syndrome, including systemic inflammatory response syndrome (SIRS) and/or acute respiratory distress syndrome (ARDS), as described herein.

Antibiotics which may be used in the present invention include, for example, broad-spectrum antibiotics such as a broad spectrum β-lactam antibiotic or a broad-spectrum carbapenem, or a mixture thereof, which can be used alone or combined with fluoroquinolones, macrolides, or aminoglycosides. In general, a combination of antibiotics may not be recommended for the treatment of sepsis but without shock and immunocompromised persons unless the combination is used to broaden the anti-bacterial activity. The choice of antibiotics is important in controlling infection, sepsis and ultimately determining the survival of the patient. It is often recommended that antibiotics are commenced within about an hour of making the diagnosis (e.g. within 10 minutes, 15 minutes, 20 minutes, 30 minutes, 40 minutes, 45 minutes, 50 minutes, 60 minutes, 75 minutes or 90 minutes), although the times can be slightly longer. In some embodiments, antibiotics and PLA2 inhibitors and/or metalloprotease inhibitors are initiated immediately or as soon as the severity of a burn or injury is assessed in a patient or subject.

For severe sepsis and septic shock a broad spectrum antibiotic (often two such antibiotics) are administered intravenously or intravenously and orally to the patient or subject in combination with the PLA2 inhibitor and/or metalloprotease at the first indication that the patient or subject has sepsis, including early sepsis. The antibiotics may include, for example a β-lactam antibiotic with broad coverage such as broad spectrum penicillin derivatives (penams) amoxicillin and ampicillin, carboxylpenicillins (e.g. carbenicillin and ticarcillin), cephalosporins (cephems) such as cefixime, doxycycline, cefotaxime, cefpodoxime, ceftazidime, ceftriaxone, cefdinir, ceftaroline fosnir all of which are broad spectrum, monobactams (e.g. aztreonam, tigemonam, carumonam and nocardicin A) and carbapenems (e.g. doripenem, faropenem, imipenem, meropenem, ertapenem, panipenim, razupenem, tebipenem, thienamycin or cilastatin/imipenem), a fluoroqunoline (e.g. ciprofloxacin, levofloxacin, fleroxacin, lomefloxacin, nadifloxacin, norfloxacin, ofloxacin, perfloxacin, rufloxacin, balofloxacin, grepafloxacin, pazufloxacin, sparfloxacin, temafloxacin, garenoxacin, gatifloxacin, gemifloxacin, moxifloxacin, clinafloxacin, sitafloxacin, prulifloxacin, besifloxacin, delafloxacin and ozenoxacin, among others), a macrolide (e.g. (e.g., azithromycin, clarithromycin, erythromycin, fiaxomycin, telithromycin, carbomycin A, josamycin A, kitasamycin, midecamycin/midecamycin acetate, oleandomycin, solithromycin, spiramycin, troleandomycin and roxithromycin, related ketolides inclouding telithromycin, cethromycin and solithromycin), each of which may be used alone or in combination.

In the case of anthrax, preferred antibiotics include ciprofloxacin, levofloxacin, moxifloxacin, penicillin G, doxycycline, chloramphenicol, ofloxacin and mixtures thereof.

"PLA2 Inhibitors" which term includes secretory Phospholipase A2 inhibitors and Phospholipase A2 (PLA2)

inhibitors are inhibitors of lipase enzymes that catalyze the hydrolysis of phospholipids at the sn-2 position yielding a free fatty acid and a lysophospholipid. $PLA_2$ contributes towards release and/or formation of at least three important lipid mediators from membrane-arachidonic acid, platelet activating factor and lysophosphatidic acid. The release of arachidonic acid from membrane phospholipids by PLA is believed to be a key step in the control of eicosanoid production within the cell. $PLA_2$ enzymes are usually grouped into cytosolic $PLA_2$ ($cPLA_2$), secretory $PLA_2$ ($sPLA2$) and calcium independent $PLA_2$ ($iPLA2$). Venom (e.g., snake venom) PLA2 are secreted (i.e., sPLA2s). Classification is based on molecular weight, calcium requirement, structural features, substrate specificity and functional role. See Ray, et al., "Phospholipase $A_2$ in Airway Disease: Target for Drug Discovery," *Journal of Drug Discovery and Therapeutics* 1 (8) 2013, 28-40.

Inhibitors of PLA2 have been identified in various sources and have been investigated as potential therapeutic agents for treatment of inflammatory diseases. See, Magrioti, Victoria, and George Kokotos. "Phospholipase A2 inhibitors as potential therapeutic agents for the treatment of inflammatory diseases." *Expert opinion on therapeutic patents* 20.1 (2010): 1-18), and Dennis, Edward A., et al. "Phospholipase A2 enzymes: physical structure, biological function, disease implication, chemical inhibition, and therapeutic intervention." sPLA2 inhibitors which can be used in the invention include, but are not limited to, LY315920 and S5920 (varespladib), LY333013 and S-3013, AZD2716-(R)-3-(5'-benzyl-2'-carbamoyl-[1,1'-biphenyl]-3-yl)-2-methylpropanoic acid—as a racemic mixture), compound 4-(3-(5'-benzyl-2'-carbamoyl-[1,1'-biphenyl]-3-yl)-propanoic acid) and LY433771 ((9-[(phenyl)methyl]-5-carbamoylcarbazol-4-yl}oxyacetic acid), LY 311727, BMS 181162, YM 26567, Variabilin, SB 203347, S-2474 (methyl indoxam) and Indoxam. In some embodiments the $PLA_2$ inhibitor(s) is varespladib and/or methylvarespladib.

Other PLA2 inhibitors, such as but not limited to other 1H-indole-3-glyoxylamides, are also useful in treatment of envenoming. One of ordinary skill in the art guided by the present disclosure will be able to identify PLA2 inhibitors and therapeutic combinations effective against a broad spectrum of venoms and/or tailored to a particular subset of venoms (e.g., particular species of snake, or venoms from particular types of invertebrates, for example).

Additional preferred sPLA2 inhibitors include those described in U.S. Pat. No. 5,654,326 (which is incorporated by reference in its entirety herein)—represented by compounds according to the chemical structure:

where X is O or S, preferably 0;

$R_1$ is $C_7$-$C_{20}$ alkyl, $C_7$-$C_{20}$ alkenyl, $C_7$-$C_{20}$ alkynyl, a carbocyclic radical (preferably a benzyl or ethylphenyl group) or a heterocyclic radical;

$R_2$ is hydrogen, halo (F, Cl, Br, I), $C_1$-$C_3$ alkyl (preferably ethyl) or $C_3$-$C_4$ cycloalkyl;

$R_4$ is H or an —O—$(CH_2)_m$—C(O)ORv group, where m is 1-3 (preferably 1) and Rv is H or a $C_1$-$C_3$ alkyl group, preferably $CH_3$; and $R_5$, $R_6$ and $R_7$ are H, or a pharmaceutically acceptable salt, solvate or polymorph thereof.

Certain preferred sPLA2 inhibitor compounds (varespladib and methylvarespladib) for use in the present invention are represented by the chemical structure:

where Rv is H (varespladib) or methyl (methylvarespladib), or their pharmaceutically acceptable salts. The above compounds also may be used as prodrug forms $C_1$-$C_6$ alkyl esters, $C_2$-$C_7$ acyloxyalkyl esters, or $C_3$-$C_9$ alkyloxycarbonyloxyalkyl esters (each formed at $R_4$). These and other related compounds for use in the present invention are described in U.S. Pat. No. 5,654,326 to Bach, et al., which is incorporated by reference in its entirety herein.

Additional $PLA_2$ inhibitors include for example: Varespladib Mofetil, N-Acetyl Cysteine, LY329722 (sodium [3-aminooxyalyl-1-benzyl-2-ethyl-6-methyl-1H-indol-4-yloxy]-acetic acid), ochnaflavone (a naturally occurring biflavonoid), BPPA (5-(4-benzyloxyphenyl)-4S-(7-phenyl-hepatonoylamino) pentanoic acid, and p-bromophenacyl-bromide (p-BPB) and other benzophenone oximes derivatized with syndone.

In certain embodiments, sPLA2 inhibitors for use in the current invention are selected from the group consisting of: {9-[(phenyl)methyl]-5-carbamoylcarbazol-4-yl}oxyacetic acid; θ-benzyl-δJ-dimethoxy-S-tetrahydrocarbazole-carboxylic acid hydrazide; 9-benzyl-5,7-dimethoxy-1,2,3,4-tetrahydrocarbazole-4-carboxamide; [9-benzyl-4-carbamoyl-7-methoxy-1,2,3,4-tetrahydrocarbazol-5-yl]oxyacetic acid; [9-benzyl-4-carbamoyl-7-methoxycarbazol-5-yl]oxyacetic acid; methyl [9-benzyl-4-carbamoyl-7-methoxycarbazol-5-yl]oxyacetic acid; 9-benzyl-7-methoxy-5-cyanomethyloxy-S-tetrahydrocarbazole-carboxamide; 9-benzyl-7-methoxy-5-(1H-tetrazol-5-yl-methyl)oxy)-1,2,3,4-tetrahydrocarbazole-4-carboxamide; {9-[(phenyl)methyl]-5-carbamoyl-2-methyl-carbazol-4-yl}oxyacetic acid; {9-[(3-fluorophenyl)methyl]-5-carbamoyl-2-methylcarbazol-4-yl}oxyacetic acid; {9-[(3-methylphenyl)methyl]-5-carbamoyl-2-methylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido)ethyloxy-2-methoxycarbazole-5-carboxamide; 9-benzyl-5-methanesulfonamidoylmethyloxy-7-methoxy-1,2,3,4- tetrahydrocarbazole-4-carboxamide; 9-benzyl-4-methanesulfonamidoylmethyloxy-carbazole-5-carboxamide; [5-carbamoyl-2-pentyl-9-(phenylmethyl)carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethylJsilyOoxymethyllcarbazol^-ylloxyacetic acid: [5-carbamoyl-2-phenyl-9-(phenylmethyl)carbazol-4-yl]oxyacetic acid; [5-carbamoyl-2-(4-chlorophenyl)-9-(phenylmethyl)carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethylJsilyOoxymethyllcarbazol^-ylloxyacetic acid; {9-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl}oxyacetic acid; {9-[(1-naphthyljmethyll-δ-carbamoylcarbazol^-yl}oxyacetic acid; {9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(3,5-dimethylphenyl)methyl]-5-carbannoylcarbazol-4-yl}oxyacetic acid; {9-[(3-iodophenyl)methyl]-5-carbannoylcarbazol-4-yl}oxyacetic acid; {9-[(2-Chlorophenyl)methyl]-5-carbannoylcarbazol-4-yl)oxyacetic acid; (9-[(2,3-difluorophenyl)methyl]-5-carbannoylcarbazol-4-yl}oxyacetic acid; {9-[(2,6-difluorophenyl)methyl]-5-carbannoylcarbazol-4-yl}oxyacetic acid; {9-[(2,6-dichlorophenyl)methyl]-5-carbannoylcarbazol-4-yl}oxyacetic acid; {9-[(2-biphenyl)methyl]-5-carbanoylcarbazol-4-yl}oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazol-5-yl]oxyacetic acid; {9-[(2-Pyridyl)methyl]-5-carbamoylcarbazol-4-yl}oxyacetic acid; {9-[(3-Pyridyl)methyl]-5-carbannoylcarbazol-4-yl}oxyacetic acid; [9-benzyl-4-carbamoyl-8-methyl-1,2,3,4-tetrahydrocarbazol-5-yl]oxyacetic acid; [9-benzyl-5-carbamoyl-1-methylcarbazol-4-yl]oxyacetic acid; [9-benzyl-4-carbamoyl-8-fluoro-1,2,3,4-tetrahydrocarbazol-5-yl]oxyacetic acid; [9-benzyl-4-carbamoyl-8-chloro-1,2,3,4-tetrahydrocarbazol-5-yl]oxyacetic acid; [5-carbamoyl-9-(phenylmethyl)-2-[[(propen-3-yl)oxy]methyl]carbazol-4-yl]oxyacetic acid; [5-carbamoyl-9-(phenylmethyl)-2-[(propyloxyjmethyllcarbazolylloxyacetic acid; 9-benzyl-7-methoxy-5-((carboxamidomethyloxy-tetrahydrocarbazole-carboxannide; 9-benzyl-7-methoxy-S-cyanomethyloxy-carbazole-carboxannide; 9-benzyl-7-methoxy-5-((1H-tetrazol-5-yl-methyl)oxy)-carbazole-4-carboxannide; 9-benzyl-7-methoxy-5-((carboxamidomethyl)oxy)-carbazole-4-carboxamide; [9-Benzyl-4-carbamoyl-1,2,3,4-tetrahydrocarbazol-5-yl]oxyacetic acid; {9-[(phenyl)methyl]-5-carbannoyl-2-methyl-carbazol-4-yl}oxyacetic acid; {9-[(3-fluorophenyl)methyl]-5-carbannoyl-2-methylcarbazol-4-yl}oxyacetic acid; {9-[(3-methylphenyl)methyl]-5-carbannoyl-2-methylcarbazol-4-yl}oxyacetic acid; {9-[(phenyl)methyl]-5-carbamoyl-2-(4-trifluoromethylphenyl)-carbazol-4-yl}oxyacetic acid; 9-benzyl-5-(2-methanesulfonamido)ethyloxy-7-methoxy-1,2,3,4-tetrahydrocarbazole-4-carboxamide; 9-benzyl-4-(2-methanesulfonamido)ethyloxy-2-methoxycarbazole-5-carboxamide; 9-benzyl-4-(2-trifluoromethanesulfonamido)ethyloxy-2-methoxycarbazole-5-carboxamide; 9-benzyl-5-methanesulfonamidoylmethyloxy-7-methoxy-1,2,3,4-tetrahydrocarbazole-4-carboxamide; 9-benzyl-4-methanesulfonamidoylmethyloxy-carbazole-5-carboxamide; [5-carbamoyl-2-pentyl-9-(phenylmethyl)carbazol-4-yl]oxyacetic acid; [5-carbamoyl-2-(1-methylethyl)-9-(phenylmethyl)carbazol-4-yl]oxyacetic acid; [5-carbamoyl-9-(phenylmethyl)-2-[(tri(-1-methylethylJsilyOoxymethyllcarbazolyloxyacetic acid; [5-carbamoyl-2-phenyl-9-(phenylmethyl)carbazol-4-yl]oxyacetic acid; [5-carbamoyl-2-(4-chlorophenyl)-9-(phenylmethyl)carbazol-4-yl]oxyacetic acid; [5-carbamoyl-2-(2-furyl)-9-(phenylmethyl)carbazol-4-yl]oxyacetic acid; [5-carbamoyl-9-(phenylmethyl)-2-[(tri(-1-methylethylJsilyOoxymethyllcarbazol-ylloxyacetic acid; {9-[(3-fluorophenyl)methyl]-5-carbamoylcarbazol-4-yl) oxyacetic acid; {9-[(3-chlorophenyl)methyl]-5-carbamoylcarbazol-4-yl}oxyacetic acid; {9-[(3-phenoxyphenyl)methyl]-5-carbamoylcarbazol-4-yl}oxyacetic acid; 19-[(2-Fluorophenyl)methyl]-5-carbamoylcarbazol-4-yl}oxyacetic acid; {9-[(2-trifluoromethylphenyl)methyl]-5-carbamoylcarbazol-4-yl}oxyacetic acid; {9-[(2-benzylphenyl)methyl]-5-carbamoylcarbazol-4-yl; oxyacetic acid; (9-[(3-trifluoromethylphenyl)methyl]-5-carbamoylcarbazol-4-yl) oxyacetic acid; {9-[(1-naphthyljmethyll-δ-carbamoylcarbazol-yl}oxyacetic acid; (9-[(2-cyanophenyl)methyl]-5-carbamoylcarbazol-4-yl}oxyacetic acid; {9-[(3-cyanophenyl)methyl]-5-carbamoylcarbazol-4-yl}oxyacetic acid; {9-[(2-methylphenyl)methyl]-5-carbannoylcarbazol-4-yl}oxyacetic acid; {9-[(3-methylphenyl)methyl]-5-carbannoylcarbazol-4-yl}oxyacetic acid; {9-[(3,5-dimethylphenyl)methyl]-5-carbannoylcarbazol-4-yl}oxyacetic acid; {9-[(3-iodophenyl)methyl]-5-carbannoylcarbazol-4-yl}oxyacetic acid; {9-[(2-Chlorophenyl)methyl]-5-carbannoylcarbazol-4-yl}oxyacetic acid; {9-[(2,3-difluorophenyl)methyl]-5-carbannoylcarbazol-4-yl}oxyacetic acid; {9-[(2,6-difluorophenyl)methyl]-5-carbannoylcarbazol-4-yl}oxyacetic acid; {9-[(2,6-dichlorophenyl)methyl]-5-carbannoylcarbazol-4-yl}oxyacetic acid; {9-[(3-trifluoromethoxyphenyl)methyl]-5-carbannoylcarbazol-4-yl}oxyacetic acid; 19-[(2-biphenyl)methyl]-5-carbannoylcarbazol-4-yl)oxyacetic acid; {9-[(2-Biphenyl)methyl]-5-carbamoylcarbazol-4-yl}oxyacetic acid methyl ester; [9-Benzyl-4-carbamoyl-1,2,3,4-tetrahydrocarbazole-5-yl]oxyacetic acid; {9-[(2-Pyridyl)methyl]-5-carbamoylcarbazol-4-yl}oxyacetic acid; {9-[(3-Pyridyl)methyl]-5-carbannoylcarbazol-4-yl}oxyacetic acid; [9-benzyl-4-carbamoyl-8-methyl-1,2,3,4-tetrahydrocarbazol-5-yl]oxyacetic acid; [9-benzyl-5-carbamoyl-1-methylcarbazol-4-yl]oxyacetic acid; [0-benzyl^-carbamoyl-δ-fluoro-1,2,3,4-tetrahydrocarbazol-5-yl]oxyacetic acid; [0-benzyl-δ-carbannoyl-1-fluorocarbazol-4-yl]oxyacetic acid; [9-benzyl-4-carbamoyl-8-chloro-1,2,3,4-tetrahydrocarbazol-5-yl]oxyacetic acid; [9-benzyl-5-carbamoyl-1-chlorocarbazol-4-yl]oxyacetic acid; [9-[(Cyclohexyl)methyl]-5-carbannoylcarbazol-4-yl]oxyacetic acid; 9-[(Cyclopentyl)methyl]-5-carbamoylcarbazol-4-yl]oxyacetic acid; [5-carbamoyl-9-(phenylmethyl)-2-(2-thienyl)carbazol-4-yl]oxyacetic acid; [5-carbamoyl-9-(phenylmethyl)-2-[[(propen-3-yl)oxy]methyl]carbazol-4-yl]oxyacetic acid; [5-carbamoyl-9-(phenylmethyl)-2-[(propyloxyjmethyllcarbazol-ylloxyacetic acid; 9-benzyl-7-methoxy-5-((carboxamidomethyloxy-tetrahydrocarbazole-carboxamide; 9-benzyl-7-methoxy-δ-cyanomethyloxy-carbazole-carboxamide; 9-benzyl-7-methoxy-5-((1H-tetrazol-5-yl-methyl)oxy)-carbazole-4-carboxamide; 9-benzyl-7-methoxy-5-((carboxamidomethyl)oxy)-carbazole-4-carboxamide; [9-Benzyl-4-carbamoyl-1,2,3,4-tetrahydrocarbazole-5-yl]oxyacetic acid; (R,S)-(9-benzyl-4-carbamoyl-1-oxo-3-thia-1,2,3,4-tetrahydrocarbazol-5-yl)oxyacetic acid; (R,S)-(9-benzyl-4-carbamoyl-3-thia-1,2,3,4-tetrahydrocarbazol-5-yl)oxyacetic acid; 2-(4-oxo-5-carboxamido-9-benzyl-9/-/-pyrido[3,4-ib]indolyl)acetic acid chloride; [N-benzyl-1-carbamoyl-1-aza-1,2,3,4-tetrahydrocarbazol-8-yl]oxyacetic acid; 4-methoxy-6-methoxy-carbonyl-10-phenylmethyl-6,7,8,9-tetrahydropyrido[1,2-a]indole; (4-carboxamido-9-phenylmethyl-4,5-dihydrothiopyrano[3,4-b]indol-5-yl)oxyacetic acid; 3,4-dihydro-4-carboxamidol-5-methoxy-9-phenylmethylpyrano[3,4-ib]indole; 2-[(2,9 bis-benzyl-4-carbamoyl-1,2,3,4-tetrahydro-betacarbolin-5-yl)oxy]acetic acid; 2-[4-oxo-5-carboxamido-9-(2-methylbenzyl)-9/-/-pyrido[3,4-ib]indolyl]acetic acid; 2-[4-oxo-5-carboxamido-9-(3-methylbenzyl)-9/-/-pyrido[3,4-ib]indolyl]acetic acid; 2-[4-oxo-5-carboxamido-9-(4-methylbenzyl)-9/-/-pyrido[3,4-ib]indolyl]acetic acid; 2-[4-oxo-5-carboxamido-9-(4-tert-butylbenzyl)-9/-/-pyrido[3,4-ib]indolyl]acetic acid; 2-[4-oxo-5-carboxamido-9-pentafluorobenzyl-9/-/-pyrido[3,4-ib]indolyl]acetic acid; 2-[4-oxo-5-carboxamido-9-(2-fluorobenzyl)-9/-/-pyrido[3,4-ib]indolyl]acetic acid; 2-[4-oxo-5-carboxamido-9-(3-fluorobenzyl)-9/-/-pyrido[3,4-ib]indolyl]acetic acid; 2-[4-oxo-5-carboxamido-9-(4-fluorobenzyl)-9/-/-pyrido[3,4-ib]indolyl]acetic acid; 2-[4-oxo-5-carboxamido-9-(2,6-difluorobenzyl)-9/-/-pyrido[3,4-ib]indolyl]acetic acid; 2-[4-oxo-5-carboxamido-9-(3,4-difluorobenzyl)-9/-/-pyrido[3,4-ib]indolyl]acetic acid; 2-[4-oxo-5-carboxamido-9-(2,5-difluorobenzyl)-9/-/-pyrido[3,4-ib]indolyl]acetic acid; 2-[4-oxo-5-carboxamido-9-(3,5-difluorobenzyl)-9/-/-pyrido[3,4-ib]indolyl]acetic acid; 2-[4-oxo-5-carboxamido-9-(2,4-difluorobenzyl)-9/-/-pyrido[3,4-ib]indolyl]acetic acid; 2-[4-oxo-5-carboxamido-9-(2,3-difluorobenzyl)-9/-/-pyrido[3,4-ib]indolyl]acetic acid; 2-[4-oxo-5-carboxamido-9-[2-(trifluoromethyl)benzyl]-9/-/-pyrido[3,4-ib]indolyl]acetic acid; 2-[4-oxo-5-carboxamido-9-[2-(trifluoromethyl)benzyl]-9/-/-pyrido[3,4-ib]indolyl]acetic acid; 2-[4-oxo-5-carboxamido-9-[3-(trifluoromethyl)benzyl]-9/-/-pyrido[3,4-ib]indolyl]acetic acid; 2-[4-oxo-5-carboxamido-9-[4-(trifluoromethyl)benzyl]-9/-/-pyrido[3,4-ib]indolyl]acetic acid; 2-[4-oxo-5-carboxamido-9-[3,5-bis(trifluoromethyl)benzyl]-9/-/-pyrido[3,4-ib]indolyl]acetic acid: 2-[4-oxo-5-carboxamido-9-[2,4-bis(trifluoromethyl)benzyl]-9/-/-pyrido[3,4-ib]indolyl]acetic acid; 2-[4-oxo-5-carboxamido-9-(a-methylnaphthyl)-9/-/-pyrido[3,4-ib]indolyl]acetic acid; 2-[4-oxo-5-carboxamido-9-(b-methylnaphthyl)-9/-/-pyrido[3,4-ib]indolyl]acetic acid; 2-[4-oxo-5-carboxamido-9-(3,5-dimethylbenzyl)-9/-/-pyrido[3,4-ib]indolyl]acetic acid; 2-[4-oxo-5-carboxamido-9-(2,4-dimethylbenzyl)-9/-/-pyrido[3,4-ib]indolyl]acetic acid; 2-[4-oxo-5-carboxamido-9-(2-phenylbenzyl)-9/-/-pyrido[3,4-ib]indolyl]acetic acid; 2-[4-oxo-5-carboxamido-9-(3-phenylbenzyl)-9/-/-pyrido[3,4-ib]indolyl]acetic acid; 2-[4-oxo-5-carboxamido-9-(4-phenylbenzyl)-9/-/-pyrido[3,4-ib]indolyl]acetic acid; 2-[4-oxo-5-carboxamido-9-(1-fluorenylmethyl)-9/-/-pyrido[3,4-ib]indolyl]acetic acid; 2-[4-oxo-5-carboxamido-9-(2-fluoro-3-methylbenzyl)-9/-/-pyrido[3,4-ib]indolyl]acetic acid; 2-[4-oxo-5-carboxamido-9-(3-benzoylbenzyl)-9/-/-pyrido[3,4-ib]indolyl]acetic acid; 2-[4-oxo-5-carboxamido-9-(2-phenoxybenzyl)-9/-/-pyrido[3,4-ib]indolyl]acetic acid; 2-[4-oxo-5-carboxamido-9-(3-phenoxybenzyl)-9/-/-pyrido[3,4-ib]indolyl]acetic acid; 2-[4-oxo-5-carboxamido-9-(4-phenoxybenzyl)-9/-/-pyrido[3,4-ib]indolyl]acetic acid; 2-[4-oxo-5-carboxamido-9-[3-[2-(fluorophenoxy)benzyl]]-9/-/-pyπdo[3,4-ib]indolyl]acetic acid; 2-[4-oxo-5-carboxamido-9-[3-[4-(fluorophenoxy)benzyl]]-9/-/-pyrido[3,4-ib]indolyl]acetic acid; 2-[4-oxo-5-carboxamido-9-[2-fluoro-3-(trifluoromethyl)benzyl]-9/-/-pyπdo[3,4-£>]indolyl]acetic acid; 2-[4-oxo-5-carboxamido-9-[2-fluoro-4-(trifluoromethyl)benzyl]-9/-/-pyrido[3,4-ib]indolyl]acetic acid; 2-[4-oxo-5-carboxamido-9-[2-fluoro-5-(trifluoromethyl)benzyl]-9H-pyrido[3,4-ib]indolyl]acetic acid; 2-[4-oxo-5-carboxamido-9-[3-fluoro-5-(trifluoromethyl)benzyl]-9/-/-pyrido[3,4-ib]indolyl]acetic acid; 2-[4-oxo-5-carboxamido-9-[4-fluoro-2-(trifluoromethyl)benzyl]-9/-/-pyrido[3,4-ib]indolyl]acetic acid; 2-[4-oxo-5-carboxamido-9-[4-fluoro-3-(trifluoromethyl)benzyl]-9/-/-pyrido[3,4-ib]indolyl]acetic acid; 2-[4-oxo-5-carboxamido-9-[2-fluoro-6-(trifluoromethyl)benzyl]-9/-/-pyrido[3,4-ιb]indolyl]acetic acid; 2-[4-oxo-5-carboxamido-9-(2,3,6-trifluorobenzyl)-9/-/-pyrido[3,4-ib]indolyl]acetic acid; 2-[4-oxo-5-carboxamido-9-(2,3,5-trifluorobenzyl)-9/-/-pyrido[3,4-ιb]indolyl]acetic acid; 2-[4-oxo-5-carboxamido-9-(2,4,5-trifluorobenzyl)-9/-/-pyrido[3,4-ib]indolyl]acetic acid; 2-[4-oxo-5-carboxamido-9-(2,4,6-trifluorobenzyl)-9/-/-pyrido[3,4-ιb]indolyl]acetic acid; 2-[4-oxo-5-carboxamido-9-(2,3,4-trifluorobenzyl)-9/-/-pyrido[3,4-ib]indolyl]acetic acid; 2-[4-oxo-5-carboxamido-9-(3,4,5-trifluorobenzyl)-9/-/-pyrido[3,4-ib]indolyl]acetic acid; 2-[4-oxo-5-carboxamido-9-[3-(trifluoromethoxyl)benzyl]-9/-/-pyrido[3,4-ib]indolyl]acetic acid; 2-[4-oxo-5-carboxamido-9-[4-(trifluoromethoxyl)benzyl]-9/-/-pyrido[3,4-ib]indolyl]acetic acid; 2-[4-oxo-5-carboxamido-9-[4-methoxy(tetrafluoro)benzyl]-9/-/-pyrido[3,4-ib]indolyl]acetic acid; 2-[4-oxo-5-carboxamido-9-(2-methoxybenzyl)-9/-/-pyrido[3,4-ib]indolyl]acetic acid; 2-[4-oxo-5-carboxamido-9-(3-methoxybenzyl)-9/-/-pyrido[3,4-ib]indolyl]acetic acid; 2-[4-oxo-5-carboxamido-9-(4-methoxybenzyl)-9/-/-pyrido[3,4-ib]indolyl]acetic acid; 2-[4-oxo-5-carboxamido-9-(4-ethylbenzyl)-9/-/-pyπdo[3,4-ib]indolyl]acetic acid; 2-[4-oxo-5-carboxamido-9-(4-isopropylbenzyl)-9/-/-pyrido[3,4-ib]indolyl]acetic acid; 2-[4-oxo-5-carboxamido-9-(3,4,5-trimethoxybenzyl)-9/-/-pyrido[3,4-ib]indolyl]acetic acid; 2-[4-oxo-5-carboxamido-9-(3,4-methylenedioxybenzyl)-9/-/-pyrido[3,4-ib]indolyl]acetic acid; 2-[4-oxo-5-carboxamido-9-(4-methoxy-3-methylbenzyl)-9/-/-pyπdo[3,4-ib]indolyl]acetic acid; 2-[4-oxo-5-carboxamido-9-(3,5-dimethoxybenzyl)-9/-/-pyπdo[3,4-ib]indolyl]acetic acid; 2-[4-oxo-5-carboxamido-9-(2,5-dimethoxybenzyl)-9/-/-pyπdo[3,4-ib]indolyl]acetic acid; 2-[4-oxo-5-carboxamido-9-(4-ethoxybenzyl)-9/-/-pyrido[3,4-ib]indolyl]acetic acid; 2-[4-oxo-5-carboxamido-9-(cyclohexylmethyl)-9/-/-pyrido[3,4-ib]indolyl]acetic acid; 2-[4-oxo-5-carboxamido-9-(cyclopentylmethyl)-9/-/-pyrido[3,4-ib]indolyl]acetic acid; 2-[4-oxo-5-carboxamido-9-ethyl-9/-/-pyrido[3,4-ib]indolyl]acetic acid; 2-[4-oxo-5-carboxamido-9-(1-propyl)-9/-/-pyrido[3,4-ib]indolyl]acetic acid; 2-[4-oxo-5-carboxamido-9-(2-propyl)-9/-/-pyrido[3,4-ib]indolyl]acetic acid; 2-[4-oxo-5-carboxamido-9-(1-butyl)-9H-pyrido[3,4-]indolyl]acetic acid; 2-[4-oxo-5-carboxamido-9-(2-butyl)-9/-/-pyrido[3,4-ib]indolyl]acetic acid; 2-[4-oxo-5-carboxamido-9-isobutyl-9/-/-pyrido[3,4-ib]indolyl]acetic acid; 2-[4-oxo-5-carboxamido-9-[2-(1-phenylethyl)]-9/-/-pyrido[3,4-ib]indolyl]acetic acid; 2-[4-oxo-5-carboxamido-9-[3-(1-phenylpropyl)]-9/-/-pyrido[3,4-ib]indolyl]acetic acid; 2-[4-oxo-5-carboxamido-9-[4-(1-phenylbutyl)]-9/-/-pyrido[3,4-ib]indolyl]acetic acid; 2-[4-oxo-5-carboxamido-9-(1-pentyl)-9/-/-pyrido[3,4-ib]indolyl]acetic acid; 2-[4-oxo-5-carboxamido-9-(1-hexyl)-9/-/-pyrido[3,4-ib]indolyl]acetic acid; 4-[(9-benzyl-4-carbamoyl-1,2,3,4-tetrahydrocarbazol-6-yl)oxy]butyric acid; 3-[(9-benzyl-4-carbamoyl-1,2,3,4-tetrahydrocarbazol-θ-yOoxylpropylphosphonic acid; 2-[(9-benzyl-4-carbamoyl-1,2,3,4-tetrahydrocarbazol-6-yl)oxy]methylbenzoic acid; 3-[(9-benzyl-4-carbamoyl-7-n-octyl-1,2,3,4-tetrahydrocarbazol-6-yl)oxy]propylphosphonic acid; 4-[(9-benzyl-4-carbamoyl-7-ethyl-1,2,3,4-tetrahydrocarbazol-6-yl)oxy]butyric acid; 3-[(9-benzyl-4-carbamoyl-7-ethyl-1,2,3,4-tetrahydrocarbazol-6-yl)oxy]propylphosphonic acid; 3-[(9-benzyl-4-carbamoyl-7-ethyl-1,2,3,4-tetrahydrocarbazol-6-yl)oxy]propylphosphonic acid; (S)-(+)-4-[(9-benzyl-4- carbamoyl-7-ethyl-1,2,3,4-tetrahydrocarbazol-6-yl)oxy]
butyric acid; 4-[9-benzyl-4-carbamoyl-6-(2-cyanoethyl)-1,
2,3,4-tetrahydrocarbazol-6-yl]oxybutyric acid; 4-[9-benzyl-
4-carboxamido-7-(2-phenylethyl)-1,2,3,4-
tetrahydrocarbazol-6-yl]oxybutyric acid; 4-[9-benzyl-4-
carboxamidocarbazol-6-yl]oxybutyric acid; methyl 2-[(9-
benzyl-4-carbamoyl-1,2,3,4-tetrahydrocarbazol-6-yl)oxy]
methylbenzoate; 4-[9-benzyl-4-carbamoyl-7-(2-
cyanoethyl)-1,2,3,4-tetrahydrocarbazol-6-yl]oxybutyric
acid; 9-benzyl-7-methoxy-5-cyanomethyloxy-tetrahydro-
carbazole-carboxamide; [9-benzyl-4-carbamoyl-8-methyl-
carbazole-5-yl]oxyacetic acid; and [θ-benzyM-carbamoyl-
carbazole-8-yl]oxyacetic acid, or pharmaceutically
acceptable salts, solvates, prodrug derivatives, racemates,
tautomers, or optical isomers thereof. Direct and indirect
$PLA_2$ inhibitors also include N,N-dimethylcarbamoylm-
ethyl,4-4-guanidinobenzoyloxy-phenylacetate (Camostat,
camostate) or ethyl-p[6-guanidinohexanoyloxy]-benzoate
methansulfonate (gabexate) and leukotriene synthesis
inhibitor selected from the group consisting of methyl
arachidonyl fluorophosphonate (MAFP), pyrroxyphene,
ONO-RS-082, 1-[3-(4-octylphenoxy)-2-oxopropyl]indole-
5-carboxylic acid, 1-[3-(4-octylphenoxy)-2-oxopropyl]in-
dole-6-carboxylic acid, arachidonyl trifluoromethyl ketone,
D609, 4-{3-[5-chloro-2-(2-{([(3,4-dichlorobenzyl)sulfonyl]
amino}ethyl)-1-(diphenylmethyl)-1H-indol-3-yl]propyl)
benzoic acid (WAY-196025), efipladib, 4-{2-[5-chloro-2-(2-
{[(3,4-dichlorobenzyl)sulfonyl]amino}-ethyl)-1-
(diphenylmethyl)-1H-indol-3-yl]ethoxy}benzoic acid,
Ecopladib, (E)-N-[(2S,4R)-4-[N-(biphenyl-2-ylmethyl)-N-
2-methylpropylamino]-1-[2-(2,-4-difluorobenzoyl)benzoyl]
pyrrolidin-2-yl]methyl-3-[4-(2,4-dioxothiazolidi-n-5-
ylidenemethyl) phenyl]acrylamide (RSC-3388), berberine,
glutamine, darapladib or a pharmaceutically acceptable salt
thereof.

"Metalloprotease inhibitors" include, but are not limited
to, prinomastat, BB-94 (marimastat), BB-2516 (batimastat),
vorinostat, cefixime and doxycycline. Other metalloprotease
inhibitors that may be used in the invention include but are
not limited to, TAPI-2, TAPI-1, EGTA, EDTA, phosphora-
madon, TAPI-0, Luteolin, alendronate, tanomastat, ilomas-
tat, prinomastat, nafamostat, collagenase inhibitor 1, Ro-32-
3555, lactobionic acid, o-phenantroline, ecotin, 4-epi-
chlortetracycline, teracycline, doxycycline or related
antibiotic with additional, salutary antimicrobial effect,
n-dansyl-d-phenylalanine, 20[R]ginsenosideRh2, pro-leu-
gly-hydroxymate, gm6001, actinonin, arp-100, MMP9
inhibitor I, MMP2 inhibitor I, SB-3CT, Thiorphan (DL),
4-epi-demeclocycline, zinc methacrylate, funalenone, and
their analogs, derivatives, pharmaceutically acceptable salts,
enantiomers, diastereomers, solvates and polymorphs and
mixtures thereof.

Unexpectedly, use of at least one PLA2 inhibitor and/or a
metalloprotease inhibitor as described herein in combination
with one or more antibiotics as described herein has been
found to be particularly effective to ameliorate, inhibit
and/or reduce the likelihood of an injured patient or subject
at risk of becoming infected or who has become infected
such that the infection will produce one or more of sepsis,
septic shock, an acute inflammatory syndrome such as
systemic inflammatory response syndrome (SIRS) and/or
acute respiratory distress syndrome (ARDS).

The term "neo-natal ARDS" is used to describe a common
clinical critical disease and is one of the main causes of
death and disability in neonates. The etiology and patho-
genesis of neonatal ARDS are complicated. It is an acute
pulmonary inflammatory disease caused by the lack of pulmonary surfactant (PS) related to various pathological
factors. It is often difficult to distinguish neonatal ARDS
from other diseases. Prior to the present invention, there was
no specific treatment method for this disease, although
respiratory support, PS replacement, extracorporeal mem-
brane oxygenation, nutrition support and liquid management
are main treatment strategies. The term "meconium aspira-
tion syndrome" or MAS is a life-threatening type of neonatal
ARDS with high rates of mortality and no approved treat-
ments. meconium aspiration syndrome (MAS) is known to
damage surfactant. It is known that surfactant function is
damaged and correlates with lung aeration and as conse-
quence of these changes, surfactant nanostructure is also
damaged. Meconium is the first feces, or stool, of the
newborn. meconium aspiration syndrome occurs when a
newborn breathes a mixture of meconium and amniotic fluid
into the lungs around the time of delivery. meconium
aspiration syndrome, a leading cause of severe illness and
death in the newborn, occurs in about 5 percent to 10 percent
of births. It typically occurs when the fetus is stressed during
labor, especially when the infant is past its due date. Until
the present invention, there was no known effective thera-
peutic method for meconium aspiration syndrome or MAS.

Pharmaceutical compositions comprising combinations
of an effective amount of an antibiotic as disclosed herein,
often according to the present invention including one or
additional PLA2 inhibitor and/or metalloprotease inhibitor
as otherwise described herein, all in effective amounts, in
combination with a pharmaceutically effective amount of a
carrier, additive or excipient, represent a further aspect of the
present invention. These may be used in combination with at
least one additional, optional bioactive agent, especially
agents which can be used to address additional symptoms of
the patient or subject to be treated.

The compositions of the present invention may be for-
mulated in a conventional manner using one or more phar-
maceutically acceptable carriers and may also be adminis-
tered in controlled-release formulations. Pharmaceutically
acceptable carriers that may be used in these pharmaceutical
compositions include, but are not limited to, ion exchangers,
alumina, aluminum stearate, lecithin, serum proteins, such
as human serum albumin, buffer substances such as phos-
phates, glycine, sorbic acid, potassium sorbate, partial glyc-
eride mixtures of saturated vegetable fatty acids, water, salts
or electrolytes, such as prolamine sulfate, disodium hydro-
gen phosphate, potassium hydrogen phosphate, sodium
chloride, zinc salts, colloidal silica, magnesium trisilicate,
polyvinyl pyrrolidone, cellulose-based substances, polyeth-
ylene glycol, sodium carboxymethylcellulose, polyacry-
lates, waxes, polyethylene-polyoxypropylene-block poly-
mers, polyethylene glycol and wool fat.

The compositions of the present invention may be admin-
istered orally, intratracheally, parenterally, by inhalation
spray, topically, rectally, nasally, buccally, vaginally or via
an implanted reservoir, among others. The term "parenteral"
as used herein includes subcutaneous, intravenous, intra-
muscular, intra-articular, intra-synovial, intrasternal, intrath-
ecal, intrahepatic, intralesional and intracranial injection or
infusion techniques. Preferably, the compositions are admin-
istered orally (including via intubation through the mouth or
nose into the stomach), intraperitoneally or intravenously.

Sterile injectable forms of the compositions of this inven-
tion may be aqueous, a stabilized liquid or oleaginous
suspension. These suspensions may be formulated according
to techniques known in the art using suitable dispersing or
wetting agents and suspending agents. The sterile injectable
preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin bacterial infections or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers or administered by microneedle patch. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional compound which may be used to treat a pathogen, especially a bacterial (often a gram-negative bacterial) infection or a secondary effect or condition thereof.

Methods of treating patients or subjects in need for a particular disease state or condition as otherwise described herein, especially a pathogen, especially a bacterial infection, in particular, a gram-negative bacterial infection, comprise administration of an effective amount of a pharmaceutical composition comprising therapeutic amounts of one or more of the novel compounds described herein and optionally at least one additional bioactive (e.g. additional antibiotic) agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dose of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 250 mg/kg of the novel compounds can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a human) suffering from a bacterial infection can be treated by administering to the patient (subject) an effective amount of a compound according to the present invention including pharmaceutically acceptable salts, solvates or polymorphs, thereof optionally in a pharmaceutically acceptable carrier or diluent, either alone, or in combination with other known antibiotic or pharmaceutical agents, preferably agents which can assist in treating the bacterial infection or ameliorate the secondary effects and conditions associated with the infection. This treatment can also be administered in conjunction with other conventional therapies known in the art.

The present compounds, alone or in combination with other agents as described herein, can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from about 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches, sachets and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, anti-inflammatories, or anti-viral compounds. In certain preferred aspects of the invention, one or more chimeric antibody-recruiting compound according to the present invention is co-administered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled and/or sustained release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions or cholestosomes may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

EXAMPLES

Unbeknownst to the investigators, juvenile pigs in a herd shipped for research were not prophylaxed for *Streptococcus suis* (*S. suis*) a bacterium that is lethal to pigs and can also cause lethality in humans when exposed to sick or colonized animals. One juvenile pig (Sus *domesticus*) became weak after becoming febrile 12 hours after major resuscitation and was euthanized. The pathologist noted an unusually high bacterial load immediately, which was visibly apparent on microscopy. Tissues and catheter tip were cultured, confirming *S. suis* infection. The medication itself was cultured and no bacterial contamination was detected. A second juvenile pig which was being treated with LY315920 alone and a single antibiotic dose given to the surviving members of the heard for experimental envenoming survived for >100 hours until euthanized as scheduled at the end of the study period with an non-curative dose of antibiotics. On autopsy it was noted that the pig had significant evidence of *S. suis* infection, but the animal had only received antibiotics following realization that a first animal had died of septicemia rather than as a result of experimental envenoming by taipan venom.

Further Examples: Viruses and Bacteria Including COVID-19 and Anthrax

In severe cases of infection such as those caused by coronaviruses (e.g. SARS, MERS, COVID-19, bacteria such as anthrax, fungi, or co- and secondary infections), the immune system may overreact and start attacking lung cells, neural tissues with accompanying or preceding endothelial damage all resulting in maladaptive elevations of MP and sPLA2 activity as well as other inflammatory species of phospholipase and cytokines. The lungs become obstructed with fluid and dying cells, making it difficult to breathe, neurological complications occur and a substantial percentage of infections can lead to ARDS and death (such as seen with severe coronavirus syndromes such as SARS, MERS and COVID-19 or influenza with or without secondary bacterial pneumonias).

Coronaviruses SARS-CoV and MERS-CoV have, for example, age dependent mortality that has been linked to sPLA2 that was as high as 6% in the 25-44 age group and 15% in the 45-64 year-old age and up to more than 50% case fatality rates in older age groups.[1] The inventors have unexpectedly realized that early administration of these drugs alone or in combination would abort and/or substantially inhibit the sPLA2 and metalloprotease elevations that heralding severe outcomes resulting from acute pulmonary inflammation and cellular injury that can result in long-term pulmonary compromise in survivors. When possible, sPLA2 and MP inhibitors should be administered orally before infection or resulting inflammatory, pulmonary, vascular, neurological and renal sequelae become severe. The following examples are relevant to this analysis.

Example 1

A healthcare worker or field workers encounter a patients with an undefined respiratory illness or newly identified outbreak of a high fatality rate coronavirus or anthrax bacterium in the out of hospital or in hospital setting and suspect an infectious agent. Because of the high-risk occupational environment and risk of transmission from patient to health care worker, an orally bioavailable MP and/or PLA2 inhibitor is administered with or without an antiviral with or without a metalloprotease-suppressing antibiotic medication such as azithromycin (antibiotic) for prophylaxis or to abrogate early symptoms or signs of infection heralding more life-threatening consequences of virally-induced inflammatory responses. Therapy could be instituted prior to onset of severe signs or symptoms or prophylactically resulting in less severe consequences of infection, avoiding intensive care and ventilatory support. This patient or healthcare can be maintained on entirely oral medications for the duration of disease or high risk occupational/high risk contact exposure.

Example 2

A patient has a virally- or bacterially-mediated inflammatory response requiring intravenous medications and intensive care. The patient might or might not have ARDS, neurological sequelae but is sufficiently ill that intravenous infusion of medications are required. Intravenous infusions of an MP and/or PLA2 inhibitor decrease the acuity and dependence on intensive resources because of the suppression of maladaptive MP and/or PLA2-related inflammatory and cytotoxic responses. Once stabilized, this patient can be transitioned to an oral formulation of a MP and/or PLA2 inhibitor, reducing risk of relapse and long-term pulmonary, vascular or neurological damage.

Example 3

Systematic study of forty-one cases of documented Inhalational anthrax from the Sverdlovsk epidemic of 1979 traced to release of aerosols of *Bacillus anthracis* were carried out. Respiratory function was compromised by mediastinal expansion, large pleural effusions, and hematogenous and retrograde lymphatic vessel spread of *B. anthracis* to the lung with consequent pneumonia. These pathologic findings are consistent with previous experimental studies showing transport of inhaled spores to mediastinal lymph nodes, where germination and growth lead to local lesions and systemic spread, with resulting edema and cell death, owing to the effects of edema toxin and lethal toxin. An inhaled, intratracheally applied, IV or oral combination or single agent approach using MP or sPLA2 inhibitors is both prophylactic and therapeutic in human and non-human species. Vero (African green monkey) cell culture exposed to toxic metalloproteases "zincins" and related toxin metalloproteases and phospholipases demonstrates the efficacy of sPLA2 and metalloprotease inhibition to protect cell junction integrity.

Further Examples

Methods

Figure 1A:
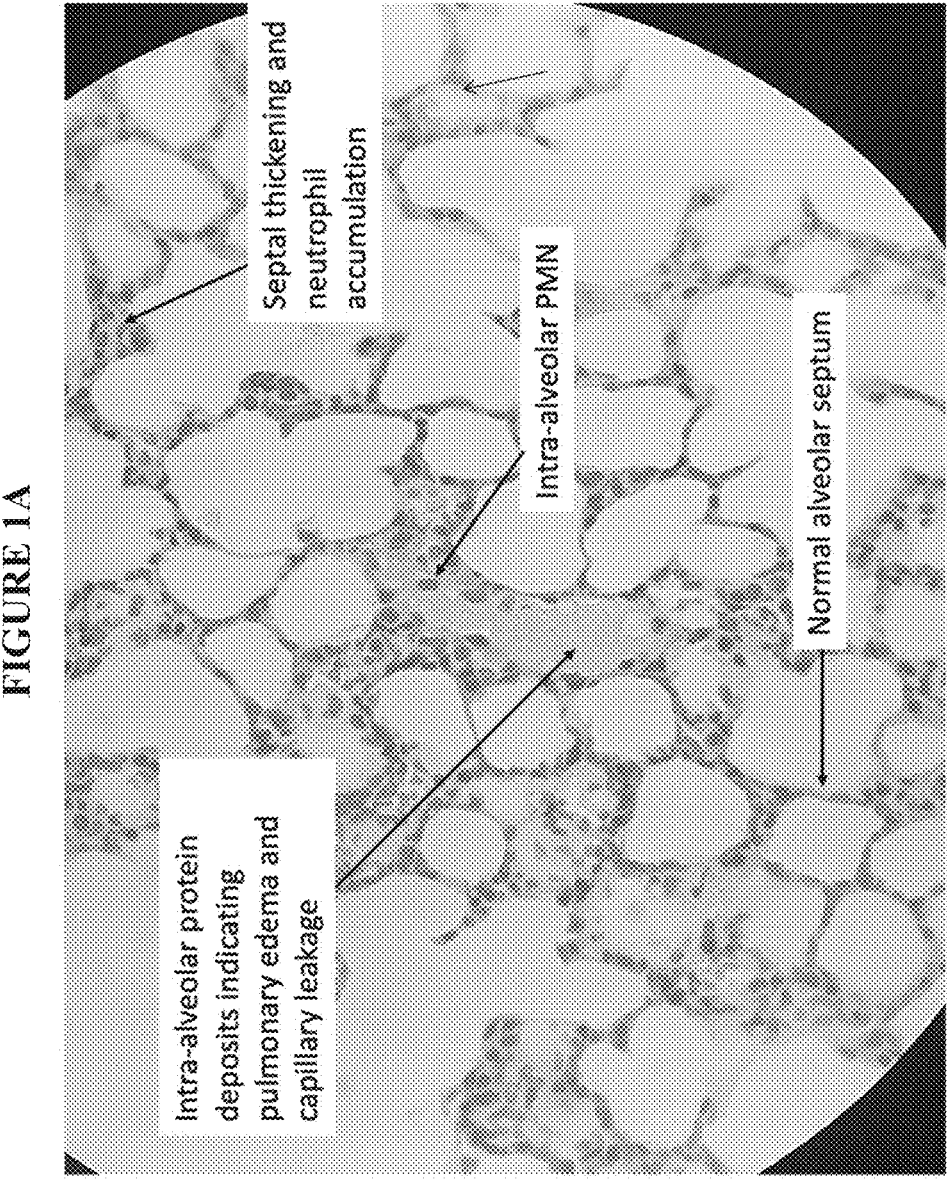
FIG. 1A Shows the features of alveolar pathology as summarized in Table 1 in a mouse with ARDS induced by a combination of LPS/OA.
Figure 2:
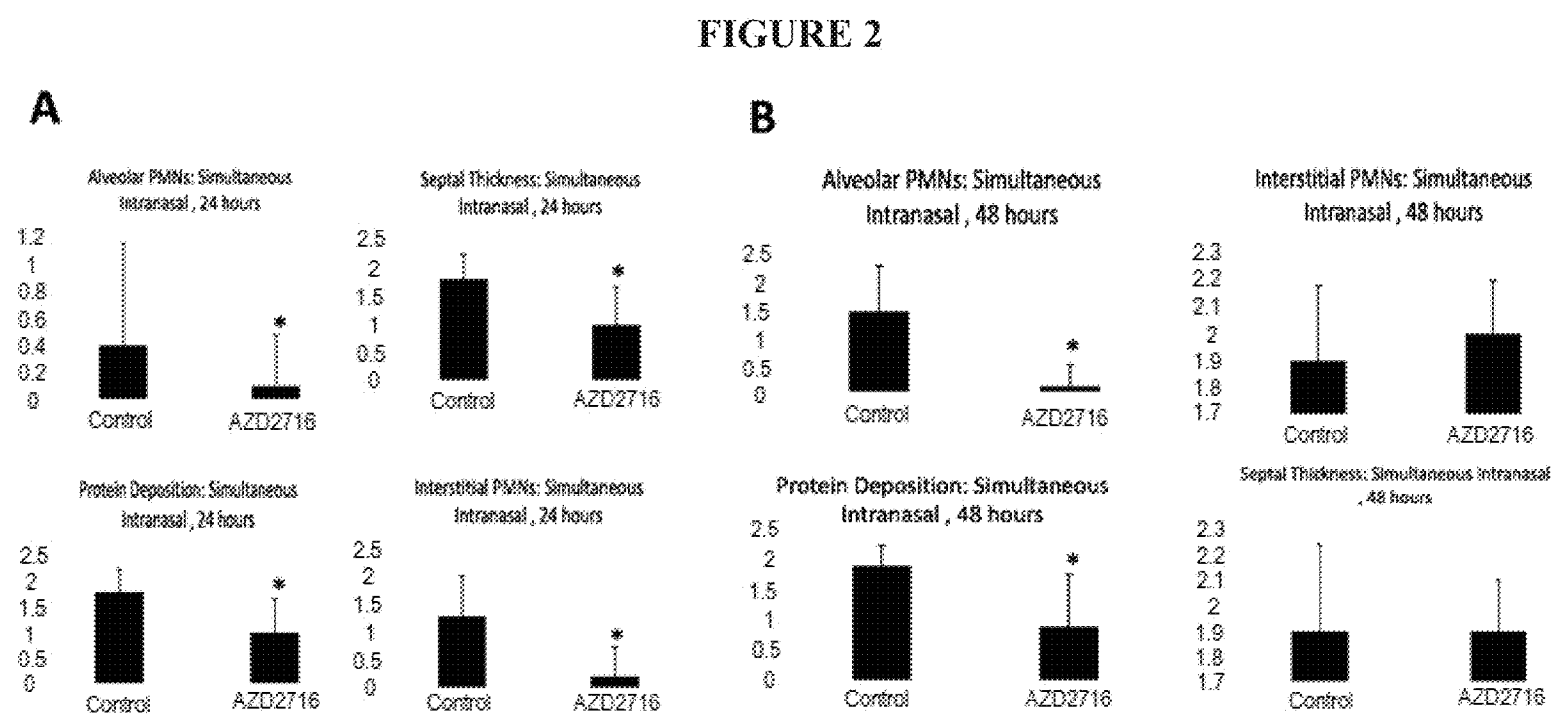
Figure 3:
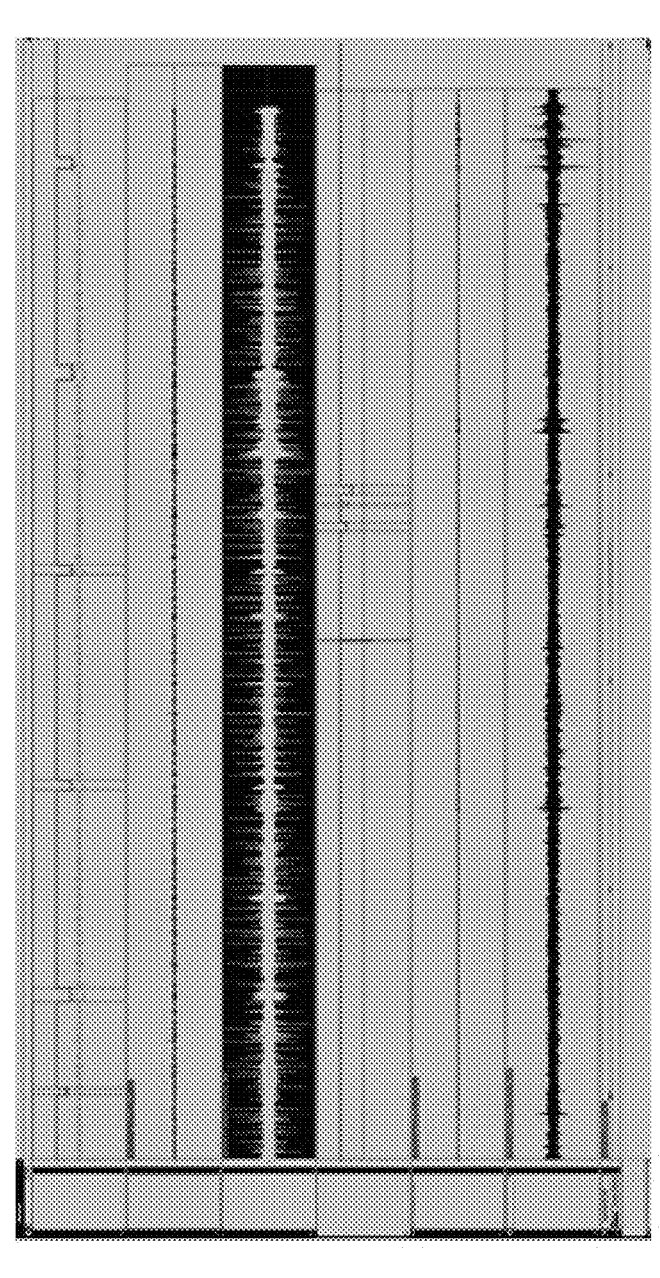
FIG. 3 Shows the composite lung audiograms of mice demonstrating protection from ARDS by intranasally dosed AZD2716 demonstrate ~10 dB difference between treated (quieter) and untreated (louder) mice. The fluid buildup in the mice also makes the lungs heavy and stiff, which decreases the lungs' ability to expand and causes crackling sounds when the alveoli suddenly expand with increased work of breathing. This results from prevention of degradation or restoration of surfactant via Type II epithelial cells responsible for production of surfactant. Measurement of the audiofiles showed roughly a 10 db difference between untreated and treated populations of mice exposed to IN LPS/OA mixtures: −38.5 db (treated, quieter) from maximum and −29.7 db (control, louder) from maximum between control and treated animals.

Mouse Studies: C57BL/6 mice weighing approximately 20 grams were anesthetized using propylene glycol/isoflurane with standard nose-cone procedure. Protection study: Controls (FIGS. 1A, 1B and FIG. 2): 50 µL mixture of 1:1:1:1 LPS (055:B5):Oleic Acid (OA):PBS:Ethanol was instilled intranasally (IN) under anesthesia and the mice recovered for observation. Treated animals received 50 µL 1:1:1:1 LPS (055:B5):Oleic Acid (OA):AZD2716:Ethanol by the same method. Final dose of AZD2716 administered was approximately 5 mg/kg. Audio recordings of lung sounds were made using iPhone 10 and then transferred for amplitude analysis in terms of dB distance from peak (FIG. 3). Rescue studies: (FIG. 5) were conducted similarly but drugs were administered orally alone or in combination mixed in 8% gum Arabic at 10 mg/kg (Prinomastat and/or AZD2716) at 10 ml/kg volume via recurved, stainless steel gavage needle five minutes after IN toxin instillation (75 µL IN) under anesthesia as described, above.

Histology and Interpretation: After 24 or 48 hours, mice were euthanized under deep anesthesia using propylene glycol/isoflurane followed by cervical dislocation and rapid dissection of lungs and kidneys. The lungs inflated with 10% neutral buffered formalin and the kidney placed directly into 10% neutral buffered formalin after nicking the capsule. Tissues were sent to IDEXX Laboratories for mounting and staining with hematoxylin and eosin. Microscopic examination of stained lung sections was conducted and scores were assigned to each section of lung based upon ATS criteria as described by Aeffner et al. *Tox Path,* 43:1074-1092, 2015. A minimum of 25 high power fields were examined by orienting the slide ID tag to the left of the left lung and alternating fields using the fine control outside the atelectatic tissues. Statistics: Scores were averaged and Students t-test applied (two tails, type 2, p<0.05 considered significant).

Enzymatic Assays: Viper, elapid and colubrid venom MP enzymatic activities were optimized Experiments to determine MP activity used validated substrate for MP (DQ Gelatin) and assay run per EnzChek gelatinase assay manufacturer's instructions. These kits were stored as specified if stored at −20° C. PBS is the buffer in the case of MP assays, and absorbance is measured at 495 nm. Substrate for MP is DQ Gelatin and the assay is run per EnzChek gelatinase assay manufacturer's instructions. Dose response curves were constructed by comparing absorbance with different doses of serially diluted inhibitors and compared to controls to determine the $IC_{50}$ for each venom-drug pair and for direct comparison of drugs for their effect on MP activity for each venom (FIG. 4, Table 2).

Cell Culture and Electric Cell-Substrate Impedance Sensing (ECIS) Studies:

FIGS. 6-12: For cell culture and ECIS studies, vero epithelial cells (CCL-81) were cultured in Dulbecco's Modified Eagle Medium (DMEM) supplemented with 5% EquaFETAL (EF) (Atlas Biologicals, Fort Collins, USA) (EF-DMEM) and 100 Units/mL of penicillin and 100 µg/mL of streptomycin (Pen-Strep, see Maghalaes, et al., *Insect Biochem. Mol. Biol.*, 2019, 111, 103169) and plated out on regular 8 or 96 well plates and ECIS plates (96 well) with or without wounding capability. In some studies venom and drug were pre-mixed to assess the ability of the drugs to protect cells from detachment. In others, venom was applied first, followed by drugs in order to assess the ability of the drugs to rescue cells from venom effects 5 to 15 minutes following exposure of vero cells to venom. Typically, samples were run in duplicate at varying concentrations of venom, drug, drug combinations with negative controls (cells grown in media). Cellular wounding protocols were based on manufacturers pre-set recommendations for the specific plate models being used. Venoms and drugs were weighed and diluted to 10 mg/mL stocks in PBS (venoms) or 2.5 or 1 mg/mL stocks in sterile water (drugs) before mixing with cell media at 2× the final concentrations to be used in the wells with final volumes of either 2 mL or 250 µL.

The ECIS-Zθ is an in vitro system that monitors real-time cellular behaviors and movements via gold film electrodes. cell membranes essentially act as insulators. Consequently current flows unrestrained in the absence of cells and constrained once a cell monolayer is established. Changes in the current flow are measured as impedance (Z), which gives insight into two aspects of cellular behaviors and movements at different frequencies. At low frequencies (<10,000 Hz), the cell bodies force the current to flow basolaterally or through the intercellular space between the cell borders. Therefore, resistance (R) is measured at low frequencies and provides information on the barrier integrity. Conversely, the opposition created by the cell membrane is relatively small at high frequencies (>10,000 Hz), so current flows capacitively through the cell bodies. Capacitance (C) is a measure of the electrode coverage by the cells and is indicative of cell migration, as well as cell monolayer disruption following injuries. ECIS can also produce reproducible wounding models by mechanically disrupting a cell monolayer. The ECIS set up can be used to wound a cell monolayer using high current pulse produced via the electrodes. The severity of injury is dependent on the level of current and the duration of the application. The injured or dead cells then detach from the electrode surface which is measured as a rapid increase in the electrode capacitance and a reduction in the resistance. The system then returns to its normal operation and monitors the subsequent recovery as neighboring cells migrate to fill the exposed electrode and re-establish a cell monolayer, see Gu, et al., *Biosensors*. (Basel), 2018, Oct. 11, 8(4), 90.

Methods and compositions for achieving accelerated treatment of wounds and burns, anthrax metalloprotease toxin (lethal factor) driven complications, ARDS, neo-natal and pediatric acute respiratory distress syndrome (neo-natal/pediatric ARDS), including meconium aspiration syndrome are described based on the experimentals described herein above. Thus, the experimentals described above evidence the following observations, among others:

1. Oral prinomastat alone unexpectedly outperformed all inhibitors to treat LPS-Oleic Acid induced ARDS but there were additional benefits from combinations of sPLA2 and metalloprotease inhibition;
2. Locally (respiratory tract) applied of AZD2716 alone prevented and rescued young (~19-20 g) mice from LPS-Oleic Acid induced ARDS, most notably from pulmonary edema. This has significant implications for treatment of neonatal and pediatric ARDS.
3. Low dose Prinomastat+varespladib potentiated both rescue of cultured tissue and accelerated wound healing of experimentally injured tissues in cell culture.

REFERENCES

1. Abraham E, Naum C, Bandi V, Gervich D, Lowry S, Wunderink R, et al. Efficacy and safety of LY315920Na/S-5920, a selective inhibitor of 14-kDa group IIA secretory phospholipase A2. *Crit Care Med.* 2003.
2. Alejandro Piris Gimenez, Yong-Zheng Wu, Miguel Paya, Christophe Delclaux, Lhousseine Touqui, and Pierre L. Goossens. High Bactericidal Efficiency of Type IIA Phospholipase A2 against *Bacillus anthracis* and Inhibition of Its Secretion by the *Lethal Toxin. J. Immunol* 2004; 173:521-530.
3. Becker A B, Roth R A. An unusual active site identified in a family of zinc metalloendopcptidases. *Proc Natl Acad Sci USA.* 1992; 89(9):3835-3839. doi:10.1073/pnas.89.9.3835.
4. Bode W, Gomis-Rüth FX, Stöckler W. Astacins, serralysins, snake venom and matrix metalloproteinases exhibit identical zinc-binding environments (HEXXHXXGXXH and Met-turn) and topologies and should be grouped into a common family, the 'metzincins'. *FEBS Lett.* 1993 Sep. 27; 331(1-2):134-40. doi: 10.1016/0014-5793(93)80312-i. PMID: 8405391.
5. De Luca D, Piastra M, Tosi F, Pulitano S, Mancino A, Genovese O, et al. Pharmacological Therapies for Pediatric and Neonatal AL/ARDS: An Evidence-Based Review. *Curr Drug Targets.* 2012.
6. De Luca D, Vendittelli F, Trias J, Fraser H, Minucci A, Gentile L, et al. Surfactant and Varespladib Co-Administration in Stimulated Rat Alveolar Macrophages Culture. *Curr Pharm Biotechnol.* 2013.
7. De Luca D, Capoluongo E, Rigo V. Secretory phospholipase A2 pathway in various types of lung injury in neonates and infants: A multicentre translational study. *BMC Pediatr.* 2011.
8. Dennis E A, Cao J, Hsu Y H, Magrioti V, Kokotos G. Phospholipase A2 enzymes: Physical structure, biological function, disease implication, chemical inhibition, and therapeutic intervention. *Chemical Reviews.* 2011.

9. Friebe S, van der Goot F G, Bürgi J. The Ins and Outs of Anthrax Toxin. *Toxins (Basel)*. 2016 Mar. 10; 8(3):69. doi: 10.3390/toxins8030069. PMID: 26978402; PMCID: PMC4810214.

10. Furue S, Kuwabara K, Mikawa K, Nishina K, Shiga M, Maekawa N, et al. Crucial role of group IIA phospholipase A2 in oleic acid-induced acute lung injury in rabbits. *Am J Respir Crit Care Med*. 1999.

11. Giordanetto F, Pettersen D, Starke I, Nordberg P, Dahlström M. Knerr L, Selmi N, Rosengren B, Larsson L O, Sandmark J, Castaldo M, Dekker N, Karlsson U, Hurt-Camejo E. Discovery of AZD2716: A Novel Secreted Phospholipase A₂ (sPLA₂) Inhibitor for the Treatment of Coronary Artery Disease. *ACS Med Chem Lett*. 2016 Aug. 9; 7(10):884-889.

12. Goldberg A B, Turk B E. Inhibitors of the Metalloprotcinase Anthrax Lethal Factor. *Curr Top Med Chem*. 2016; 16(21):2350-8.

13. Gomis-Rüth F X, Kress L F, Bode W. First structure of a snake venom metalloproteinase: a prototype for matrix metalloproteinases/collagenases. *EMBO J*. 1993; 12(1 1):4151-4157.

14. Hooper N M. Families of zinc metalloproteases. *FEBS Lett*. 1994 Oct. 31; 354(1):1-6. doi: 10.1016/0014-5793 (94)01079-x. PMID: 7957888.

15. Jiang W, Bond J S. Families of metalloendopeptidases and their relationships. *FEBS Lett*. 1992 Nov. 9; 312(2-3):110-4. doi: 10.1016/0014-5793(92)80916-5. PMID: 1426239.

16. Klimpel K R, Arora N, Leppla S H. Anthrax toxin lethal factor contains a zinc metalloprotease consensus sequence which is required for lethal toxin activity. *Mol Microbiol*. 1994 September; 13(6):1093-100. doi: 10.1111/j.1365-2958.1994.tb00500.x. PMID: 7854123.

17. Liu, S, Moayeri, M. and Leppla, S. H. Anthrax lethal and edema toxins in anthrax pathogenesis. *Trends Microbiol*. 22 (6), 317-325 (2014).

18. Magrioti V, Kokotos G. Phospholipase A2 inhibitors for the treatment of inflammatory diseases: A patent review (2010-present). *Expert Opinion on Therapeutic Patents*. 2013.

19. Piris-Gimenez A. Paya M, Lambeau G. Chignard M. Mock M, Touqui L, Goossens P L. In vivo protective role of human group IIa phospholipase A2 against experimental anthrax. *J Immunol*. 2005 Nov. 15; 175(10):6786-91. doi: 10.4049/jimmunol.175.10.6786. PMID: 16272335.

20. Rawlings N D. Barrett A J. Evolutionary families of peptidases. *Biochem J*. 1993 Feb. 15; 290 (Pt 1)(Pt 1):205-18. doi: 10.1042/bj2900205. PMID: 8439290; PMCID: PMC1132403.

21. Raymond B. Leduc D. Ravaux L, et al. Edema toxin impairs anthracidal phospholipase A2 expression by alveolar macrophages. *PLoS Pathog*. 2007; 3(12):e187. doi:10.1371/journal.ppat.0030187.

22. Santos A A, Browning J L, Scheltinga M R, Lynch E A, Brown E F, Lawton P, et al. Are events after endotoxemia related to circulating phospholipase A2? *Ann Surg*. 1994.

23. Shoop W L, Xiong Y, Wiltsic J, Woods A. Guo J. Pivnichny J V, Felcetto T, Michael B F, Bansal A, Cummings R T, Cunningham B R, Friedlander A M, Douglas C M, Patel S B, Wisniewski D, Scapin G, Salowe S P, Zaller D M, Chapman K T, Scolnick E M, Schmatz D M, Bartizal K. MacCoss M, Hermes J D. Anthrax lethal factor inhibition. *Proc Natl Acad Sci USA*. 2005 May 31; 102(22):7958-63.

24. Sims K. Kochi, Giampictro Schiavo, Michéle Mock, Cesare Montecucco, Zinc content of the *Bacillus anthra-*

44

*cis* lethal factor, *FEMS AMicrobiologv Letters*, Volume 124, Issue 3, December 1994, Pages 343-348.

25. Sohail H A, Gutiérrez J M, Mcbs D, Rowan E G, Sohail M, Warrell D A. Venoms, poisons and toxins: evolution and impact of amazing molecules. *J Venom Res*. 2020; 10:1-6. Published 2020 Jan. 12.

26. Sweeney D A, Cui X, Solomon S B, Vitberg D A, Migone T S, Scher D, Danner R L, Natanson C, Subramanian G M, Eichacker P Q. Anthrax lethal and edema toxins produce different patterns of cardiovascular and renal dysfunction and synergistically decrease survival in canines. *J Infect Dis*. 2010 Dec. 15; 202(12):1885-96. doi: 10.1086/657408. Epub 2010 Nov. 10. PMID: 21067373; PMCID: PMC3061475.

What is claimed:

1. A method of inhibiting the rise in or halting the progression of an inflammatory response to injury, infection, a biological agent or iatrogenesis in a patient or subject in need at risk for sepsis and/or an acute inflammatory response comprising administering to said patient or subject an effective amount of a composition comprising at least one PLA2 inhibitor and/or at least one metalloprotease inhibitor.

2. The method according to claim 1 wherein said composition comprises at least one PLA2 inhibitor and at least one metalloprotease inhibitor.

3. The method according to claim 1 wherein said PLA2 inhibitor is at least one compound selected from the group consisting of varespladib (LY315920), methyl varespladib (LY333013), AZD2716—as a racemic mixture or enantiomer thereof, AZD Compound 4, LY433771 ((9-[(phenyl) methyl]-5-carbamoylcarbazol-4-yl) oxyacetic acid) or a pharmaceutically acceptable salt thereof.

4. The method according to claim 1 wherein said metalloprotease inhibitor is selected from the group consisting of prinomastat, BB-94 (marimastat), BB-2516 (batimastat), vorinostat, cefixime and doxycycline, a pharmaceutically acceptable salt thereof or a mixture thereof.

5. The method according to claim 1 wherein said patient is at risk for sepsis.

6. The method according to claim 1 wherein said composition further includes an effective amount of at least one antibiotic.

7. The method according to claim 6 wherein said antibiotic is selected from the group consisting of a penam, a carboxylpenicillin, a cephalosporin, a monobactam, a carbapenem, a fluoroquinoline, a macrolide or a mixture thereof.

8. The method according to claim 6 wherein said antibiotic is selected from the group consisting of ciprofloxacin, levofloxacin, moxifloxacin, penicillin G, doxycycline, chloramphenicol, ofloxacin and mixtures thereof.

9. The method according to claim 1 wherein said patient is at risk for an acute inflammatory response.

10. The method according to claim 1 wherein said acute inflammatory response is acute respiratory distress syndrome (ARDS) or systemic acute inflammatory response syndrome (SIRS).

11. The method according to claim 9 wherein said acute inflammatory response is ARDS.

12. The method according to claim 11 wherein said ARDS is caused by bacterial or viral pneumonia.

13. The method according to claim 11 wherein said ARDS is neo-natal or pediatric acute respiratory distress syndrome.

14. The method according to claim 12 wherein said neo-natal ARDS is meconium aspiration syndrome.

15. The method according to claim 9 wherein said acute inflammatory response is SIRS.

16. The method according to claim 14 wherein said SIRS is cytokine release syndrome.

17. The method according to claim 1 wherein said infection is an anthrax infection.

18. The method according to claim 1 wherein said biological agent is a coronavirus.

19. The method according to claim 15 wherein said corona virus is Middle Eastern respiratory syndrome coronavirus (MERS-COV), severe acute respiratory syndrome coronavirus I (SARS-COV-1 or severe acute respiratory syndrome coronavirus II (SARS-DoV-2).

20. The method according to claim 16 wherein said coronavirus is SARS-CoV-2.

21. The method according to claim 16 wherein said coronavirus is SARS-CoV-1.

22. The method according to claim 16 wherein said coronavirus is MERS-CoV.

23. A method of preserving and/or accelerating the healing of the basement layer membrane, epithelium and/or the endothelium of a patient or subject afflicted by or is at risk for acute respiratory distress syndrome (ARDS) or systemic acute inflammatory response syndrome (SIRS) comprising administering to said patient or subject an effective amount of at least one PLA2 inhibitor and/or at least one metalloprotease inhibitor.

24. The method according to claim 22 wherein said composition comprises at least one PLA2 inhibitor and at least one metalloprotease inhibitor.

25. The method according to claim 22 wherein said PLA2 inhibitor is at least one compound selected from the group consisting of varespladib (LY315920), methyl varespladib (LY333013), AZD2716—as a racemic mixture or enantiomer thereof, AZD Compound 4, LY433771 ((9-[(phenyl) methyl]-5-carbamoylcarbazol-4-yl) oxyacetic acid) or a pharmaceutically acceptable salt thereof.

26. The method according to claim 22 wherein said metalloprotease inhibitor is selected from the group consisting of prinomastat, BB-94 (marimastat), BB-2516 (batimastat), vorinostat, cefixime and doxycycline, a pharmaceutically acceptable salt thereof or a mixture thereof.

27. The method according to claim 23 wherein said PLA2 inhibitor is at least one compound selected from the group consisting of varespladib (LY315920), methyl varespladib (LY333013), AZD2716—as a racemic mixture or enantiomer thereof, AZD Compound 4, LY433771 ((9-[(phenyl) methyl]-5-carbamoylcarbazol-4-yl) oxyacetic acid) or a pharmaceutically acceptable salt thereof and said metalloprotease inhibitor is selected from the group consisting of prinomastat, BB-94 (marimastat), BB-2516 (batimastat), vorinostat, cefixime and doxycycline, a pharmaceutically acceptable salt thereof or a mixture thereof.

28. The method according to claim 22 wherein said basement layer membrane, epithelium and/or endothelium is in the immune system, pulmonary system, gastrointestinal system, renal system, integumentary system or circulatory system of said patient or subject.

29. The method according to claim 22 wherein said healing improves cellular, systemic, and whole organism function in said patient or subject.

* * * * *